United States Patent
Blumberg et al.

(10) Patent No.: US 10,588,935 B2
(45) Date of Patent: *Mar. 17, 2020

(54) FC RECEPTOR (FCRN) BINDING PEPTIDES AND USES THEREOF

(71) Applicants: THE BRIGHAM AND WOMEN'S HOSPITAL, INC., Boston, MA (US); BIOGEN MA INC., Cambridge, MA (US)

(72) Inventors: Richard S. Blumberg, Waltham, MA (US); Timo Rath, Cambridge, MA (US); Kristi Baker, Brookline, MA (US); Adam Mezo, Carmel, IN (US); Zachary Taylor, Crestview Hills, KY (US); Kevin McDonnell, Lexington, MA (US); Rosa Maria Silva Garcia Grenha, Arlington, MA (US)

(73) Assignees: THE BRIGHAM AND WOMEN'S HOSPITAL, INC., Boston, MA (US); BIOGEN MA INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/293,879

(22) Filed: Mar. 6, 2019

(65) Prior Publication Data

US 2020/0023034 A1    Jan. 23, 2020

Related U.S. Application Data

(63) Continuation of application No. 16/029,835, filed on Jul. 9, 2018, which is a continuation of application No. 15/354,375, filed on Nov. 17, 2016, now Pat. No. 10,046,023, which is a continuation of application No. 14/897,999, filed as application No. PCT/US2014/042932 on Jun. 18, 2014, now Pat. No. 9,527,890.

(60) Provisional application No. 61/836,279, filed on Jun. 18, 2013.

(51) Int. Cl.
| | | |
|---|---|---|
| A61K 38/10 | (2006.01) |
| C07K 14/735 | (2006.01) |
| C07K 14/765 | (2006.01) |
| A61K 47/54 | (2017.01) |
| C07K 7/08 | (2006.01) |
| C12N 15/10 | (2006.01) |
| G01N 33/50 | (2006.01) |
| C07K 14/00 | (2006.01) |
| A61K 38/00 | (2006.01) |

(52) U.S. Cl.
CPC ............ *A61K 38/10* (2013.01); *A61K 47/54* (2017.08); *C07K 7/08* (2013.01); *C07K 14/001* (2013.01); *C07K 14/70535* (2013.01); *C07K 14/765* (2013.01); *C12N 15/1037* (2013.01); *G01N 33/5023* (2013.01); *A61K 38/00* (2013.01); *C07K 2319/00* (2013.01); *C07K 2319/31* (2013.01); *C07K 2319/40* (2013.01)

(58) Field of Classification Search
None
See application file for complete search history.

(56) References Cited

U.S. PATENT DOCUMENTS

| 9,527,890 B2 | 12/2016 | Blumberg et al. |
| 2007/0083334 A1 | 4/2007 | Mintz et al. |
| 2012/0107845 A1 | 5/2012 | Blumberg et al. |

FOREIGN PATENT DOCUMENTS

| WO | 2007/098420 A2 | 8/2007 | |
| WO | WO-2007098420 A2 * | 8/2007 | ............... C07K 7/06 |
| WO | 2010/138814 A2 | 12/2010 | |
| WO | WO-2010138814 A2 * | 12/2010 | ........ C07K 14/70535 |

OTHER PUBLICATIONS

Bhutta et al. "Albumin (Serum Albumin)" http://www.labpedia.net/test/10 (Year: 2012).
Guengerich "Mechanisms of drug toxicity and relevance to pharmaceutical development." Drug Metabolism and Pharmacokinetics 26(1):3-14 (2011).

* cited by examiner

*Primary Examiner* — Christina Bradley
*Assistant Examiner* — Zachary J Miknis
(74) *Attorney, Agent, or Firm* — Nixon Peabody LLP; David S. Resnick; Nicole D. Kling

(57) ABSTRACT

The invention provided herein includes isolated polypeptides that specifically block the interaction between neonatal Fc receptor (FcRn) and albumin. Blocking the interaction treats diseases and conditions caused by increased amounts of albumin or modified albumin that possesses pathogenic properties wherein it is deemed desirable to decrease albumin levels. Accordingly, also provided are methods of using these isolated polypeptides to treat various diseases and conditions caused by increased amounts of albumin or modified albumin that possesses pathogenic properties. The invention provided herein also includes isolated polypeptides capable of binding to a non-IgG and non-albumin competitive site on an FcRn alpha 3 domain. These can be useful for tracking FcRn without inhibiting IgG or albumin binding or function. Accordingly, the invention also includes methods and systems to track FcRn without inhibiting IgG or albumin binding or function.

14 Claims, 24 Drawing Sheets
Specification includes a Sequence Listing.

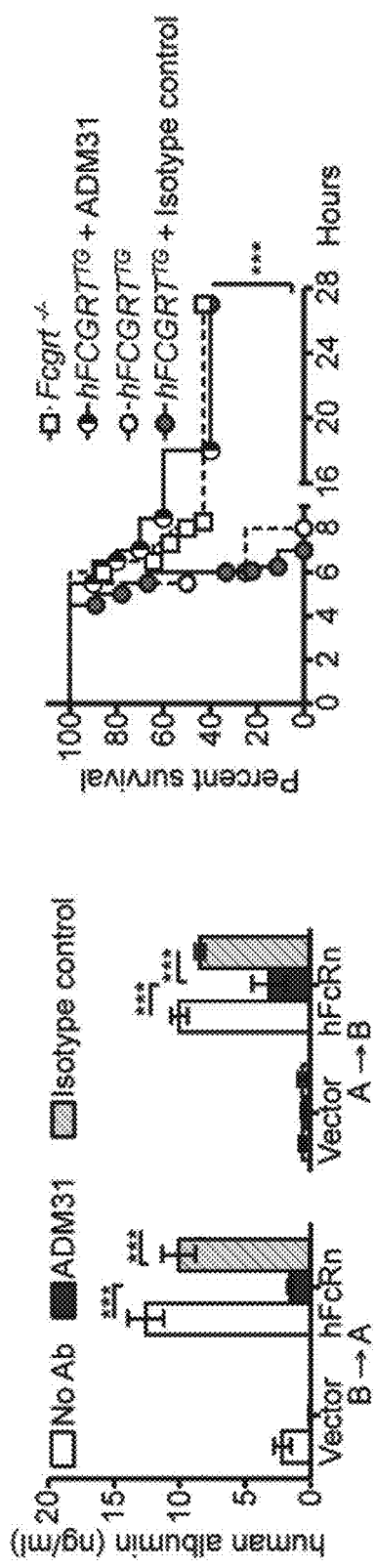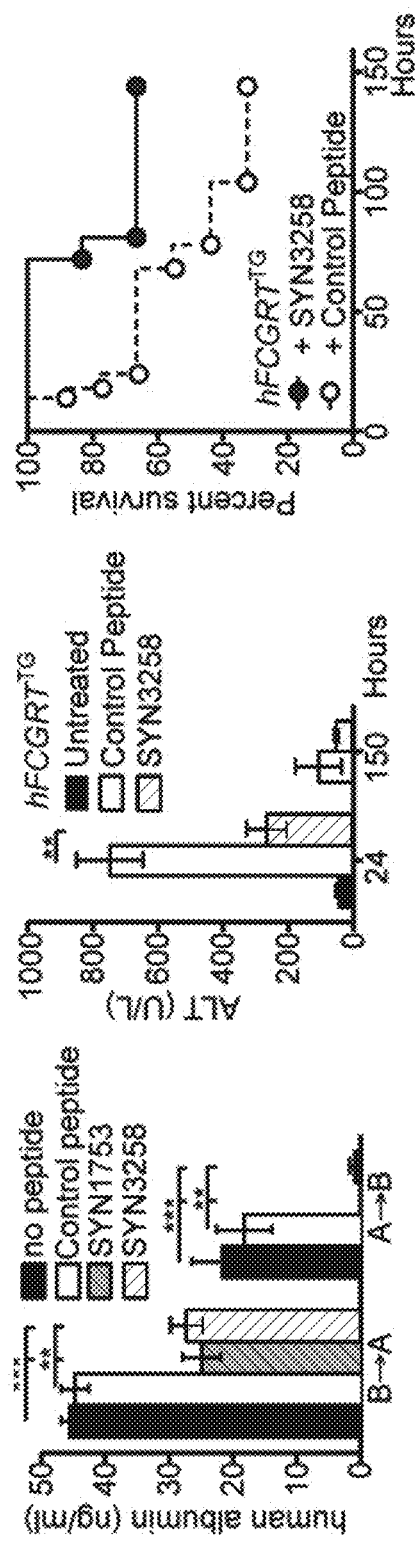
FIG. 12A
FIG. 12B
FIG. 12C
FIG. 12D
FIG. 12E

```
                           SEQUENCE LISTING

<160> NUMBER OF SEQ ID NOS: 124

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Tyr Phe Cys Thr Lys Trp Lys His Gly Trp Cys Glu Glu Val Gly
1               5                   10                  15

Thr

<210> SEQ ID NO 2
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Arg Tyr Phe Cys Thr Lys Trp Lys His Gly Trp Cys Glu Glu Val Gly
1               5                   10                  15

Thr Gly Gly Gly Arg Tyr Phe Cys Thr Lys Trp Lys His Gly Trp Cys
            20                  25                  30

Glu Glu Val Gly Thr
        35

<210> SEQ ID NO 3
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Gly Arg Tyr Phe Cys Thr Lys Trp Lys His Gly Trp Cys Glu Glu
1               5                   10                  15

Val Gly Thr Gly Gly Gly Lys
            20

<210> SEQ ID NO 4
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Gly Val Met His Cys Phe Trp Asp Glu Glu Phe Lys Cys Asp Gln
1               5                   10                  15

Gly Gly Thr Gly Gly Gly Lys
            20

<210> SEQ ID NO 5
```

```
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Gly Tyr Met Thr Cys Lys Trp Asp Asp Gly Phe Ser Cys Glu Tyr
1               5                   10                  15

Val Gly Thr Gly Gly Gly Lys
            20

<210> SEQ ID NO 6
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Gly Val Met Lys Cys Trp Trp Asp Glu Glu Met Leu Cys Arg Ala
1               5                   10                  15

Phe Gly Thr Gly Gly Gly Lys
            20

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or absent
<220> FEATURE:
<221> NAME/KEY: MOD_RES
<222> LOCATION: (3)..(3)
<223> OTHER INFORMATION: Any amino acid or absent
<220> FEATURE:
<221> NAME/KEY: MOD_RES
<222> LOCATION: (5)..(6)
<223> OTHER INFORMATION: Any amino acid or absent
<220> FEATURE:
<221> NAME/KEY: MOD_RES
<222> LOCATION: (8)..(10)
<223> OTHER INFORMATION: Any amino acid or absent
<220> FEATURE:
<221> NAME/KEY: MOD_RES
<222> LOCATION: (13)..(14)
<223> OTHER INFORMATION: Any amino acid or absent
<220> FEATURE:
<221> NAME/KEY: MOD_RES
<222> LOCATION: (16)..(17)
<223> OTHER INFORMATION: Any amino acid or absent
<220> FEATURE:
<223> OTHER INFORMATION: see specification as filed for detailed
      description of substitutions and preferred embodiments

<400> SEQUENCE: 7

Xaa Tyr Xaa Cys Xaa Xaa Trp Xaa Xaa Xaa Trp Cys Xaa Xaa Val Xaa
1               5                   10                  15

Xaa

<210> SEQ ID NO 8
<211> LENGTH: 585
<212> TYPE: PRT
```

<213> ORGANISM: Homo sapiens

<400> SEQUENCE: 8

```
Asp Ala His Lys Ser Glu Val Ala His Arg Phe Lys Asp Leu Gly Glu
1               5                  10                  15
Glu Asn Phe Lys Ala Leu Val Leu Ile Ala Phe Ala Gln Tyr Leu Gln
            20                  25                  30
Gln Cys Pro Phe Glu Asp His Val Lys Leu Val Asn Glu Val Thr Glu
        35                  40                  45
Phe Ala Lys Thr Cys Val Ala Asp Glu Ser Ala Glu Asn Cys Asp Lys
    50                  55                  60
Ser Leu His Thr Leu Phe Gly Asp Lys Leu Cys Thr Val Ala Thr Leu
65                  70                  75                  80
Arg Glu Thr Tyr Gly Glu Met Ala Asp Cys Cys Ala Lys Gln Glu Pro
                85                  90                  95
Glu Arg Asn Glu Cys Phe Leu Gln His Lys Asp Asp Asn Pro Asn Leu
            100                 105                 110
Pro Arg Leu Val Arg Pro Glu Val Asp Val Met Cys Thr Ala Phe His
        115                 120                 125
Asp Asn Glu Glu Thr Phe Leu Lys Lys Tyr Leu Tyr Glu Ile Ala Arg
    130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
            180                 185                 190
Ser Ala Lys Gln Arg Leu Lys Cys Ala Ser Leu Gln Lys Phe Gly Glu
        195                 200                 205
Arg Ala Phe Lys Ala Trp Ala Val Ala Arg Leu Ser Gln Arg Phe Pro
    210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
            260                 265                 270
Ser Lys Leu Lys Glu Cys Cys Glu Lys Pro Leu Leu Glu Lys Ser His
        275                 280                 285
Cys Ile Ala Glu Val Glu Asn Asp Glu Met Pro Ala Asp Leu Pro Ser
    290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
            340                 345                 350
Tyr Glu Thr Thr Leu Glu Lys Cys Cys Ala Ala Ala Asp Pro His Glu
        355                 360                 365
Cys Tyr Ala Lys Val Phe Asp Glu Phe Lys Pro Leu Val Glu Glu Pro
    370                 375                 380
Gln Asn Leu Ile Lys Gln Asn Cys Glu Leu Phe Glu Gln Leu Gly Glu
385                 390                 395                 400
```

```
Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg or a conservative amino acid substitution
      of Arg
<220> FEATURE:
<221> NAME/KEY: MOD_RES
<222> LOCATION: (3)..(3)
<223> OTHER INFORMATION: Phe or a conservative amino acid substitution
      of Phe
<220> FEATURE:
<221> NAME/KEY: MOD_RES
<222> LOCATION: (5)..(5)
<223> OTHER INFORMATION: Thr or a conservative amino acid substitution
      of Thr
<220> FEATURE:
<221> NAME/KEY: MOD_RES
<222> LOCATION: (6)..(6)
<223> OTHER INFORMATION: Lys or a conservative amino acid substitution
      of Lys
<220> FEATURE:
<221> NAME/KEY: MOD_RES
<222> LOCATION: (8)..(8)
<223> OTHER INFORMATION: His or a conservative amino acid substitution
      of His
<220> FEATURE:
<221> NAME/KEY: MOD_RES
<222> LOCATION: (9)..(9)
<223> OTHER INFORMATION: Gly or a conservative amino acid substitution
      of Gly
<220> FEATURE:
<221> NAME/KEY: MOD_RES
<222> LOCATION: (10)..(10)
<223> OTHER INFORMATION: Cys or a conservative amino acid substitution
      of Cys
```

```
<220> FEATURE:
<221> NAME/KEY: MOD_RES
<222> LOCATION: (13)..(14)
<223> OTHER INFORMATION: Glu or a conservative amino acid substitution
      of Glu
<220> FEATURE:
<221> NAME/KEY: MOD_RES
<222> LOCATION: (16)..(16)
<223> OTHER INFORMATION: Gly, a conservative amino acid substitution of
      Gly or absent
<220> FEATURE:
<221> NAME/KEY: MOD_RES
<222> LOCATION: (17)..(17)
<223> OTHER INFORMATION: Thr, a conservative amino acid substitution of
      Thr or absent
<220> FEATURE:
<223> OTHER INFORMATION: see specification as filed for detailed
      description of substitutions and preferred embodiments

<400> SEQUENCE: 9

Xaa Tyr Xaa Cys Xaa Xaa Trp Xaa Xaa Xaa Trp Cys Xaa Xaa Val Xaa
1               5                   10                  15

Xaa

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(6)
<223> OTHER INFORMATION: Any amino acid or absent
<220> FEATURE:
<221> NAME/KEY: MOD_RES
<222> LOCATION: (8)..(10)
<223> OTHER INFORMATION: Any amino acid or absent
<220> FEATURE:
<221> NAME/KEY: MOD_RES
<222> LOCATION: (13)..(14)
<223> OTHER INFORMATION: Any amino acid or absent
<220> FEATURE:
<221> NAME/KEY: MOD_RES
<222> LOCATION: (16)..(17)
<223> OTHER INFORMATION: Any amino acid or absent
<220> FEATURE:
<223> OTHER INFORMATION: see specification as filed for detailed
      description of substitutions and preferred embodiments

<400> SEQUENCE: 10

Arg Tyr Phe Cys Xaa Xaa Trp Xaa Xaa Xaa Trp Cys Xaa Xaa Val Xaa
1               5                   10                  15

Xaa

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Thr or a conservative amino acid substitution
      of Thr
<220> FEATURE:
<221> NAME/KEY: MOD_RES
<222> LOCATION: (6)..(6)
<223> OTHER INFORMATION: Lys or a conservative amino acid substitution
      of Lys
```

```
<220> FEATURE:
<221> NAME/KEY: MOD_RES
<222> LOCATION: (8)..(8)
<223> OTHER INFORMATION: His or a conservative amino acid substitution
      of His
<220> FEATURE:
<221> NAME/KEY: MOD_RES
<222> LOCATION: (9)..(9)
<223> OTHER INFORMATION: Gly or a conservative amino acid substitution
      of Gly
<220> FEATURE:
<221> NAME/KEY: MOD_RES
<222> LOCATION: (10)..(10)
<223> OTHER INFORMATION: Cys or a conservative amino acid substitution
      of Cys
<220> FEATURE:
<221> NAME/KEY: MOD_RES
<222> LOCATION: (13)..(14)
<223> OTHER INFORMATION: Glu or a conservative amino acid substitution
      of Glu
<220> FEATURE:
<221> NAME/KEY: MOD_RES
<222> LOCATION: (16)..(16)
<223> OTHER INFORMATION: Gly, a conservative amino acid substitution of
      Gly or absent
<220> FEATURE:
<221> NAME/KEY: MOD_RES
<222> LOCATION: (17)..(17)
<223> OTHER INFORMATION: Thr, a conservative amino acid substitution of
      Thr or absent
<220> FEATURE:
<223> OTHER INFORMATION: see specification as filed for detailed
      description of substitutions and preferred embodiments

<400> SEQUENCE: 11

Arg Tyr Phe Cys Xaa Xaa Trp Xaa Xaa Xaa Trp Cys Xaa Xaa Val Xaa
1               5                   10                  15

Xaa

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(6)
<223> OTHER INFORMATION: Any amino acid or absent
<220> FEATURE:
<221> NAME/KEY: MOD_RES
<222> LOCATION: (8)..(9)
<223> OTHER INFORMATION: Any amino acid or absent
<220> FEATURE:
<221> NAME/KEY: MOD_RES
<222> LOCATION: (13)..(14)
<223> OTHER INFORMATION: Any amino acid or absent
<220> FEATURE:
<221> NAME/KEY: MOD_RES
<222> LOCATION: (17)..(17)
<223> OTHER INFORMATION: Any amino acid or absent
<220> FEATURE:
<223> OTHER INFORMATION: see specification as filed for detailed
      description of substitutions and preferred embodiments

<400> SEQUENCE: 12

Arg Tyr Phe Cys Xaa Xaa Trp Xaa Xaa Gly Trp Cys Xaa Xaa Val Glu
1               5                   10                  15

Xaa

<210> SEQ ID NO 13
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Thr or a conservative amino acid substitution
      of Thr
<220> FEATURE:
<221> NAME/KEY: MOD_RES
<222> LOCATION: (6)..(6)
<223> OTHER INFORMATION: Lys or a conservative amino acid substitution
      of Lys
<220> FEATURE:
<221> NAME/KEY: MOD_RES
<222> LOCATION: (8)..(8)
<223> OTHER INFORMATION: His or a conservative amino acid substitution
      of His
<220> FEATURE:
<221> NAME/KEY: MOD_RES
<222> LOCATION: (9)..(9)
<223> OTHER INFORMATION: Gly or a conservative amino acid substitution
      of Gly
<220> FEATURE:
<221> NAME/KEY: MOD_RES
<222> LOCATION: (13)..(14)
<223> OTHER INFORMATION: Glu or a conservative amino acid substitution
      of Glu
<220> FEATURE:
<221> NAME/KEY: MOD_RES
<222> LOCATION: (17)..(17)
<223> OTHER INFORMATION: Thr, a conservative amino acid substitution of
      Thr or absent
<220> FEATURE:
<223> OTHER INFORMATION: see specification as filed for detailed
      description of substitutions and preferred embodiments

<400> SEQUENCE: 13

Arg Tyr Phe Cys Xaa Xaa Trp Xaa Xaa Gly Trp Cys Xaa Xaa Val Glu
1               5                   10                  15

Xaa

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(10)
<223> OTHER INFORMATION: This sequence may encompass 1-10 'Gly'
      residues, wherein some positions may be absent
<220> FEATURE:
<223> OTHER INFORMATION: see specification as filed for detailed
      description of substitutions and preferred embodiments

<400> SEQUENCE: 14

Gly Gly Gly Gly Gly Gly Gly Gly Gly Gly
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(10)
```

```
<223> OTHER INFORMATION: Gly or Ser
<220> FEATURE:
<221> NAME/KEY: misc_feature
<222> LOCATION: (1)..(10)
<223> OTHER INFORMATION: This sequence may encompass 1-10 residues,
      wherein some positions may be absent
<220> FEATURE:
<223> OTHER INFORMATION: see specification as filed for detailed
      description of substitutions and preferred embodiments

<400> SEQUENCE: 15

Xaa Xaa Xaa Xaa Xaa Xaa Xaa Xaa Xaa Xaa
1               5                   10

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(5)
<223> OTHER INFORMATION: This sequence may encompass 3-5 'Gly' residues,
      wherein some positions may be absent
<220> FEATURE:
<223> OTHER INFORMATION: see specification as filed for detailed
      description of substitutions and preferred embodiments

<400> SEQUENCE: 16

Gly Gly Gly Gly Gly
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Gly or Ser
<220> FEATURE:
<221> NAME/KEY: misc_feature
<222> LOCATION: (1)..(5)
<223> OTHER INFORMATION: This sequence may encompass 3-5 residues,
      wherein some positions may be absent
<220> FEATURE:
<223> OTHER INFORMATION: see specification as filed for detailed
      description of substitutions and preferred embodiments

<400> SEQUENCE: 17

Xaa Xaa Xaa Xaa Xaa
1               5

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Tyr Phe Cys Thr Lys Trp Lys His Gly Trp Cys Glu Glu Val
1               5                   10                  15

<210> SEQ ID NO 19
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Tyr Phe Cys Thr Lys Trp Lys His Gly Trp Cys Glu Glu Val
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Ala Phe Cys Thr Lys Trp Lys His Gly Trp Cys Glu Glu Val
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Tyr Ala Cys Thr Lys Trp Lys His Gly Trp Cys Glu Glu Val
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Tyr Phe Cys Ala Lys Trp Lys His Gly Trp Cys Glu Glu Val
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Tyr Phe Cys Thr Ala Trp Lys His Gly Trp Cys Glu Glu Val
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24
```

Arg Tyr Phe Cys Thr Lys Ala Lys His Gly Trp Cys Glu Glu Val
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Tyr Phe Cys Thr Lys Trp Ala His Gly Trp Cys Glu Glu Val
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Tyr Phe Cys Thr Lys Trp Lys Ala Gly Trp Cys Glu Glu Val
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Tyr Phe Cys Thr Lys Trp Lys His Ala Trp Cys Glu Glu Val
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Tyr Phe Cys Thr Lys Trp Lys His Gly Ala Cys Glu Glu Val
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Tyr Phe Cys Thr Lys Trp Lys His Gly Trp Cys Ala Glu Val
1               5                   10                  15

<210> SEQ ID NO 30
<211> LENGTH: 15
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 30

Arg Tyr Phe Cys Thr Lys Trp Lys His Gly Trp Cys Glu Ala Val
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Tyr Phe Cys Thr Lys Trp Lys His Gly Trp Cys Glu Glu Ala
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 32

Arg Tyr Phe Xaa Thr Lys Trp Lys His Gly Trp Cys Glu Glu Val
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Pen

<400> SEQUENCE: 33

Arg Tyr Phe Cys Thr Lys Trp Lys His Gly Trp Xaa Glu Glu Val
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (12)..(12)
<223> OTHER INFORMATION: Pen

<400> SEQUENCE: 34

Arg Tyr Phe Xaa Thr Lys Trp Lys His Gly Trp Xaa Glu Glu Val
1               5                   10                  15

```
<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Tyr Phe Ala Thr Lys Trp Lys His Gly Trp Ala Glu Glu Val
1               5                   10                  15

<210> SEQ ID NO 36
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Arg Tyr Phe Cys Thr Lys Trp Lys His Gly Trp Cys Glu Glu Val
1               5                   10                  15

Gly Thr Gly Gly Gly Lys
            20

<210> SEQ ID NO 37
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Tyr Phe Cys Thr Lys Trp Lys His Gly Trp Cys Glu Glu Val Gly
1               5                   10                  15

Thr Gly Gly Gly Lys
            20

<210> SEQ ID NO 38
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ala Gly Arg Tyr Phe Cys Thr Lys Trp Lys His Gly Trp Cys Glu Glu
1               5                   10                  15

Val Gly Thr Gly Gly Gly
            20

<210> SEQ ID NO 39
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Gly Arg Tyr Phe Cys Thr Lys Trp Lys His Gly Trp Cys Glu Glu
1               5                   10                  15
```

Val Gly Thr Gly Gly
         20

<210> SEQ ID NO 40
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Gly Arg Tyr Phe Cys Thr Lys Trp Lys His Gly Trp Cys Glu Glu
1               5                   10                  15

Val Gly Thr Gly
         20

<210> SEQ ID NO 41
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ala Gly Arg Tyr Phe Cys Thr Lys Trp Lys His Gly Trp Cys Glu Glu
1               5                   10                  15

Val Gly Thr

<210> SEQ ID NO 42
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ala Gly Arg Tyr Phe Cys Thr Lys Trp Lys His Gly Trp Cys Glu Glu
1               5                   10                  15

Val Gly

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ala Gly Arg Tyr Phe Cys Thr Lys Trp Lys His Gly Trp Cys Glu Glu
1               5                   10                  15

Val

<210> SEQ ID NO 44
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

```
Val Met His Cys Phe Trp Asp Glu Glu Phe Lys Cys Asp Gln Gly
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Val Met Ala Cys Phe Trp Asp Glu Glu Phe Lys Cys Asp Gln Gly
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Val Met His Cys Phe Trp Asp Glu Ala Phe Lys Cys Asp Gln Gly
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Val Met His Cys Ala Trp Asp Glu Glu Phe Lys Cys Asp Gln Gly
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Tyr Met His Cys Phe Trp Asp Glu Glu Phe Lys Cys Asp Gln Gly
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Val Met His Cys Phe Trp Asp Glu Gly Phe Lys Cys Asp Gln Gly
1               5                   10                  15

<210> SEQ ID NO 50
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 50

Val Met His Cys Phe Trp Asp Glu Glu Phe Lys Cys Glu Gln Gly
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Val Met His Cys Phe Trp Asp Glu Glu Phe Lys Cys Asp Tyr Gly
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Val Met His Cys Phe Trp Asp Glu Glu Phe Lys Cys Asp Gln Val
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Val Met His Cys Phe Trp Asp Glu Glu Phe Arg Cys Asp Tyr Gly
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Val Met His Cys Phe Trp Asp Glu Ala Phe Arg Cys Asp Gln Gly
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Val Met His Cys Phe Trp Asp Glu Glu Phe Arg Cys Glu Tyr Val
1               5                   10                  15
```

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Tyr Met Thr Cys Lys Trp Asp Asp Gly Phe Ser Cys Glu Tyr Val
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ala Met Thr Cys Lys Trp Asp Asp Gly Phe Ser Cys Glu Tyr Val
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Tyr Ala Thr Cys Lys Trp Asp Asp Gly Phe Ser Cys Glu Tyr Val
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Tyr Met Ala Cys Lys Trp Asp Asp Gly Phe Ser Cys Glu Tyr Val
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Tyr Met Thr Cys Ala Trp Asp Asp Gly Phe Ser Cys Glu Tyr Val
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 61

Tyr Met Thr Cys Lys Ala Asp Asp Gly Phe Ser Cys Glu Tyr Val
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Tyr Met Thr Cys Lys Trp Ala Asp Gly Phe Ser Cys Glu Tyr Val
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Tyr Met Thr Cys Lys Trp Asp Ala Gly Phe Ser Cys Glu Tyr Val
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Tyr Met Thr Cys Lys Trp Asp Asp Ala Phe Ser Cys Glu Tyr Val
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Tyr Met Thr Cys Lys Trp Asp Asp Gly Ala Ser Cys Glu Tyr Val
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Tyr Met Thr Cys Lys Trp Asp Asp Gly Phe Ala Cys Glu Tyr Val
1               5                   10                  15

<210> SEQ ID NO 67
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 67

Tyr Met Thr Cys Lys Trp Asp Asp Gly Phe Ser Cys Ala Tyr Val
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Tyr Met Thr Cys Lys Trp Asp Asp Gly Phe Ser Cys Glu Ala Val
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Tyr Met Thr Cys Lys Trp Asp Asp Gly Phe Ser Cys Glu Tyr Ala
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Tyr Met Thr Ala Lys Trp Asp Asp Gly Phe Ser Ala Glu Tyr Val
1               5                   10                  15

<210> SEQ ID NO 71
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Met Thr Cys Lys Trp Asp Asp Gly Phe Ser Cys Glu Tyr Val
1               5                   10

<210> SEQ ID NO 72
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Thr Cys Lys Trp Asp Asp Gly Phe Ser Cys Glu Tyr Val
1               5                   10
```

<210> SEQ ID NO 73
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Cys Lys Trp Asp Asp Gly Phe Ser Cys Glu Tyr Val
1               5                   10

<210> SEQ ID NO 74
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Tyr Met Thr Cys Lys Trp Asp Asp Gly Phe Ser Cys Glu Tyr
1               5                   10

<210> SEQ ID NO 75
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Tyr Met Thr Cys Lys Trp Asp Asp Gly Phe Ser Cys Glu
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Tyr Met Thr Cys Lys Trp Asp Asp Gly Phe Ser Cys
1               5                   10

<210> SEQ ID NO 77
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 77

Tyr Met Thr Xaa Lys Trp Asp Asp Gly Phe Ser Cys Glu Tyr Val
1               5                   10                  15

<210> SEQ ID NO 78
<211> LENGTH: 15
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Pen

<400> SEQUENCE: 78

Tyr Met Thr Cys Lys Trp Asp Asp Gly Phe Ser Xaa Glu Tyr Val
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (12)..(12)
<223> OTHER INFORMATION: Pen

<400> SEQUENCE: 79

Tyr Met Thr Xaa Lys Trp Asp Asp Gly Phe Ser Xaa Glu Tyr Val
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Val Met Lys Cys Trp Trp Asp Glu Glu Met Leu Cys Arg Ala Phe
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Val Met His Cys Trp Trp Asp Glu Glu Met Leu Cys Arg Ala Phe
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Val Met Arg Cys Trp Trp Asp Glu Glu Met Leu Cys Arg Ala Phe
1               5                   10                  15
```

```
<210> SEQ ID NO 83
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Val Met Lys Cys Phe Trp Asp Glu Glu Met Leu Cys Arg Ala Phe
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Val Met Lys Cys Trp Trp Asp Glu Glu Phe Leu Cys Arg Ala Phe
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Val Met Lys Cys Trp Trp Asp Glu Glu Met Arg Cys Arg Ala Phe
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Val Met Lys Cys Trp Trp Asp Glu Glu Met Leu Cys Glu Ala Phe
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Val Met Lys Cys Trp Trp Asp Glu Glu Met Leu Cys Arg Tyr Phe
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88
```

Val Met Lys Cys Trp Trp Asp Glu Glu Met Leu Cys Arg Ala Val
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Val Met Lys Cys Trp Trp Asp Glu Glu Met Leu Cys Arg Ala Val
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Val Met His Ala Phe Trp Asp Glu Glu Phe Arg Ala Glu Tyr Val
1               5                   10                  15

<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

His Thr His Gly Met Asp Glu Leu Lys Tyr
1               5                   10

<210> SEQ ID NO 92
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Gly Ser Gly
1

<210> SEQ ID NO 93
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Gly Ser Gly Gly Gly Ser Gly
1               5

<210> SEQ ID NO 94
<211> LENGTH: 12
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 94

Gly Gly Ser Gly Gly Gly Ser Gly Gly Gly Ser Gly
1               5                   10

<210> SEQ ID NO 95
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Gly Gly Gly Ser Gly Gly Gly Gly Ser Gly Gly Gly Gly Ser
1               5                   10                  15

<210> SEQ ID NO 96
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gly Gly Ser Gly Gly Ser
1               5

<210> SEQ ID NO 97
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
gaagctgctg caagagaagc tgcagctagg gaggctgcag ctagggaggc tgctgcaaga      60

<210> SEQ ID NO 98
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
ggtagcggca gcggtagc                                                   18

<210> SEQ ID NO 99
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
ggtagcggca gcggtagcgg tagcggcagc                                      30

<210> SEQ ID NO 100
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
ggtgaaaatt tgtatttttca atctggtggt                                      30

<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
tccgcttgtt actgtgagct ttcc                                             24

<210> SEQ ID NO 102
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
cgaccagcct gtaagattcc aaatgacctg aagcagaaag ttatgaatca c               51

<210> SEQ ID NO 103
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
ggtggaggag gttctggagg cggtggaagt ggtggcggag gtagc                      45

<210> SEQ ID NO 104
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
ggtggttctg gt                                                          12

<210> SEQ ID NO 105
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
ggtggttctg gtggtggttc tggt                                             24

<210> SEQ ID NO 106
<211> LENGTH: 36
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 106
ggtggttctg gtggtggttc tggtggtggt tctggt                                  36

<210> SEQ ID NO 107
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107
ggtggttctg ccggtggctc cggttctggc tccagcggtg gcagctctgg tgcgtccggc        60
acgggtactg cgggtggcac tggcagcggt tccggtactg gctctggc                    108

<210> SEQ ID NO 108
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108
ggtggttctg gcggcggttc tgaaggtggc ggctccgaag gcggcggcag cgagggcggt        60
ggtagcgaag gtggtggctc cgagggtggc ggttccggcg gcggtagc                    108

<210> SEQ ID NO 109
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109
ggtggttctg gcggcggttc tgaaggtggc ggctccgaag gcggcggcag cgagggcggt        60
ggtagcgaag gtggtggctc cgagggtggc ggttccggcg gcggtagc                    108

<210> SEQ ID NO 110
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110
ggtggttctg ccggtggctc cggttctggc tccagcggtg gcagctctgg tgcgtccggc        60
acgggtactg cgggtggcac tggcagcggt tccggtactg gctctggc                    108

<210> SEQ ID NO 111
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
ggtggaggag gctctggtgg aggcggtagc ggaggcggag ggtcg    45

<210> SEQ ID NO 112
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
ggtggttctg gt    12

<210> SEQ ID NO 113
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
ggtgaaaatt tgtatttca atctggtggt    30

<210> SEQ ID NO 114
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
ggaggttcag gaggcagc    18

<210> SEQ ID NO 115
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 115

His His His His His His
1               5

<210> SEQ ID NO 116
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ala Gly Val Met His Cys Phe Trp Asp Glu Glu Phe Arg Cys Glu Tyr
1               5                   10                  15

Val Gly Thr Gly Gly Gly Lys
            20

<210> SEQ ID NO 117
<211> LENGTH: 25
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 117
cggcgcaact atcggtatca agctg                                             25

<210> SEQ ID NO 118
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
catgtaccgt aacactgagt ttcgtc                                            26

<210> SEQ ID NO 119
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
gataaccgat acaattaagg ctcc                                              24

<210> SEQ ID NO 120
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Arg Tyr Phe Cys Thr Lys Trp Lys His Gly Trp Cys Glu Glu Val Gly
1               5                   10                  15

Thr Gly Gly Gly Arg Tyr Phe Cys Thr Lys Trp Lys His Gly Trp Cys
            20                  25                  30

Val Glu Glu Val Gly Thr
        35

<210> SEQ ID NO 121
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Arg Tyr Phe Cys Thr Lys Trp Lys His Gly Trp Cys Glu Glu Val Gly
1               5                   10                  15

Thr Gly Gly Gly Arg
            20

<210> SEQ ID NO 122
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 122

Val Met Thr Cys Trp Trp Asp Gln Gly Phe Glu Cys Ala Lys Leu
1               5                   10                  15

<210> SEQ ID NO 123
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 123

Arg Phe Xaa Thr Gly His Phe Gly Xaa Leu Tyr Pro Cys
1               5                   10

<210> SEQ ID NO 124
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg or a conservative amino acid substitution
      of Arg
<220> FEATURE:
<221> NAME/KEY: MOD_RES
<222> LOCATION: (3)..(3)
<223> OTHER INFORMATION: Phe or a conservative amino acid substitution
      of Phe
<220> FEATURE:
<221> NAME/KEY: MOD_RES
<222> LOCATION: (5)..(5)
<223> OTHER INFORMATION: Thr or a conservative amino acid substitution
      of Thr
<220> FEATURE:
<221> NAME/KEY: MOD_RES
<222> LOCATION: (6)..(6)
<223> OTHER INFORMATION: Lys or a conservative amino acid substitution
      of Lys
<220> FEATURE:
<221> NAME/KEY: MOD_RES
<222> LOCATION: (8)..(8)
<223> OTHER INFORMATION: Lys or a conservative amino acid substitution
      of Lys
<220> FEATURE:
<221> NAME/KEY: MOD_RES
<222> LOCATION: (9)..(9)
<223> OTHER INFORMATION: His or a conservative amino acid substitution
      of His
<220> FEATURE:
<221> NAME/KEY: MOD_RES
<222> LOCATION: (10)..(10)
<223> OTHER INFORMATION: Gly or a conservative amino acid substitution
      of Gly
<220> FEATURE:
<221> NAME/KEY: MOD_RES
<222> LOCATION: (13)..(14)
<223> OTHER INFORMATION: Glu or a conservative amino acid substitution
      of Glu
```

-continued

```
<220> FEATURE:
<221> NAME/KEY: MOD_RES
<222> LOCATION: (16)..(16)
<223> OTHER INFORMATION: Gly or a conservative amino acid substitution
      of Gly or absent
<220> FEATURE:
<221> NAME/KEY: MOD_RES
<222> LOCATION: (17)..(17)
<223> OTHER INFORMATION: Thr or a conservative amino acid substitution
      of Thr or absent
<220> FEATURE:
<223> OTHER INFORMATION: see specification as filed for detailed
      description of substitutions and preferred embodiments

<400> SEQUENCE: 124

Xaa Tyr Xaa Cys Xaa Xaa Trp Xaa Xaa Xaa Trp Cys Xaa Xaa Val Xaa
1               5                   10                  15

Xaa
```

FC RECEPTOR (FCRN) BINDING PEPTIDES AND USES THEREOF

CROSS-REFERENCE TO RELATED APPLICATIONS

This application is a continuation application under 35 U.S.C. § 120 of co-pending U.S. Ser. No. 16/029,835 filed on Jul. 9, 2018, which is a continuation application under 35 U.S.C. § 120 of U.S. Ser. No. 15/354,375 filed on Nov. 17, 2016 issued as U.S. Pat. No. 10,046,023 on Aug. 14, 2018, which is a continuation application under 35 U.S.C. § 120 of U.S. Ser. No. 14/897,999 filed on Dec. 11, 2015 issued as U.S. Pat. No. 9,527,890 on Dec. 27, 2016, which is a 35 U.S.C. § 371 National Phase Entry Application of International Application No. PCT/US2014/042932 filed Jun. 18, 2014, which designated the U.S., and which claims the benefit under 35 U.S.C. § 119(e) of U.S. Provisional Application No. 61/836,279, filed Jun. 18, 2013, the contents of each of which are incorporated herein by reference in their entireties.

STATEMENT REGARDING FEDERALLY-SPONSORED RESEARCH

This invention was made with government support under Grant No. DK053056 awarded by National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Nov. 14, 2016, is named 043214-077233_SL.txt and is 46,595 bytes in size.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Albumin is a multifunctional transporter of different endogenous as well as exogenous compounds, such as ions, fatty acids, amino acids, hemin, bilirubin and various drugs (Peters, T. Jr. Serum albumin. Adv. Protein Chem. 37, 161-245 (1985)). It is the most abundant protein in blood and thus contributes to maintaining the osmotic pressure. The high serum concentration of albumin is due to the rate of synthesis that takes place in the liver and its interaction with the neonatal Fc receptor, abbreviated FcRn (Chaudhury, C. et al.). The major histocompatibility complex-related Fc receptor for IgG (FcRn) binds albumin and prolongs its lifespan. J. Exp. Med. 197, 315-322 (2003); Anderson, C. L. et al. Perspective-FcRn transports albumin: relevance to immunology and medicine. Trends Immunol. 27, 343-348 (2006). FcRn is a dual binding receptor that, in addition to albumin, binds IgG, and protects both proteins from intracellular degradation and thus plays a key role in prolonging the half-lives of these proteins (Anderson, C. L. et al. Perspective-FcRn transports albumin: relevance to immunology and medicine. Trends Immunol. 27, 343-348 (2006); Roopenian, D. C. & Akilesh, S. FcRn: the neonatal Fc receptor comes of age. Nat. Rev. Immunol. 7, 715-725 (2007); Ward, E. S. & Ober, R. J. Chapter 4: Multitasking by exploitation of intracellular transport functions the many faces of FcRn. Adv. Immunol. 103, 77-115 (2009).

FcRn is a nonclassical major histocompatibility (MHC) class I molecule that consists of a unique transmembrane heavy chain (HC) that is non-covalently associated with the common 02-microglobulin ($\beta$2m). Crystal structures of FcRn show the extracellular part of the HC with an amino-terminal $\alpha$1-$\alpha$2 platform of eight antiparallel $\beta$-pleated strands topped by two long $\alpha$-helices followed by the membrane proximal $\alpha$3-domain (Burmeister, W. P., Huber, A. H. & Bjorkman, P. J. Crystal structure of the complex of rat neonatal Fc receptor with Fc. Nature 372, 379-383 (1994), Burmeister, W. P., Gastinel, L. N., Simister, N. E., Blum, M. L. & Bjorkman, P. J. Crystal structure at 2.2 A resolution of the MHC-related neonatal Fc receptor. Nature 372, 336-343 (1994); West, A. P. Jr. & Bjorkman, P. J. Crystal structure and immunoglobulin G binding properties of the human major histocompatibility complex-related Fc receptor. Biochemistry 39, 9698-9708 (2000)). The 132m unit is tightly bound to residues located below the $\alpha$1-$\alpha$2 platform and to the $\alpha$3-domain. Classical MHC class I molecules bind to short peptides in their peptide-binding groove, located between the two $\alpha$-helices on the $\alpha$1-$\alpha$2 platform but this groove is occluded and empty in FcRn (Burmeister, W. P., Gastinel, L. N., Simister, N. E., Blum, M. L. & Bjorkman, P. J. Crystal structure at 2.2 A resolution of the MHC-related neonatal Fc receptor. Nature 372, 336-343 (1994); West, A. P. Jr. & Bjorkman, P. J. Crystal structure and immunoglobulin G binding properties of the human major histocompatibility complex-related Fc receptor. Biochemistry 39, 9698-9708 (2000)). Instead, the MHC class I fold of FcRn has evolved to bind to IgG and albumin.

FcRn, predominantly localized in acidic endosomal compartments, encounters proteins continuously taken up by fluid-phase endocytosis. The low pH in the vesicles allows ligand binding. FcRn-ligand complexes are then exported to the cell surface, where exposure to the higher physiological pH of the bloodstream triggers release of the ligands by a so-called kiss-and-run exocytotic mechanism (Ward et al. Adv. Immunol. 103: 77-115, 2009; Ober et al., Proc. Natl. Acad. Sci. USA 101:11076-11081, 2004). Proteins that do not bind to FcRn progress to lysosomes for proteolytic degradation.

FcRn plays a role in half-life regulation as demonstrated, e.g., using genetically modified mice, as mice lacking FcRn genetic deficiency of FcRn are both hypoalbuminemic and hypogammaglobulinemic (D C, Robinson J M, et al. Albumin turnover: FcRn-mediate recycling saves as much albumin from degradation as the liver produces. Am J Physiol Gastrointest Liver Physiol. 2005; 290(2): G352-60); Roopenian D C, Christianson G J, Sproule T J, et al. The MHC class I-like IgG receptor controls perinatal IgG transport, IgG homeostasis, and fate of IgG-Fc-coupled drugs. J Immunol. 2003; 170(7):3528-33). A human example is familial hypercatabolic hypoproteinemia, where deficiency in FcRn expression results in abnormally low levels of both ligands. Furthermore, variants of HSA with carboxy-terminal truncations have unusual low serum levels. In line with this, the so-called HSA-Bartin variant, known to lack the C-terminal DIII except for the first 29 amino acids, shows severely reduced FcRn binding.

In some conditions such as acute/subacute toxigenic exposures or chronic conditions where albumin becomes pathogenic due to disease-related modifications, reduction in binding of albumin to FcRn would be beneficial.

SUMMARY OF THE INVENTION

The present disclosure provides novel synthetic peptides that specifically reduce, inhibit or block the interaction between FcRn and albumin. These peptides are useful in increasing the degradation of albumin in conditions, such as acute/subacute toxigenic exposures, such as drug intoxication, or chronic conditions where albumin becomes pathogenic due to disease-related modifications, such as diabetes or kernicterus, or any condition in which decreasing pathologic levels of albumin is desirable.

The invention is based, at least in part, on a finding that a novel isolated, recombinantly produced or synthesized, and optionally purified cyclic disulfide peptide with an amino acid sequence RYFCTKWKHGWCEEVGT (SEQ ID NO: 1) specifically binds to FcRn and blocks its interaction with albumin. Moreover, the inventors found that a dimer of the cyclic peptide, comprising two subunits of the peptide attached to each other via a glycine linker provides another effective way of reducing, inhibiting or blocking the interaction between albumin and FcRn. Specifically important amino acids for binding were identified using an Alanine-scan identified at least the following residues of SEQ ID NO:1 as important for the binding activity of the peptide: Tyr2, Cys4, Trp7, Trp11, Cys12, Val15. Further, structure activity relationship studies also reveal that Gly10, Glu13, Phe3 and Arg1 of SEQ ID NO:1 can contribute to binding.

The invention is also based, at least in part, on a finding that a novel isolated, recombinantly produced or synthesized, and optionally purified cyclic disulfide peptide with an amino acid sequence Ac-AGVMHCFWDEEFKCDQG-GTGGGK-CONH2 (SEQ ID NO:4) or Ac-AGYMTCK-WDDGFSCEYVGTGGGK-CONH2 (SEQ ID NO:5) specifically binds to a non-IgG and non-albumin competitive site on a FCRN alpha 3 domain, thereby enabling the tracking neonatal Fc receptor FCRN without inhibiting IgG or albumin binding or function.

The following embodiments and aspects thereof are described and illustrated in conjunction with compositions and methods which are meant to be exemplary and illustrative, not limiting in scope.

Various embodiments of the present invention provide for an isolated polypeptide that specifically blocks the interaction between neonatal Fc receptor (FCRN) and albumin comprising at least one peptide subunit consisting of an amino acid sequence $X_1$-Y-$X_2$-C-$X_3$-$X_4$-W-$X_5$-$X_6$-$X_7$-W-C-$X_8$-$X_9$-V-$X_{10}$-$X_{11}$ (SEQ ID NO:7), wherein $X_1$, $X_2$, $X_3$, $X_4$, $X_5$, $X_6$, $X_7$, $X_8$, $X_9$, $X_{10}$, and $X_{11}$ is each independently selected from any amino acid, or is deleted.

In various embodiments of the isolated polypeptide, $X_1$ can be R or a conservative amino acid substitution of R, $X_2$ can be F or a conservative amino acid substitution of F, $X_3$ can be T or a conservative amino acid substitution of T, $X_4$ can be K or a conservative amino acid substitution of K, $X_5$ can be H or a conservative amino acid substitution of H, $X_6$ can be G or a conservative amino acid substitution of G, $X_7$ can be C or a conservative amino acid substitution of C, $X_8$ can be E or a conservative amino acid substitution of E, $X_9$ can be E or a conservative amino acid substitution of E, $X_{10}$ can be G, a conservative amino acid substitution of G, or can be deleted, and $X_{11}$ can be T, a conservative amino acid substitution of T, or can be deleted (embodiment disclosed as SEQ ID NO: 9).

In various embodiments of the isolated polypeptide, $X_1$ can be R or a conservative amino acid substitution of R, $X_2$ can be F or a conservative amino acid substitution of F, $X_3$ can be T or a conservative amino acid substitution of T, $X_4$ can be K or a conservative amino acid substitution of K, $X_5$ can be K or a conservative amino acid substitution of K, $X_6$ can be H or a conservative amino acid substitution of H, $X_7$ can be G or a conservative amino acid substitution of G, $X_8$ can be E or a conservative amino acid substitution of E, $X_9$ can be E or a conservative amino acid substitution of E, $X_{10}$ can be G, a conservative amino acid substitution of G, or is deleted, and $X_{11}$ can be T, a conservative amino acid substitution of T, or is deleted (an embodiment disclosed as SEQ ID NO: 124).

In various embodiments of the isolated polypeptide, $X_1$ can be R, and/or $X_2$ can be F (embodiments disclosed as SEQ ID NOS 10-11). In other embodiments of the isolated polypeptide $X_1$ can be R, $X_2$ can be F, $X_7$ can be G, and/or $X_{10}$ can be E (embodiments disclosed as SEQ ID NOS 12-13).

Various embodiments of the present invention provide for an isolated polypeptide that specifically blocks the interaction between neonatal Fc receptor (FCRN) and albumin comprising at least one peptide subunit consisting of an amino acid sequence that is at least 90% identical to RYFCTKWKHGWCEEVGT (SEQ ID NO:1).

In various embodiments of the isolated polypeptide, the at least one peptide subunit can consist of the amino acid sequence set forth in SEQ ID NO:1.

In various embodiments, the isolated polypeptide can comprise two peptide subunits. In other embodiments, the isolated polypeptide can comprise four peptide subunits.

In various embodiments, the peptide subunits can be linked by a linker. In various embodiments, the linker can be a peptide linker comprising 1-10 amino acids. In various embodiments, the linker can be a glycine linker comprising 1-10 glycine residues (SEQ ID NO: 14), or 1-10 glycine and serine residues (SEQ ID NO: 15). In various embodiments, the glycine linker can comprise 3-5 glycine residues (SEQ ID NO: 16), or 3-5 glycine and serine residues (SEQ ID NO: 17). In various embodiments, the linker can be formed from a polyethylene glycol (PEG) H—(O—CH$_2$—CH$_2$)$_n$—OH, wherein n is an integer from 2-12.

In various embodiments, the peptide subunit can be a cyclic peptide.

In various embodiments, the isolated polypeptide can comprise at least one amino acid analog or amino acid mimetic. In various embodiments, the isolated polypeptide can comprise a modified peptide backbone. In various embodiments, the isolated polypeptide can comprise a hydrophilic unstructured polymer. In various embodiments, the hydrophilic unstructured polymer is an extended recombinant polypeptide. In various embodiments, the isolated polypeptide can comprise polyethylene glycol (PEG). In various embodiments, the isolated polypeptide can be acetylated. In various embodiments, the isolated polypeptide can further comprise at least one second protein or peptide to form a fusion peptide. In various embodiments, the at least second peptide or protein can comprise an epitope tag or a half-life extender or both.

Various embodiments of the present invention provide for a composition comprising an isolated polypeptide that specifically blocks the interaction between neonatal Fc receptor (FCRN) and albumin of the present invention. In various embodiments, the composition can further comprise a pharmaceutically acceptable carrier.

Various embodiments of the present invention provide for a nucleic acid encoding an isolated polypeptide that specifically blocks the interaction between neonatal Fc receptor (FCRN) and albumin of the present invention.

Various embodiments of the present invention provide for a vector comprising a nucleic acid encoding an isolated polypeptide that specifically blocks the interaction between neonatal Fc receptor (FCRN) and albumin.

Various embodiments of the present invention provide for a cell comprising the nucleic acid encoding an isolated polypeptide that specifically blocks the interaction between neonatal Fc receptor (FCRN) and albumin or the vector comprising a nucleic acid encoding the an isolated polypeptide that specifically blocks the interaction between neonatal Fc receptor (FCRN) and albumin.

Various embodiments of the present invention provide for a method of blocking the interaction of neonatal Fc receptor (FCRN) and albumin comprising contacting an isolated polypeptide of the present invention with a system comprising neonatal Fc receptor (FCRN) and albumin.

Various embodiments of the present invention provide for a method of blocking the interaction between neonatal Fc receptor (FCRN) and albumin in a subject in need thereof, the method comprises administering a polypeptide of the present invention, or the composition of the present invention to the subject.

In various embodiments, blocking the interaction between neonatal Fc receptor (FcRn) and albumin can decrease albumin level in the subject. In various embodiments, blocking the interaction between neonatal Fc receptor (FcRn) and albumin can treat a disease or condition caused by increased amount of albumin. In various embodiments, the disease or condition treated can be acute toxigenic exposure or sub-acute toxigenic exposure to a drug. In various embodiments, the disease or condition treated can be selected from the group consisting of metabolic disorder, neurological disorder, endocrinologic disorder, cardiovascular diseases, ophthalmologic disease, peripheral vascular disease, renal disease, liver or gastrointestinal disease, infectious disease associated with virus, bacterium, or mycobacterium, and chronic inflammation or toxigenic condition from any cause in which elevated levels of albumin or pathogenic albumin conjugates are desired to be lowered. In various embodiments, the metabolic disorder can be metabolic syndrome, diabetes mellitus, or hyperthyroidism; the neurological disorder can be kernicterus, neuropathy or Alzheimer's disease; the cardiovascular disease can be atherosclerosis; the ophthalmologic disease can be cataracts and retinopathy; the renal disease can be glomerulonephritis; the infectious disease can be associated with HIV or viral hepatitis; the infectious disease is associated with tuberculosis.

Various embodiment of the present invention provide for a use of an isolated polypeptide of the present invention or a composition of the present invention for treating a disease or condition caused by increased amount of albumin, such as acute toxigenic exposure or sub-acute toxigenic exposure to a drug toxin, diabetes, metabolic disorders such as metabolic syndrome, diabetes mellitus, and hyperthyroidism, neurological disorders such as kernicterus, neuropathy or Alzheimer's disease, cardiovascular diseases such as atherosclerosis, ophthalmologic diseases such as cataracts and retinopathy, peripheral vascular disease, renal disease such as glomerulonephritis, infectious diseases associated with viruses such as HIV and viral hepatitis, bacteria, mycobacteria such as tuberculosis, chronic inflammation from any cause in which elevated levels of albumin or pathogenic albumin conjugates are desired to be lowered.

Various embodiments of the present invention provide for an isolated polypeptide capable of binding to a non-IgG and non-albumin competitive site on a FCRN alpha 3 domain comprising at least one peptide subunit consisting of an amino acid sequence AGVMHCFWDEEFKCDQG-GTGGGK (SEQ ID NO:4), with up to four amino acid substitutions and/or up to eight amino acid deletions.

In various embodiments of the isolated polypeptide, the up to four amino acid substitutions are in residues 3-17 of SEQ ID NO:4. In various embodiments of the isolated polypeptide, the at least one of the up to four amino acid substitutions can be a conservative amino acid substitution. In various embodiments of the isolated polypeptide, the up to eight amino acid deletions can be selected from residues 1, 2, 18, 19, 20, 21, 22, or 23 of SEQ ID NO:4. In various embodiments of the isolated polypeptide, the at least one peptide subunit can consist of an amino acid sequence as set forth in SEQ ID NO:4.

Various embodiments of the present invention provide for an isolated polypeptide capable of binding to a non-IgG and non-albumin competitive site on a FCRN alpha 3 domain comprising at least one peptide consisting of an amino acid sequence that is at least 73% identical to residues 3-17 of AGVMHCFWDEEFKCDQGGTGGGK (SEQ ID NO:4).

Various embodiments of the present invention provide for an isolated polypeptide capable of binding to a non-IgG and non-albumin competitive site on a FCRN alpha 3 domain comprising at least one peptide subunit consisting of an amino acid sequence AGYMTCKWDDGFSC-EYVGTGGGK (SEQ ID NO: 5) with up to three amino acid substitutions and/or up to eight amino acid deletions.

In various embodiments of the isolated polypeptide, the up to three amino acid substitutions or deletions can be in residues 3-17 of SEQ ID NO:5. In various embodiments of the isolated polypeptide, the at least one of the up to three amino acid substitutions can be a conservative amino acid substitution. In various embodiments of the isolated polypeptide, the up to eight amino acid deletions can be selected from residues 1, 2, 18, 19, 20, 21, 22 or 23. In various embodiments of the isolated polypeptide, the at least one peptide subunit can consist of an amino acid sequence as set forth in SEQ ID NO: 5.

Various embodiments of the present invention provide for an isolated polypeptide capable of binding to a non-IgG and non-albumin competitive site on a FCRN alpha 3 domain comprising at least one peptide subunit consisting of an amino acid sequence at least 80% identical to residues 3-17 of AGYMTCKWDDGFSCEYVGTGGGK (SEQ ID NO: 5).

Various embodiments of the present invention provide for an isolated polypeptide capable of binding to a non-IgG and non-albumin competitive site on a FCRN alpha 3 domain comprising at least one peptide subunit consisting of an amino acid sequence AGVMKCWWDEEMLCRAF-GTGGGK (SEQ ID NO:6) with up to two amino acid substitutions and/or up to eight amino acid deletions.

In various embodiments of the isolated polypeptide, the up to two amino acid substitutions can be in residues 3-17 of SEQ ID NO:6. In various embodiments of the isolated polypeptide, at least one of the up to two amino acid substitutions can be a conservative amino acid substitution. In various embodiments of the isolated polypeptide, the up to eight amino acid deletions can be selected from residues 1, 2, 18, 19, 20, 21, 22, or 23. In various embodiments of the isolated polypeptide, the at least one peptide subunit can consist of an amino acid sequence as set forth in SEQ ID NO: 6.

Various embodiments of the present invention provide for an isolated polypeptide capable of binding to a non-IgG and non-albumin competitive site on a FCRN alpha 3 domain, comprising at least one peptide subunit consisting of an amino acid sequence at least 86% identical to residues 3-17 of AGVMKCWWDEEMLCRAFGTGGGK (SEQ ID NO: 6).

Various embodiments of the present invention provide for an isolated polypeptide capable of binding to a non-IgG and non-albumin competitive site on a FCRN alpha 3 domain, comprising at least one peptide subunit consisting of an amino acid sequence identical to residues 3-17 of AGVM-KCWWDEEMLCRAFGTGGGK (SEQ ID NO: 6).

In various embodiments, the isolated polypeptide can comprise two peptide subunits. In various embodiments, the isolated polypeptide can comprise four peptide subunits.

In various embodiments, the peptide subunits can be linked by a linker. In various embodiments, the linker can be a peptide linker comprising 1-10 amino acids. In various embodiments, the linker can be a glycine linker comprising 1-10 glycine and/or serine residues (SEQ ID NOS 14-15). In various embodiments, the glycine linker can comprise 3-5 glycine and/or serine residues (SEQ ID NOS 16-17). In various embodiments, the linker can be formed from a polyethylene glycol (PEG) H—(O—CH$_2$—CH$_2$)$_n$—OH, wherein n is an integer from 2-12.

In various embodiments of the isolated polypeptide, the peptide subunit can be a cyclic peptide. In various embodiments of the isolated polypeptide, can comprise at least one amino acid analog or amino acid mimetic. In various embodiments, the isolated polypeptide can comprise a modified peptide backbone. In various embodiments, isolated polypeptide can comprise a hydrophilic unstructured polymer. In various embodiments, the hydrophilic unstructured polymer can be an extended recombinant polypeptide. In various embodiments, the isolated polypeptide can comprise polyethylene glycol (PEG). In various embodiments, the isolated polypeptide can be acetylated. In various embodiments, the isolated polypeptide can further comprise at least one second protein or peptide to form a fusion peptide. In various embodiments, the at least second peptide or protein can comprises an epitope tag or a half-life extender or both.

Various embodiments of the present invention provide for a composition comprising an isolated polypeptide capable of binding to a non-IgG and non-albumin competitive site on a FCRN alpha 3 domain of the present invention. In various embodiments, the composition can comprise a pharmaceutically acceptable carrier.

Various embodiments of the present invention provide for a nucleic acid encoding an isolated polypeptide capable of binding to a non-IgG and non-albumin competitive site on a FCRN alpha 3 domain of the present invention.

Various embodiments of the present invention provide for a vector comprising the nucleic acid encoding an isolated polypeptide capable of binding to a non-IgG and non-albumin competitive site on a FCRN alpha 3 domain of the present invention.

Various embodiments of the present invention provide for cell comprising the nucleic acid encoding an isolated polypeptide capable of binding to a non-IgG and non-albumin competitive site on a FCRN alpha 3 domain of the present invention, or the vector comprising a nucleic acid encoding an isolated polypeptide capable of binding to a non-IgG and non-albumin competitive site on a FCRN alpha 3 domain of the present invention.

Various embodiments of the present invention provide for a method of tracking neonatal Fc receptor (FCRN) without inhibiting IgG or albumin binding or function, comprising: contacting a system comprising FCRN with an isolated polypeptide capable of binding to a non-IgG and non-albumin competitive site on a FCRN alpha 3 domain of the present invention, wherein the isolated polypeptide further comprises a label to produce a signal; and tracking FCRN by detecting the signal. In various embodiments, the tracking is performed in vivo.

Various embodiments of the present invention provide for a use of an isolated polypeptide capable of binding to a non-IgG and non-albumin competitive site on a FCRN alpha 3 domain of the present invention, or the composition comprising an isolated polypeptide capable of binding to a non-IgG and non-albumin competitive site on a FCRN alpha 3 domain of the present invention for tracking neonatal Fc receptor (FCRN) without inhibiting IgG or albumin binding or function.

Various embodiments of the present invention are also based, at least in part, on a finding that certain residues on human serum albumin are relevant to FCRN binding. These residues include Glu565, Asn111 or Asn109 of SEQ ID NO:8 (sequence of human serum albumin).

A structural model of the complex model between the human neonatal Fc receptor (hFcRn) and human serum albumin (HSA) was enabled and generated using the program ZDOCK (Pierce B G, Hourai Y, Weng Z. (2011) *Accelerating Protein Docking in ZDOCK Using an Advanced 3D Convolution Library*. PLoS One 6(9): e24657) based upon the docking interactions between SYN1753 and hFcRn (FIG. 10A) and using the structural model hFcRn:SYN1753 and a previously published HSA structural model (PDB ID 1BM0) for the search. The program was run with selected residues from both structures in agreement with knowledge regarding binding and the relevant residues for peptide binding. For generation of the docking solutions, residues Leu122, Thr153 and His161 in hFcRn and residues His464, His510 and His535 in HSA were selected as relevant contacts in the protein-protein binding interface. The best solution reveals that the pair of peptides SYN1753 binds hFcRn at the same binding site as domain DIII of HSA (amino acids 404-601 of SEQ ID NO:8). One of the peptides, SYN1753, from the bound pair overlaps partly with the recognition loop in the region between residues 508 and 517 in HAS, whereas the other overlaps partly with the recognition loop between residues 502 and 509 in HSA. Regarding critical residues in HSA for the interaction with hFcRn, in addition to Lys500, His464, His510, His535, Glu531 which were previously identified by Andersen and colleagues (Nature Communications 2011), our model predicts that Glu565, Asn111 and Asn109 in HSA are also relevant for FcRn binding (FIG. 10B). This model predicts that critical residues in hFcRn for the interaction with HSA include, in addition to Glu54, Asp101, Phe157, His161, His166 and Glu168 (as identified by Andersen and colleagues, Nature Communications 2011), Thr153, Asn149, Leu122, Leu156, Gln56 and Ser104 as identified herein.

The inventors found that Glu565, Asn111 and Asn109 in human serum albumin (HSA) are residues critical to human FcRn binding such that their modification will allow creation of gain-of-function (increased binding) and loss-of-function (decreased binding) versions of HSA.

Accordingly, various embodiments of the present invention provide for a method of screening for loss or gain of function mutations in human serum albumin (HSA) comprising: providing a mutant protein comprising SEQ ID NO:8, wherein one or more amino acids selected from Glu565, Asn111 or Asn109 have been mutated to any other amino acid or an amino acid analog; contacting the mutant protein with human FcRn; detecting binding affinity of the human FcRn with the mutant protein; comparing the binding activity of the mutant protein to human FcRn to binding activity of the wild-type protein comprising SEQ ID NO: 8 to human FcRn; identifying a loss of function mutation when the binding activity of the mutant protein is decreased or abolished compared to the wild-type protein and identifying a gain of function mutation when the binding activity of the mutant protein is increased compared to the wild type protein. In various embodiments, the method can further comprise mutating one or more of the residues selected from Glu565, Asn111 and Asn109 of SEQ ID NO: 8. Detecting the affinity can be performed, for example, surface plasmon resonance, X-ray crystallography, nuclear magnetic resonance spectroscopy, size-exclusion or affinity chromatography, isothermal titration calorimetry, affinity electrophoresis, Bio-Layer Interferometry, dual polarization interferometry (DPI), fluorescence polarization/anisotropy, fluorescence correlation spectroscopy, or fluorescence correlation spectroscopy. In certain embodiments, the steps of comparing and identifying can be performed by a non-human machine.

Various embodiments of the invention provide for a human serum albumin (HSA) derivative comprising one or more amino acid or amino acid analog substitutions at Glu565, Asn111 or Asn109 of SEQ ID NO:8.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

(FIG. 2A) One subunit of FcRn represented as a ribbon diagram with β2-microglobulin colored in dark gray and FcRn colored in medium gray. The bound peptides as a pair (SYN1753) are represented as ball-and-stick with backbones in dark gray and medium gray. (FIG. 2B) Closer view of the interaction between the peptide pair (SYN1753) and the FcRn molecule.

FIG. 3A depicts both SYN1753 peptides centered around FcRn residues Phe157, Leu156, His161. FIG. 3B depicts a representation of the interactions between SYN1753 peptides and FcRn. H-bonds between each SYN1753 peptide and within each peptide are represented as black dashes, although exact H-bonding is limited due to low resolution (3.2 A). N and C-termini of both peptides are in very close proximity, which suggests that a continuous dimer sequence may be a better, more optimized peptide. Given the likely importance of His161 in FcRn to albumin binding, it is predicted that His161 in FcRn is responsible for pH dependent binding of SYN1753.

FIG. 4 discloses SEQ ID NO: 120.

FIG. 6 discloses SEQ ID NO: 121.

FIGS. 7A-7B show that decreased cross-linking suggests that the unlabeled peptide competes for the SYN653 (571) binding site. sh-FcRn was incubated with 10 or 100 eq of phage peptides SYN571, 572, 530, 605, 620, 531, 596 (=516), or no peptide. After 1 hour (RT, dark), 1 eq of SYN653 was added (=Biotin-Bpa-571). After 30 min (RT, dark), irradiated for 30 min (365 nm, on ice). 1 ug was run on 4-20% SDS-PAGE, transferred to nitrocellulose and visualized biotinylated protein with ECL Plus Reagents. FIG. 7C depicts densitometry: Relative % Cross-linking of SYN653 in presence (or absence) of phage peptide. The y-axis is the relative % cross-linking efficiency of all peptides, as compared to the cross-linking efficiency of SYN653 which was set at 100%.

FIG. 8B discloses SEQ ID NOS 122 and 18, respectively, in order of appearance.

FIG. 10A shows a cartoon representation with FcRn colored in medium gray bound to β2-microglobulin colored in dark gray and HSA colored with hatching pattern with the N-termini and C-termini labelled. Peptides SYN1753 represented in dotted lines cartoon and solid line cartoon. FIG. 10B shows a cartoon representation of HSA:FcRn highlighting relevant residues for the interactions predicted by this model (HSA residues in hatching pattern and solid outline; new HSA residues predicted by this model in dotted outline; FcRn residues in shades of medium to dark gray with the novel residues in light gray).

FIGS. 12A-12E shows that genetic deletion or blockade of FcRn-albumin interactions decreases chemical-induced liver toxicity. FIG. 12A depicts transcytosis of human albumin in MDCK II cells expressing hFcRn and hβ2m in the presence of ADM31 or isotype control (n=3, *, P<0.001). FIG. 12B depicts survival curves after administration of a lethal dose of APAP and either ADM31 or isotype control (n=4 (hFCGRT$^{TG}$), 14 (Fcgrt$^{-/-}$), 10 (hFCGRT$^{TG}$+ADM31), 9 (hFCGRT$^{TG}$+Isotype control), P=0.0002). FIG. 12C depicts transcytosis of human albumin in MDCK II cells co-expressing hFcRn and hβ2m in the presence of SYN1753, SYN3258 or a scrambled peptide control (n=3 per group, , P<0.01, *, P<0.001). FIGS. 12D-12E depict serum ALT levels and survival curve after a lethal dose of APAP in mice receiving a continuous dose of peptides via i.p. osmotic pump (n=6 per group, , P<0.01, P=0.1788). Data analysis by Mantel-Cox test (FIG. 12B, 12E), 2-way ANOVA with Bonferroni post-hoc test (FIG. 12A, 12C), or unpaired Student t-test (FIG. 12D).

FIG. 13A depicts a ribbon diagram of the x-ray structure of FcRn and the SYN1753 dimer. FcRn (medium gray) is bound to β2-microglobulin (dark gray) with SYN1753 peptide dimer represented as light gray spheres and medium gray outlined spheres. FIG. 13B depicts shared interactions between both peptides of the SYN1753 dimer and FcRn centered around FcRn residues Phe157, Leu156, His161 (side chains shown as light gray spheres). FIG. 13C depicts magnification of the SYN1753 peptide dimer (in sticks) with corresponding electron density map (2Fo-Fc) contoured at 1.0 sigma. FIG. 13D depicts a representation of the binding of paired SYN1753 peptides on the FcRn surface around Leu156, Phe157 and His161 (left panel) and the possible connection by a short flexible linker (circles) between the peptides (right panel). FIG. 13E depicts: Left panel: X-ray structures of FcRn:HSA (PDB ID 4K71) and FcRn:SYN1753 (PDB ID 4PVW). FcRn (medium gray) bound to β2-microglobulin (dark gray) and HSA (hatching pattern). SYN1753 peptides (arrows, dotted outlined light gray spheres and black outlined medium gray spheres). Middle panel: HSA:FcRn structure (PDB ID 4K71) highlighting relevant residues for the interactions between these molecules and FcRn and the SYN1753 dimer. FcRn from model FcRn:SYN1753 (medium gray) superposed to FcRn (PDB ID 4K71) (light gray); HSA (PDB ID 4K71) (hatching pattern); peptides SYN1753 (outlined and black ribbons). Residues sharing hydrogen bonds are represented in spheres and shaded according to each structural model. Right panel: Magnification of the SYN1753 dimer binding region relative to the position of HSA in the HSA:FcRn structure (PDB ID 4K71).

DESCRIPTION OF THE INVENTION

The invention described herein is based, at least in part, on the discovery that polypeptides named "SYN1753" and "SYN3258" are capable of specifically blocking the interaction between FcRn and albumin. "SYN1753" polypeptide refers to a polypeptide having the sequence Ac-RYFCTK-WKHGWCEEVGT-CONH2 (SEQ ID NO:1). In some aspects, analogs, derivatives, or fragments thereof can be used. "SYN3258" polypeptide refers to a polypeptide having the sequence Ac-RYFCTKWKHGWCEEVGT-GGG-RYFCTKWKHGWCEEVGT-CONH2 (SEQ ID NO:2). In some aspects, analogs, derivatives, or fragments thereof can also be used. "SYN1753" was identified as the core sequence of "SYN571" by examination of the structure activity relationship. "SYN571" polypeptide refers to a polypeptide having the sequence Ac-AGRYFCTKWKHG-WCEEVGTGGGK-CONH2 (SEQ ID NO:3).

Figure 3A:
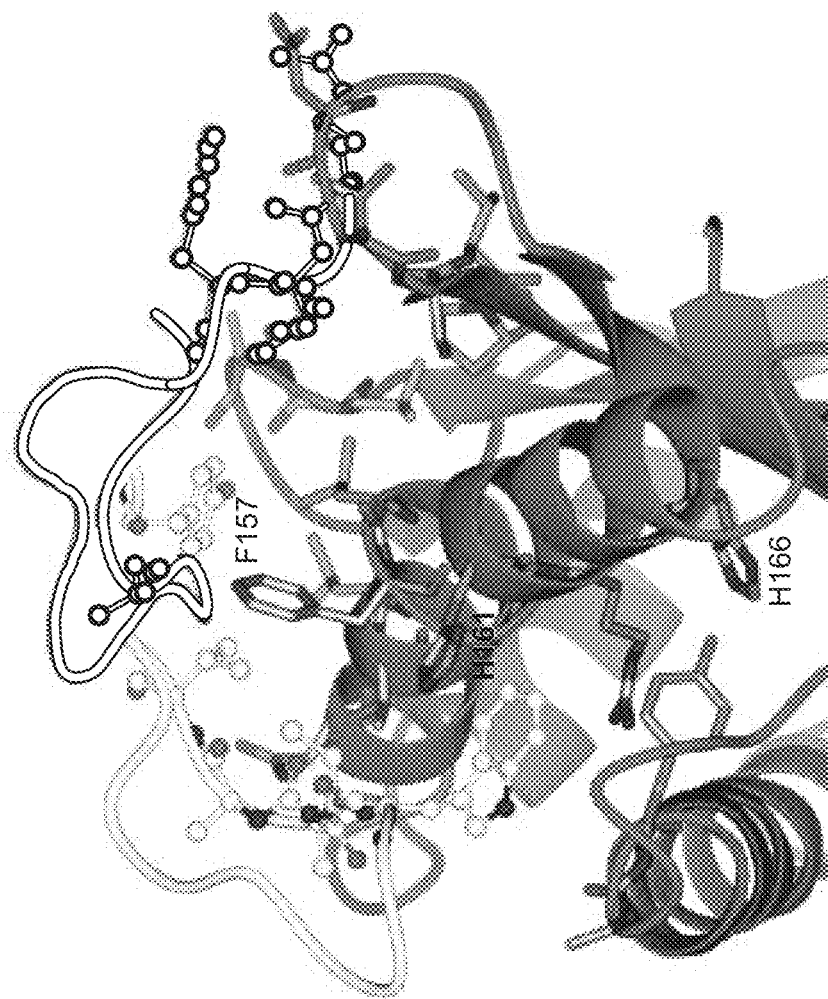
FIGS. 3A-3B depict X-ray crystallography of albumin blocking peptide (SYN1753) docking sites with FcRn.
Figure 3B:
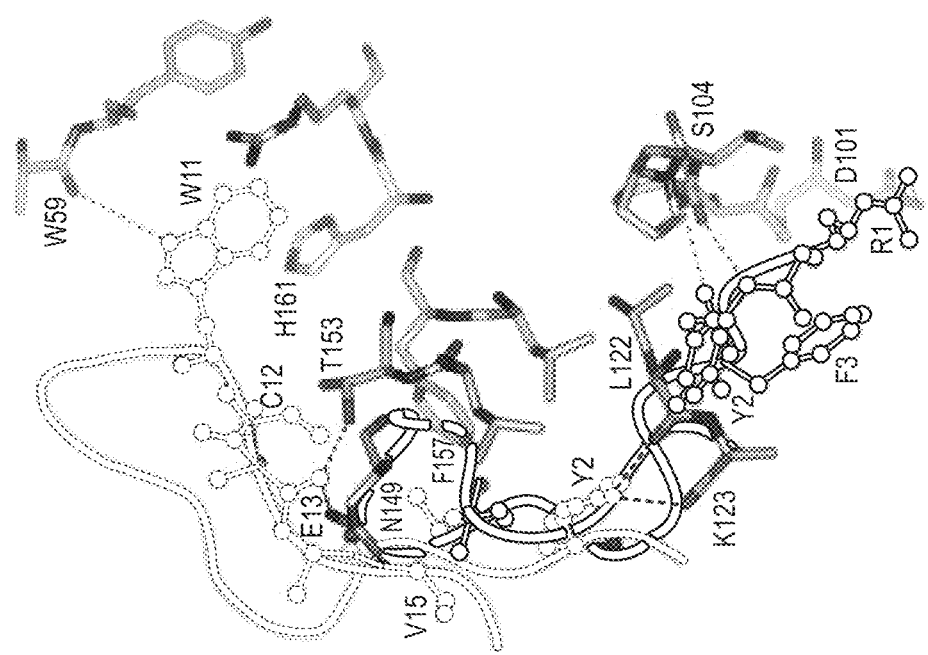
Figure 4:
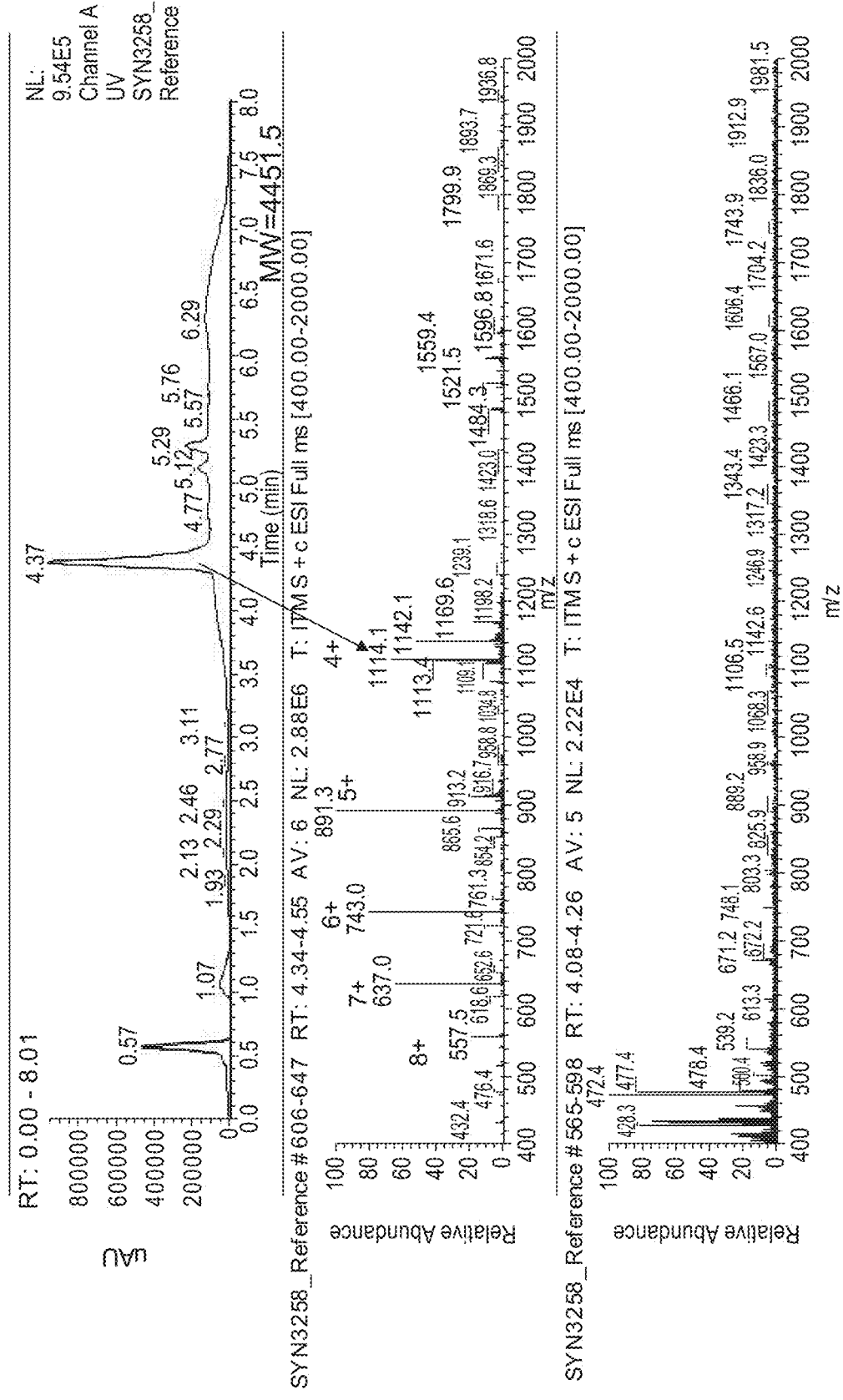
FIG. 4 depicts the stability of SYN3258 in Mouse Plasma: LC-UV-MS of SYN3258 (10 µg/mL) standard.
Figure 5:
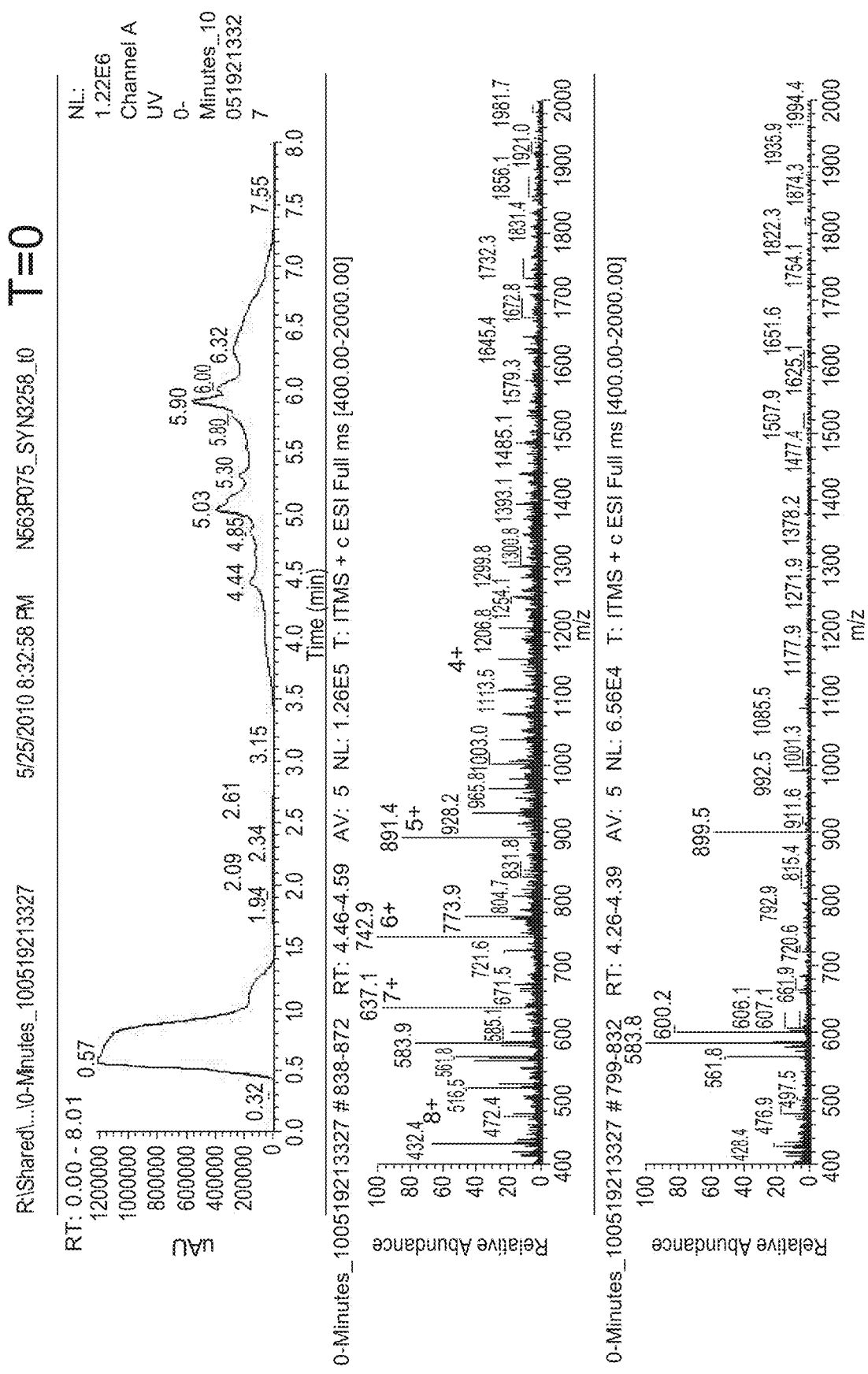
FIG. 5 depicts LC-UV-MS of SYN3258 plasma stability sample T=0.
Figure 6:
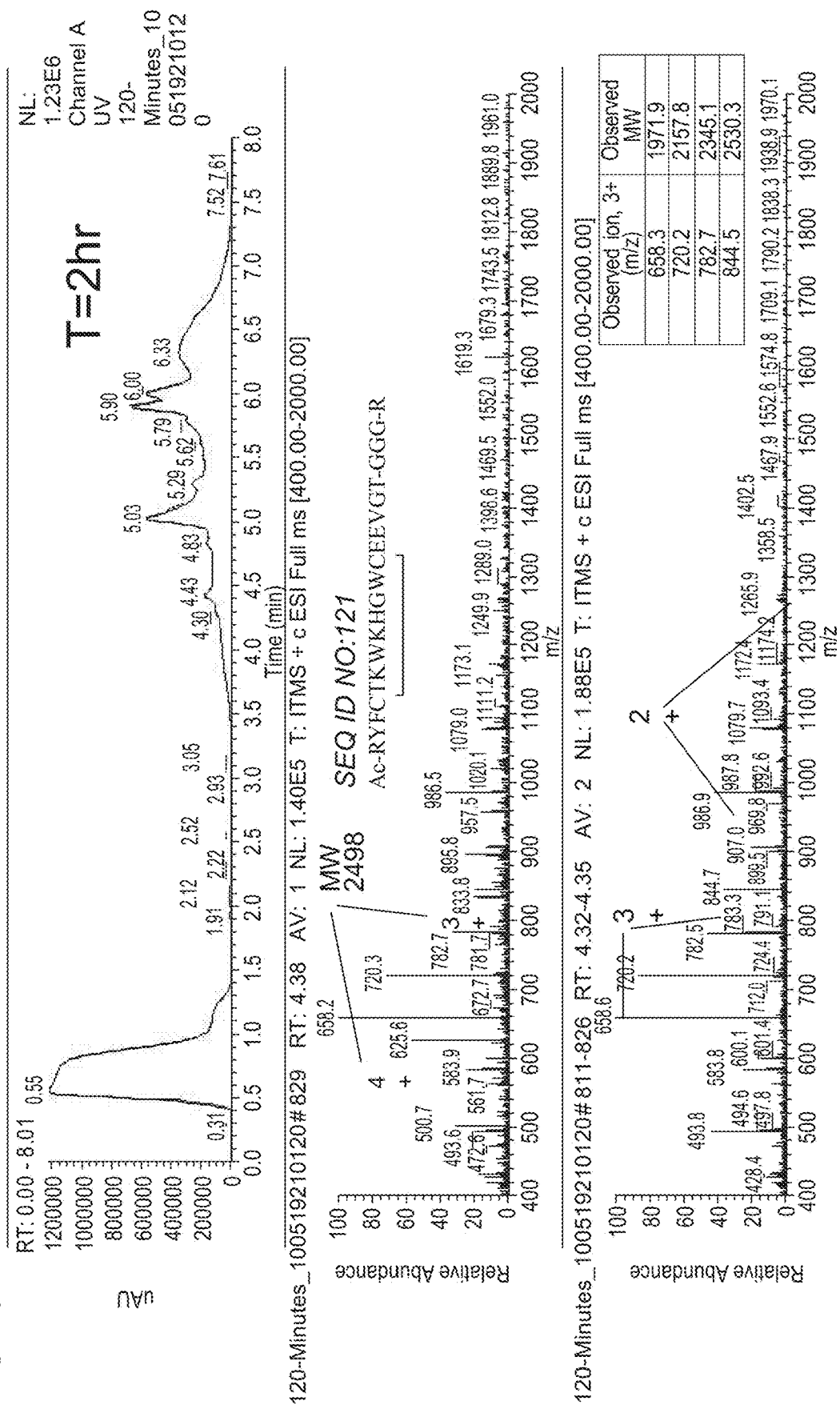
FIG. 6 depicts LC-UV-MS of SYN3258 plasma stability sample T=2 h.
Figure 7A:
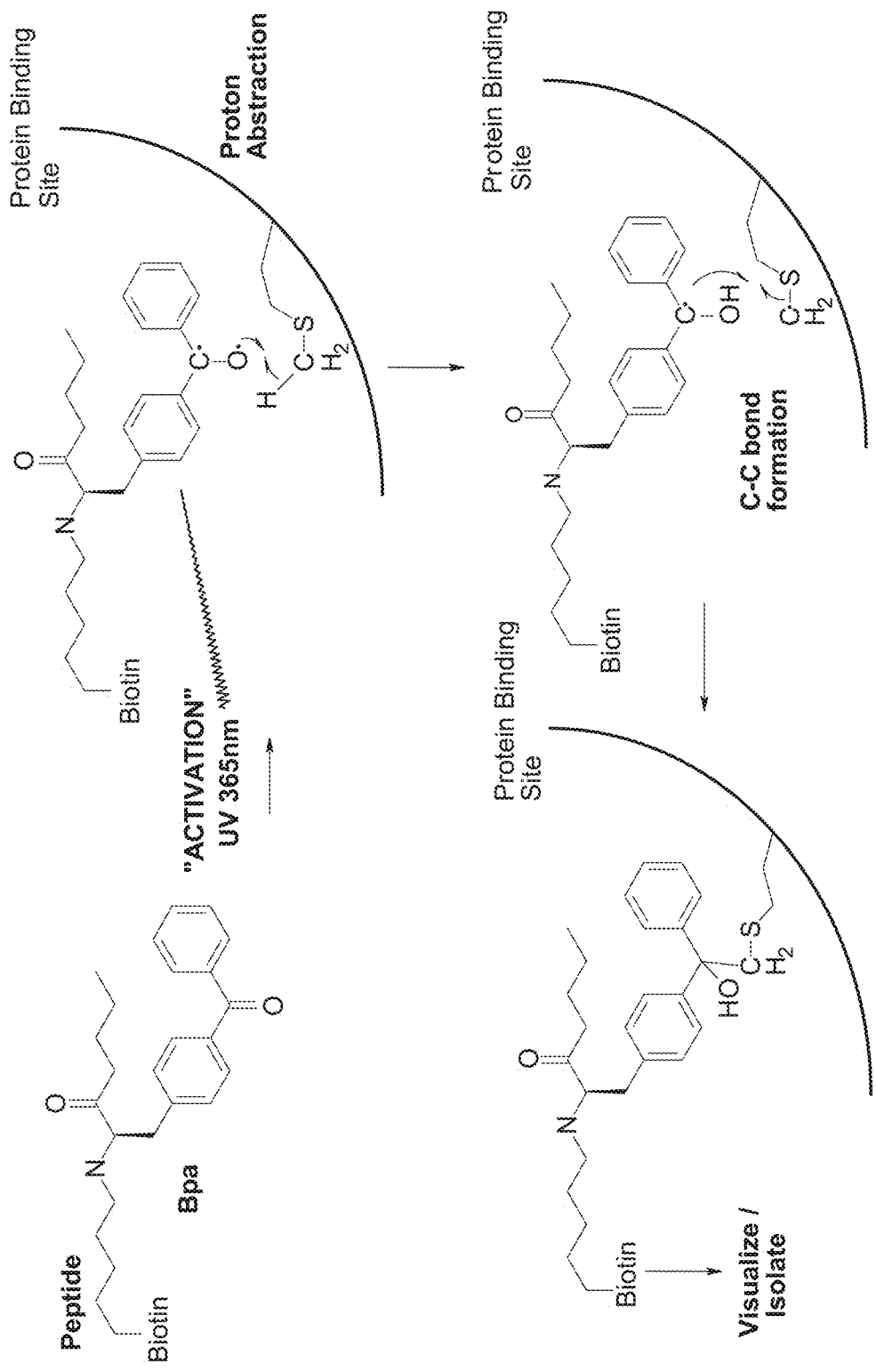
FIGS. 7A-7C demonstrate the function of SYN653.
Figure 7B:
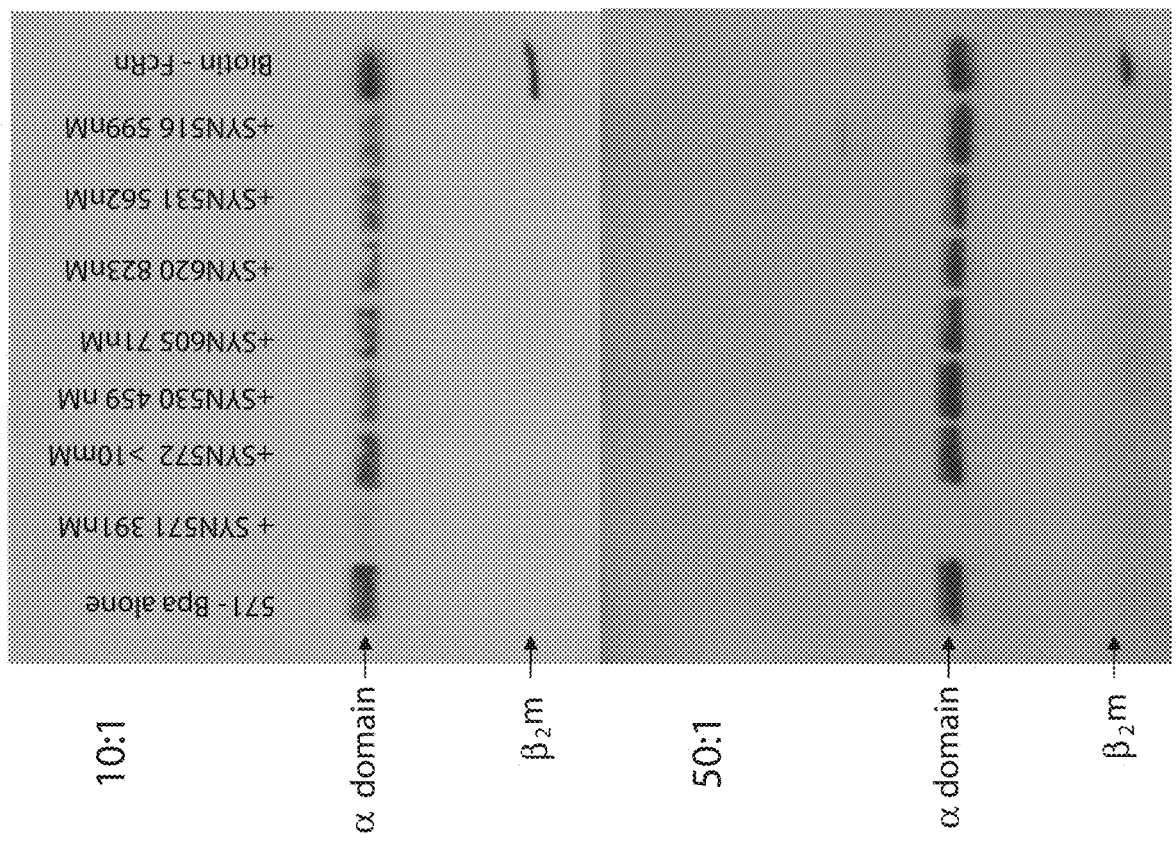
Figure 7C:
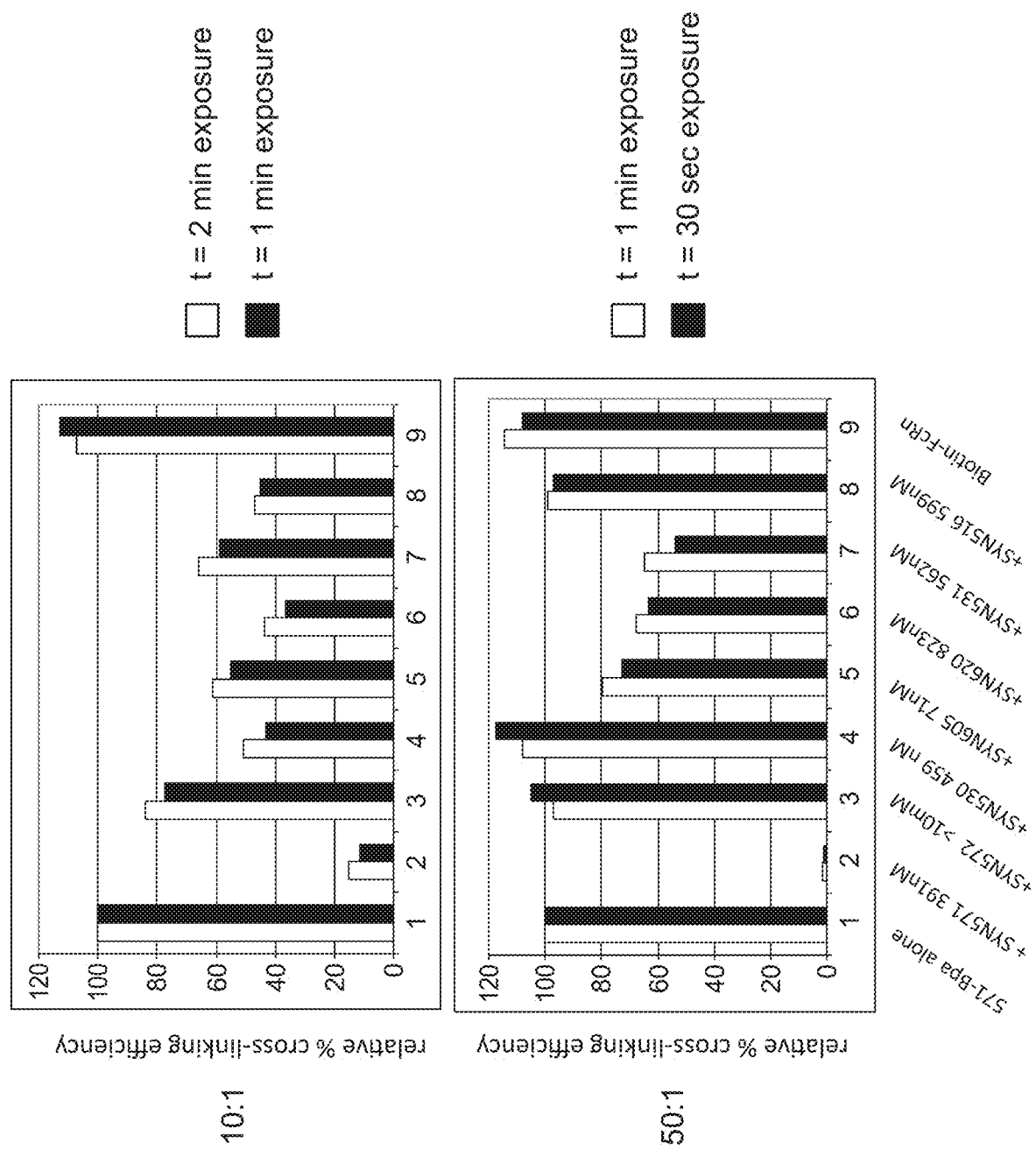
Figure 8A:
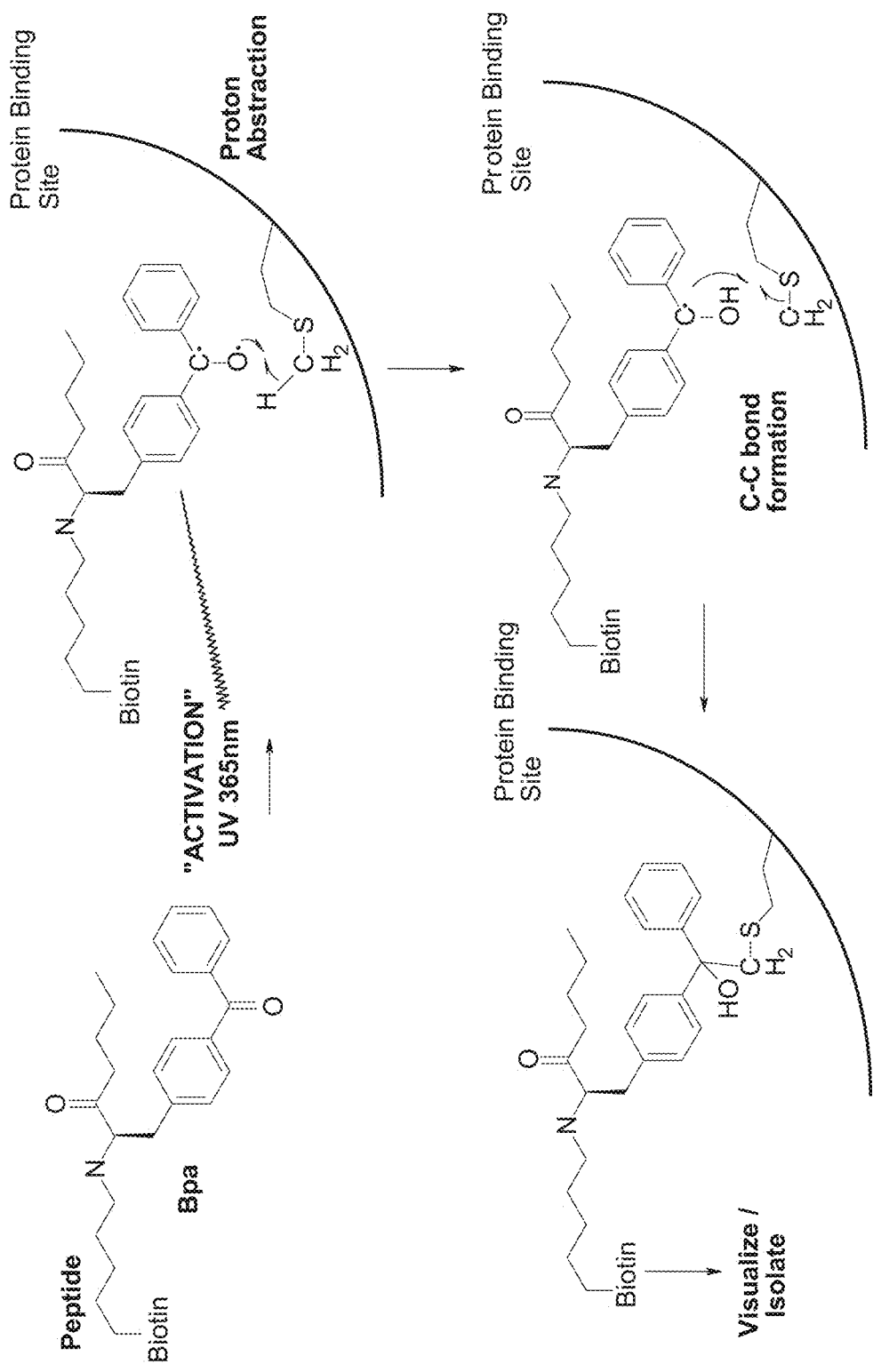
FIGS. 8A-8B show that decreased cross-linking suggests that the unlabeled peptide/antibody competes for the cross-linking peptide's binding site. sh-FcRn was incubated with 100 eq of phage peptides or 10 eq of 3B3.11, or no peptide. After 30 min (RT, dark), 2 eq of cross-linking peptide was added. After 30 min (RT, dark), irradiated for 30 min (365 nm, on ice). 1 ug was run on 4-20% SDS-PAGE, transferred to nitrocellulose and visualized biotinylated protein with ECL Plus Reagents.
Figure 8B:
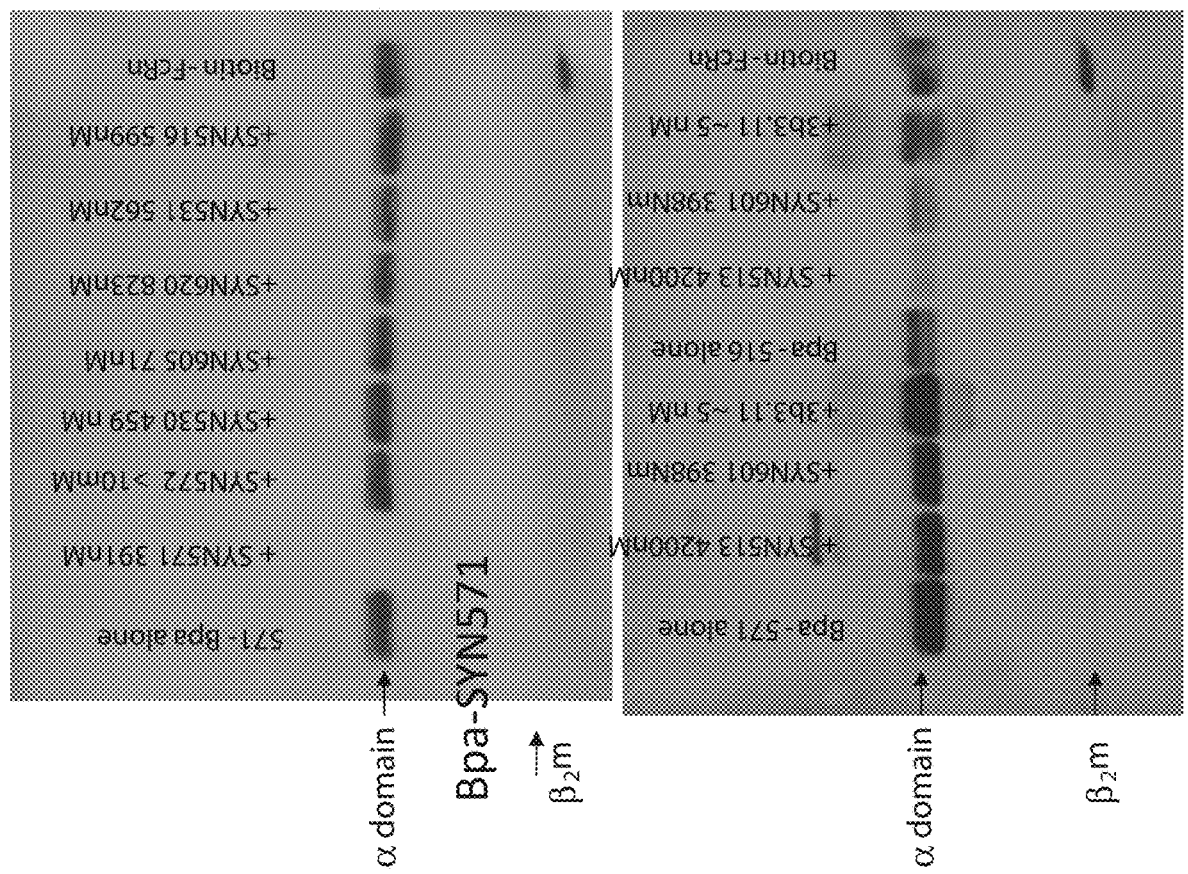
Figure 8B:
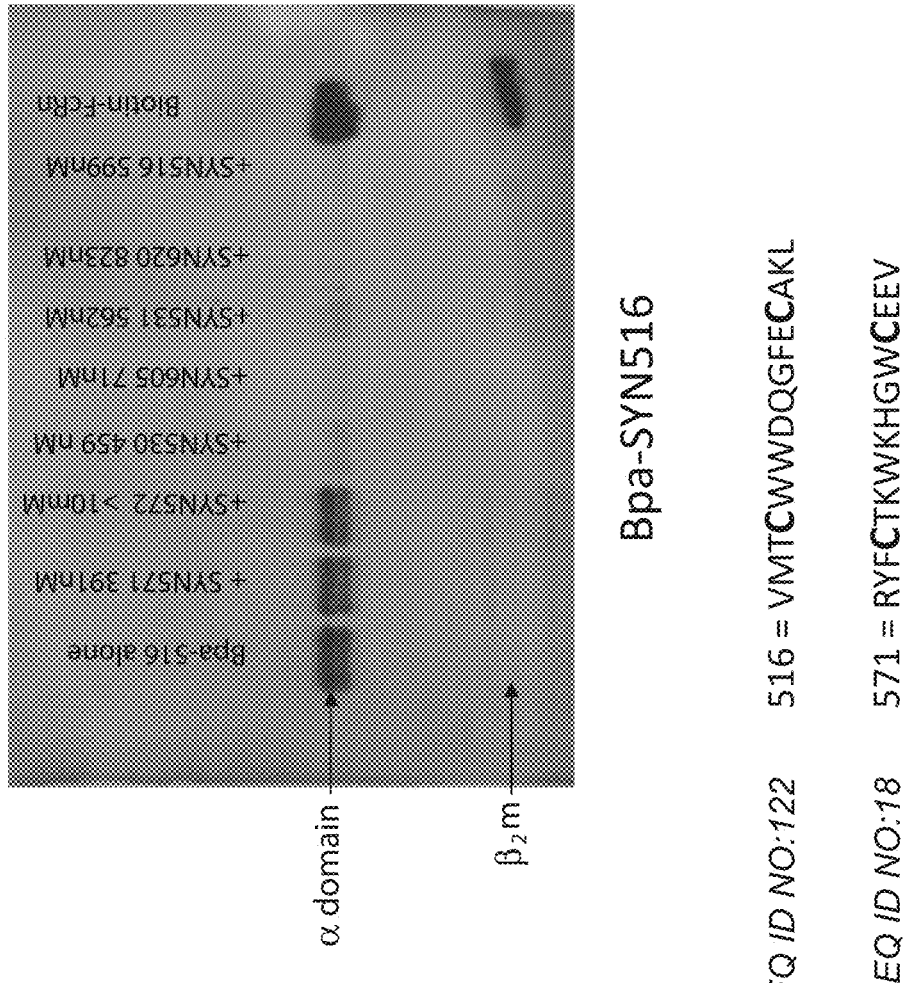

SYN1753 was co-crystallized with soluble human FcRn and demonstrated that the peptide formed a dimer in complex with a single FcRn molecule and defined albumin binding epitopes in a pocket on FcRn that centered around several previously identified contact residues on FcRn for albumin; namely, Phe157, His161 and His166. The N and C termini of the two bound peptides were in close proximity in the X-ray crystal structure suggesting that a covalent peptide dimer may represent a more optimized peptide to sufficiently block the albumin binding pocket (FIG. 3). Generation of a dimeric peptide was accomplished by fusing two SYN1753 peptides to create SYN3258 (Ac-[SYN1753]-GGG-[SYN1753]-CONH2, a 37 mer (SEQ ID NO:2)) that exhibited a higher affinity for FcRn by SPR (3.6 nM at pH 6.0) as compared to the monomeric peptide SYN1753 (~500 nM at pH 6.0).

Although FcRn is well known to be the major factor responsible for high concentrations and long half-life of albumin in circulation, little is known concerning the mechanisms by which these are accomplished. Current models are extrapolated largely from studies of serum pharmacokinetics attributed to FcRn recycling and trafficking of IgG across epithelial and vascular endothelial barriers. Similarly, after fluid phase pinocytosis and binding to FcRn in acidic endosomes, albumin is proposed to be recycled and diverted from a degradative fate in lysosomes. However, neither this process nor the cell type(s) responsible in vivo have been directly demonstrated for albumin, making it unclear how albumin homeostasis is actually achieved. We now demonstrate that liver hepatocytes, which are the source of albumin synthesis and a major site of FcRn expression, play an unexpected role in albumin homeostasis through mechanisms all of which are seemingly focused on the vascular system abutting the basal (sinusoidal) hepatocyte surface. In this manner the enormous synthetic function of the liver is predicted to be optimized for the maintenance of this critical serum protein. In the absence of FcRn, these mechanisms are lost and albumin excretion into the bile is observed despite hypoalbuminemia in the serum. This interestingly operates against a concentration gradient resulting in a protein losing biliopathy that is specific not only for albumin but also for IgG, the other known FcRn ligand.

Further, and most strikingly, we provide direct evidence that these physiologic functions are amenable to therapeutic manipulation such that blockade of albumin-FcRn interactions can be achieved without collateral effects on IgG homeostasis. In contrast to current efforts which are focused on preserving and enhancing FcRn-albumin interactions for the intentions of half-life extension of therapeutic agents, our studies directly demonstrate that contrary therapeutic goal—blockade of albumin-FcRn interactions can be achieved without collateral effects on IgG homeostasis. Specifically, purposeful blockade of albumin-FcRn interactions that promotes albumin loss represents a unique therapeutic avenue for protection against the effects of toxic or potentially otherwise pathogenic forms of albumin in a number of diseases. Although we show this in models of drug-induced toxicity, it is expected that such therapeutic approaches as demonstrated herein extend to other situations where albumin takes on pathogenic characteristics as observed in metabolic diseases because the molecular interaction is identical in all those situations as well.

Various embodiments of the present invention provide for compounds and compositions of peptides and analogs, derivatives, mimetics, and fragments thereof comprising, consisting essentially of or consisting of SEQ ID NO:1 and SEQ ID NO:2.

These compounds and compositions, being capable of specifically blocking the interaction between FcRn and albumin, are useful for the treatment of diseases and conditions wherein albumin levels need to be decreased or chronic conditions wherein albumin becomes pathogenic due to disease related modifications. Accordingly, methods for in vivo, ex vivo and in vitro inhibiting or reducing albumin binding to FcRn are provided. Methods for treatment of conditions with excessive albumin using the peptides of the invention are also provided. In some aspects of all the embodiments of the present invention, these peptides are non-naturally occurring peptides and/or are not found in nature.

In various embodiments, the present invention provides for an isolated polypeptide that specifically blocks the interaction between neonatal Fc receptor (FCRN) and albumin comprising at least one peptide subunit consisting of an amino acid sequence of Formula I: $X_1$-Y-$X_2$-C-$X_3$-$X_4$-W-$X_5$-$X_6$-$X_7$-W-C-$X_8$-$X_9$-V-$X_{10}$-$X_{11}$ (SEQ ID NO:7), wherein $X_1$, $X_2$, $X_3$, $X_4$, $X_5$, $X_6$, $X_7$, $X_8$, $X_9$, $X_{10}$, and $X_{11}$ is each independently selected from any amino acid, or is deleted.

In various embodiments, the present invention provides for an isolated polypeptide that specifically blocks the interaction between neonatal Fc receptor (FCRN) and albumin comprising at least one peptide subunit consisting of an amino acid sequence of Formula I: $X_1$-Y-$X_2$-C-$X_3$-$X_4$-W-$X_5$-$X_6$-$X_7$-W-C-$X_8$-$X_9$-V-$X_{10}$-$X_{11}$ (SEQ ID NO:7), wherein:
$X_1$ is R or a conservative amino acid substitution of R,
$X_2$ is F or a conservative amino acid substitution of F,
$X_3$ is T or a conservative amino acid substitution of T,
$X_4$ is K or a conservative amino acid substitution of K,
$X_5$ is H or a conservative amino acid substitution of H,
$X_6$ is G or a conservative amino acid substitution of G,
$X_7$ is C or a conservative amino acid substitution of C,
$X_8$ is E or a conservative amino acid substitution of E,
$X_9$ is E or a conservative amino acid substitution of E,
$X_{10}$ is G, a conservative amino acid substitution of G, or is deleted, and
$X_{11}$ is T, a conservative amino acid substitution of T, or is deleted (an embodiment disclosed as SEQ ID NO: 9).

In various embodiments, the present invention provides for an isolated polypeptide that specifically blocks the interaction between neonatal Fc receptor (FCRN) and albumin comprising at least one peptide subunit consisting of an amino acid sequence of Formula I: $X_1$—Y-$X_2$-C-$X_3$-$X_4$-W-$X_5$-$X_6$-$X_7$-W-C-$X_8$-$X_9$-V-$X_{10}$-$X_{11}$ (SEQ ID NO:7), wherein:
$X_1$ is R or a conservative amino acid substitution of R,
$X_2$ is F or a conservative amino acid substitution of F,
$X_3$ is T or a conservative amino acid substitution of T,
$X_4$ is K or a conservative amino acid substitution of K,
$X_5$ is K or a conservative amino acid substitution of K,
$X_6$ is H or a conservative amino acid substitution of H,
$X_7$ is G or a conservative amino acid substitution of G,
$X_8$ is E or a conservative amino acid substitution of E,
$X_9$ is E or a conservative amino acid substitution of E,
$X_{10}$ is G, a conservative amino acid substitution of G, or is deleted, and
$X_{11}$ is T, a conservative amino acid substitution of T, or is deleted (an embodiment disclosed as SEQ ID NO: 124).

Examples of conservative amino acid substitutions are further discussed herein.

$X_1$-Y-$X_2$-C-$X_3$-$X_4$-W-$X_5$-$X_6$-$X_7$-W-C-$X_8$-$X_9$-V-$X_{10}$-$X_{11}$ (SEQ ID NO:7), wherein $X_1$ is R, or wherein $X_2$ is F, or wherein $X_7$ is G, or wherein $X_{10}$ is E (embodiment disclosed as SEQ ID NO: 13), or wherein $X_1$ is R and $X_2$ is F (embodiment disclosed as SEQ ID NO: 11), or a 2 of 4 combination of wherein $X_1$ is R, $X_2$ is F, $X_7$ is G, and $X_{10}$ is E (embodiment disclosed as SEQ ID NO: 13), or a 3 of 4 combination of wherein $X_1$ is R, $X_2$ is F, $X_7$ is G, and $X_{10}$ is E (embodiment disclosed as SEQ ID NO: 13), or wherein $X_1$ is R, $X_2$ is F, $X_7$ is G, and $X_{10}$ is E (embodiment disclosed as SEQ ID NO: 13).

In various embodiments, the present invention provides for an isolated polypeptide that specifically blocks the interaction between neonatal Fc receptor (FCRN) and albumin comprising at least one peptide subunit consisting of an amino acid sequence that is at least 35%, 41%, 47%, 52%, 58%, 64%, 70%, 76%, 82%, 88%, or 94% identical to RYFCTKWKHGWCEEVGT (SEQ ID NO:1), In certain embodiments, the peptide subunit consists of an amino acid sequence that is at least 90, 91, 92, 93, 94, 95, 96, 97, 98, or 99% identical to SEQ ID NO:1. In particular embodiments, the peptide subunit consists of an amino acid sequence that is identical to SEQ ID NO:1.

In various embodiments, the present invention provides for an isolated polypeptide that specifically blocks the interaction between neonatal Fc receptor (FCRN) and albumin comprising at least one peptide subunit consisting of an amino acid sequence selected from Table 1.

TABLE 1

Affinity of SYN571 and analogs for soluble human FcRn by surface plasmon resonance (SPR) analysis where shFcRn is immobilized on the sensor chip.

| Peptide | SEQ ID NO: | Sequence | Kd, pH 6** Biacore uM | Data Fit at pH 6 Biacore uM | Kd, pH 7.4 Biacore uM | Kd Ratio 7.4/6.0 |
|---|---|---|---|---|---|---|
| SYN571 | 3 | Ac-AGRYFCTKWKHGWCEEVGTGGGK-CONH2 | 0.45, 0.50 | steadystate | 13.1 | 29 |
| SYN1541 | 18 | Ac-RYFCTKWKHGWCEEV-CONH2 | 9.7, 10 | steadystate | | |
| SYN1542 | 19 | Ac-AYFCTKWKHGWCEEV-CONH2 | 13.8 | steadystate | | |

TABLE 1-continued

Affinity of SYN571 and analogs for soluble human FcRn by surface plasmon resonance (SPR) analysis where shFcRn is immobilized on the sensor chip.

| Peptide | SEQ ID NO: | Sequence | Kd, pH 6** Biacore uM | Data Fit at pH 6 Biacore uM | Kd, pH 7.4 Biacore uM | Kd Ratio 7.4/6.0 |
|---|---|---|---|---|---|---|
| SYN1543 | 20 | Ac-RAFCTKWKHGWCEEV-CONH2 | 67.5 | steadystate | | |
| SYN1544 | 21 | Ac-RYACTKWKHGWCEEV-CONH2 | 7.7 | steadystate | | |
| SYN1545 | 22 | Ac-RYFCAKWKHGWCEEV-CONH2 | 9.3 | steadystate | | |
| SYN1546 | 23 | Ac-RYFCTAWKHGWCEEV-CONH2 | 14.2 | steadystate | | |
| SYN1547 | 24 | Ac-RYFCTKAKHGWCEEV-CONH2 | >100 | steadystate | | |
| SYN1548 | 25 | Ac-RYFCTKWAHGWCEEV-CONH2 | 9.3 | steadystate | | |
| SYN1549 | 26 | Ac-RYFCTKWKAGWCEEV-CONH2 | 27.4 | steadystate | | |
| SYN1550 | 27 | Ac-RYFCTKWKHAWCEEV-CONH2 | 39.4 | steadystate | | |
| SYN1551 | 28 | Ac-RYFCTKWKHGACEEV-CONH2 | >200 | steadystate | | |
| SYN1552 | 29 | Ac-RYFCTKWKHGWCAEV-CONH2 | 28.5 | steadystate* | | |
| SYN1553 | 30 | Ac-RYFCTKWKHGWCEAV-CONH2 | 9.5 | steadystate | | |
| SYN1554 | 31 | Ac-RYFCTKWKHGWCEEA-CONH2 | >100 | steadystate | | |
| SYN1555 | 32 | Ac-RYF-Pen-TKWKHGWCEEV-CONH2 | >100 | steadystate | | |
| SYN1556 | 33 | Ac-RYFCTKWKHGW-Pen-EEV-CONH2 | >100 | steadystate | | |
| SYN1557 | 34 | Ac-RYF-Pen-TKWKHGW-Pen-EEV-CONH2 | >100 | steadystate | | |
| SYN1558 | 35 | Ac-RYFATKWKHGWAEEV-CONH2 | >100 | steadystate | | |
| SYN1705 | 36 | Ac-GRYFCTKWKHGWCEEVGTGGGK-CONH2 | 0.84 | steadystate | | |
| SYN1706 | 37 | Ac-RYFCTKWKHGWCEEVGTGGGK-CONH2 | 0.9 | steadystate | | |
| SYN1707 | 38 | Ac-AGRYFCTKWKHGWCEEVGTGGG-CONH2 | 0.49 | steadystate | | |
| SYN1708 | 39 | Ac-AGRYFCTKWKHGWCEEVGTGG-CONH2 | 0.57 | steadystate | | |
| SYN1709 | 40 | Ac-AGRYFCTKWKHGWCEEVGTG-CONH2 | 0.68 | steadystate | | |
| SYN1710 | 41 | Ac-AGRYFCTKWKHGWCEEVGT-CONH2 | 0.59 | steadystate | | |
| SYN1711 | 42 | Ac-AGRYFCTKWKHGWCEEVG-CONH2 | 1.56 | steadystate | | |
| SYN1712 | 43 | Ac-AGRYFCTKWKHGWCEEV-CONH2 | 4.62 | steadystate | | |

In various embodiments, the present invention provides for an isolated polypeptide that specifically blocks the interaction between neonatal Fc receptor (FCRN) and albumin comprising two or more peptide subunits consisting of the amino acid sequence that is at least 35%, 41%, 47%, 52%, 58%, 64%, 70%, 76%, 82%, 88%, or 94% identical to the amino acid sequence set forth in the SEQ ID NO: 1. In various embodiments, isolated polypeptide comprises four peptide subunits.

In certain embodiments, the peptide subunit consists of an amino acid sequence that is at least 90, 91, 92, 93, 94, 95, 96, 97, 98, or 99% identical to SEQ ID NO:1. In particular embodiments, the peptide subunit consists of an amino acid sequence that is identical to SEQ ID NO:1. In various aspects, no more than one amino acid is altered. In other aspects, no more than 2 amino acids are changed. In some aspects, no more than 3 amino acids are changed. In some aspects, no more than 5 amino acids are changed.

In various embodiments, the present invention provides for an isolated polypeptide that specifically blocks the interaction between neonatal Fc receptor (FCRN) and albumin comprising two or more peptide subunits consisting of an amino acid sequence selected from Table 1.

In various embodiments, the two or more polypeptide subunits are linked by direct fusion.

In various embodiments, the two or more polypeptide subunits are linked by a linker.

In certain embodiments, the linker is a peptide linker comprising 1-10, 2-10, 3-10, 3-5, such as 1, 2, 3, 4, 5, 6, 7, 8, 9, or 10 amino acids. In certain embodiments, the linker is a glycine linker comprising 1-10 glycine residues (SEQ ID NO: 14). In certain embodiments, the linker is a glycine-serine linker comprising 1-10 glycine and serine residues (SEQ ID NO: 15). In certain embodiments, the glycine linker comprises 3-5 glycine residues (SEQ ID NO: 16). In certain embodiments, the linker is a glycine-serine linker comprising 3-5 glycine and serine residues (SEQ ID NO: 17).

In certain embodiments, the linker is a mini-PEG™ as described herein.

In some aspects, the linker can be formed from the following formula: H—(O—CH2-CH2)n-OH, wherein n is an integer from 2-12. In certain embodiments, n is an integer from 2-5.

Additional examples of linkers are further described herein.

In various embodiments, the isolated polypeptide is a cyclic polypeptide.

Also provided are compositions comprising the isolated polypeptides. The compositions may comprise buffers, fillers or carriers. In some aspects of all the embodiments of the invention, the composition is a pharmaceutical composition comprising the peptides of the invention and further comprising a pharmaceutically acceptable carrier.

The invention described herein is also based, at least in part, on the discovery that polypeptides named "SYN514", "SYN515" and "SYN531" are capable of binding to non-IgG and non-albumin competitive site on a FCRN alpha 3 domain. "SYN514" polypeptide refers to a polypeptide having the sequence Ac-AGVMHCFWDEEFKCDQG-GTGGGK-CONH2 (SEQ ID NO:4). In some aspects, analogs, derivatives, or fragments thereof can be used. "SYN515" polypeptide refers to a polypeptide having the sequence Ac-AGYMTCKWDDGFSCEYVGTGGGK-CONH2 (SEQ ID NO:5). In some aspects, analogs, derivatives, or fragments thereof can also be used. "SYN531" polypeptide refers to a polypeptide having the sequence Ac-AGVMKCWWDEEMLCRAFGTGGGK-CONH2 (SEQ ID NO:6). In some aspects, analogs, derivatives, or fragments thereof can also be used.

Various embodiments of the present invention provide for compounds and compositions of peptides and analogs, derivatives, mimetics, and fragments thereof comprising, consisting essentially of or consisting of SEQ ID NO:4, SEQ ID NO:5 and SEQ ID NO:6.

These compounds and compositions, being capable of binding to non-IgG and non-albumin competitive site on a FCRN alpha 3 domain, are useful for tracking neonatal Fc receptor (FCRN) without inhibiting IgG or albumin binding or function.

Accordingly, methods for in vivo, ex vivo and in vitro binding to non-IgG and non-albumin competitive site on a FCRN alpha 3 domain are provided. Methods of tracking neonatal Fc receptor without inhibiting IgG or albumin binding or function using the peptides of the invention are also provided. In various embodiments, these polypeptides can further comprise a label to produce a signal and tracking FCRN can be performed by detecting the signal.

In various embodiments, the present invention provides for an isolated polypeptide that specifically binds to non-IgG and non-albumin competitive site on a FCRN alpha 3 domain comprising at least one peptide subunit consisting of an amino acid sequence AGVMHCFWDEEFKCDQG-GTGGGK (SEQ ID NO:4), with up to four amino acid substitutions and/or up to eight amino acid deletions. In various embodiments, the up to four amino acid substitutions are in residues 3-17 of SEQ ID NO:4. In various embodiments, least one of the up to four amino acid substitutions is a conservative amino acid substitution. In various embodiments, the up to eight amino acid deletions are selected from residues 1, 2, 18, 19, 20, 21, 22, or 23.

In various embodiments, the present invention provides for an isolated polypeptide that specifically binds to non-IgG and non-albumin competitive site on a FCRN alpha 3 domain comprising at least one peptide subunit consisting of an amino acid sequence as set forth in SEQ ID NO:4.

In various embodiments, the present invention provides for an isolated polypeptide that specifically binds to non-IgG and non-albumin competitive site on a FCRN alpha 3 domain comprising at least one peptide subunit consisting of an amino acid sequence that is at least 73%, 80%, 86% or 93% identical to residues 3-17 of AGVMHCF-WDEEFKCDQGGTGGGK (SEQ ID NO:4).

In various embodiments, the present invention provides for an isolated polypeptide that specifically binds to non-IgG and non-albumin competitive site on a FCRN alpha 3 domain comprising at least one peptide subunit consisting of an amino acid sequence that is at 100% identical to residues 3-17 of AGVMHCFWDEEFKCDQGGTGGGK (SEQ ID NO:4).

In various embodiments, the present invention provides for an isolated polypeptide that specifically binds to non-IgG and non-albumin competitive site on a FCRN alpha 3 domain comprising at least one peptide subunit consisting of an amino acid sequence AGYMTCKWDDGFSC-EYVGTGGGK (SEQ ID NO: 5) with up to three amino acid substitutions and/or up to eight amino acid deletions. In various embodiments, the up to three amino acid substitutions are in residues 3-17 of SEQ ID NO:5. In various embodiments, at least one of the up to three amino acid substitutions is a conservative amino acid substitution. In various embodiments, the up to eight amino acid deletions are selected from residues 1, 2, 18, 19, 20, 21, 22, 23. In various embodiments, the at least one peptide subunit consist of an amino acid sequence as set forth in SEQ ID NO: 5.

In various embodiments, the present invention provides for an isolated polypeptide that specifically binds to non-IgG and non-albumin competitive site on a FCRN alpha 3 domain comprising at least one peptide subunit consisting of an amino acid sequence at least 80%, 86% or 93% identical to residues 3-17 of AGYMTCKWDDGFSCEYVGTGGGK (SEQ ID NO: 5).

In various embodiments, the present invention provides for an isolated polypeptide that specifically binds to non-IgG and non-albumin competitive site on a FCRN alpha 3 domain comprising at least one peptide subunit consisting of an amino acid sequence identical to residues 3-17 of AGYMTCKWDDGFSCEYVGTGGGK (SEQ ID NO: 5).

In various embodiments, the present invention provides for an isolated polypeptide that specifically binds to non-IgG and non-albumin competitive site on a FCRN alpha 3 domain comprising at least one peptide subunit consisting of an amino acid sequence AGVMKCWWDEEMLCRAFGTGGGK (SEQ ID NO:6) with up to two amino acid substitutions and/or up to eight amino acid deletions. In various embodiments, the up to two amino acid substitutions are in residues 3-17 of SEQ ID NO:6. In various embodiments, at least one of the up to two amino acid substitutions is a conservative amino acid substitution. In various embodiments, the up to eight amino acid deletions are selected from residues 1, 2, 18, 19, 20, 21, 22, 23. In various embodiments, the at least one peptide subunit consist of an amino acid sequence as set forth in SEQ ID NO: 6.

In various embodiments, the present invention provides for an isolated polypeptide that specifically binds to non-IgG and non-albumin competitive site on a FCRN alpha 3 domain comprising at least one peptide subunit consisting of an amino acid sequence at least 86% or 93% identical to residues 3-17 of AGVMKCWWDEEMLCRAFGTGGGK (SEQ ID NO: 6).

In various embodiments, the present invention provides for an isolated polypeptide that specifically binds to non-IgG and non-albumin competitive site on a FCRN alpha 3 domain comprising at least one peptide subunit consisting of an amino acid sequence identical to residues 3-17 of AGVMKCWWDEEMLCRAFGTGGGK (SEQ ID NO: 6).

In various embodiments, the present invention provides for an isolated polypeptide that specifically binds to non-IgG and non-albumin competitive site on a FCRN alpha 3 domain comprising at least one peptide subunit consisting of an amino acid sequence selected from Table 2.

TABLE 2

Affinity of SYN514, SYN515, and SYN531 analogs to shFcRn by SPR, using immobilized shFcRn.

| Peptide | SEQ ID NO: | Sequence EpoFc monomer human IgG1 | Kd, pH 6** Biacore uM | Data Fit at pH 6 Biacore | Kd, pH 7.4 Biacore uM | Kd Ratio 7.4/ 6.0 | Kd Cyno, pH 6 Biacore uM |
|---|---|---|---|---|---|---|---|
| SYN514 | 4 | Ac-AGVMHCFWDEEFKCDQGGTGGGK-CONH2 | | | | | |
| SYN1197 | 44 | Ac-VMHCFWDEEFKCDQG-CONH2 | 0.74 | steadystate | 62 | | 84 |
| SYN1215 | 45 | Ac-VMACFWDEEFKCDQG-CONH2 | 2.84 | steadystate | | | |
| SYN1216 | 46 | Ac-VMHCFWDEAFKCDQG-CONH2 | 3.6 | steadystate | 186 | | 52 |
| SYN1217 | 47 | Ac-VMHCAWDEEFKCDQG-CONH2 | >20 | steadystate | no bind | | n/a |
| SYN1256 | 48 | Ac-YMHCFWDEEFKCDQG-CONH2 | 0.72 | steadystate | 50 | | 69 |
| SYN1257 | 49 | Ac-VMHCFWDEGFKCDQG-CONH2 | 1.45 | steadystate | 40 | | 28 |
| SYN1258 | 50 | Ac-VMHCFWDEEFKCEQG-CONH2 | 0.37 | steadystate | 24 | | 65 |
| SYN1259 | 51 | Ac-VMHCFWDEEFKCDYG-CONH2 | 0.091 | steadystate | 12 | | 132 |
| SYN1260 | 52 | Ac-VMHCFWDEEFKCDQV-CONH2 | 0.3 | steadystate | 22 | | 73 |
| SYN1381 | 53 | Ac-VMHCFWDEEFRCDYG-CONH2 | 0.06 | steadystate | 4.9 | | 82 |
| SYN1382 | 54 | Ac-VMHCFWDEAFRCDQG-CONH2 | 4.4 | steadystate | 112 | | 25 |

TABLE 2-continued

Affinity of SYN514, SYN515, and SYN531 analogs to shFcRn by SPR, using immobilized shFcRn.

| Peptide | SEQ ID NO: | Sequence EpoFc monomer human IgG1 | Kd, pH 6** Biacore uM | Data Fit at pH 6 Biacore uM | Kd, pH 7.4 Biacore uM | Kd Ratio 7.4/ 6.0 | Kd Cyno, pH 6 Biacore uM |
|---|---|---|---|---|---|---|---|
| SYN1383 | 55 | Ac-VMHCFWDEEFRCEYV-CONH2 | 0.032 | steadystate | 1.1 | 34 | |
| SYN1408 | | 1216 dimer: Lys to Arg substitution = 1382 dimer | | | | | |
| SYN515 | 5 | Ac-AGYMTCKWDDGFSCEYVGTGGGK-CONH2 | 0.23 ± 0.03 | 2 site | 18 ±5 | 78 | |
| SYN580 | 56 | Ac-YMTCKWDDGFSCEYV-CONH2 | 0.23 ± 0.04, 0.31 | 2 site, steady state | 16 | 52 | |
| SYN1144 | 57 | Ac-AMTCKWDDGFSCEYV-CONH2 | 1.25 ± 0.32 | steady state | 29.1 | 23.3 | |
| SYN1145 | 58 | Ac-YATCKWDDGFSCEYV-CONH2 | 57 ± 6 | ss | nd | n/a | |
| SYN1146 | 59 | Ac-YMACKWDDGFSCEYV-CONH2 | 0.25 ± 0.05 | 2 site | 8.6 | 34.4 | |
| SYN1147 | 60 | Ac-YMTCAWDDGFSCEYV-CONH2 | 0.47 ± 0.11, 0.48 | 2 site, steady state | 27 | 56 | |
| SYN1148 | 61 | Ac-YMTCKADDGFSCEYV-CONH2 | no binding | n/a | n/a | n/a | |
| SYN1149 | 62 | Ac-YMTCKWADGFSCEYV-CONH2 | 1.54 | steady state | 12 | 7.8 | |
| SYN1150 | 63 | Ac-YMTCKWDAGFSCEYV-CONH2 | 0.18 ± 0.04 | 2 site | 0.4 | 2.2 | |
| SYN1151 | 64 | Ac-YMTCKWDDAFSCEYV-CONH2 | 1.5 ± 0.22, 0.83 | steady state | 20.7 | 25 | |
| SYN1152 | 65 | Ac-YMTCKWDDGASCEYV-CONH2 | no binding | | n/a | n/a | |
| SYN1153 | 66 | Ac-YMTCKWDDGFACEYV-CONH2 | 0.43 | steady state | 16.5 | 38 | |
| SYN1154 | 67 | Ac-YMTCKWDDGFSCAYV-CONH2 | 1.5 ± 0.55, 0.46 | steady state | 9.2 | 20 | |
| SYN1155 | 68 | Ac-YMTCKWDDGFSCEAV-CONH2 | 1.76 | steady state | 17.3 | 9.8 | |
| SYN1156 | 69 | Ac-YMTCKWDDGFSCEYA-CONH2 | 0.58 | steady state | 22 | 38 | |
| SYN1160 | 70 | Ac-YMTAKWDDGFSAEYV-CONH2 | | | | | |
| SYN1161 | 71 | Ac-MTCKWDDGFSCEYV-CONH2 | 1.21 ± 0.07, 1.17 | steady state | | | |
| SYN1162 | 72 | Ac-TCKWDDGFSCEYV-CONH2 | 97.6 ± 7.4 | | nd | n/a | |
| SYN1163 | 73 | Ac-CKWDDGFSCEYV-CONH2 | no binding | | nd | n/a | |
| SYN1164 | 74 | Ac-YMTCKWDDGFSCEY-CONH2 | 0.57 ± 0.02 | | | | |
| SYN1165 | 75 | Ac-YMTCKWDDGFSCE-CONH2 | 40.3 ± 5.7 | | nd | n/a | |

TABLE 2-continued

Affinity of SYN514, SYN515, and SYN531 analogs to shFcRn by SPR, using immobilized shFcRn.

| Peptide | SEQ ID NO: | Sequence EpoFc monomer human IgG1 | Kd, pH 6** Biacore uM | Data Fit at pH 6 Biacore | Kd, pH 7.4 Biacore uM | Kd Ratio 7.4/ 6.0 | Kd Cyno, pH 6 Biacore uM |
|---|---|---|---|---|---|---|---|
| SYN1166 | 76 | Ac-YMTCKWDDGFSC-CONH2 | insol | | | n/a | n/a |
| SYN1167 | 77 | Ac-YMTPenKWDDGFSCEYV-CONH2 | 2.03 ± 0.2 | | nd | | n/a |
| SYN1168 | 78 | Ac-YMTCKWDDGFSPenEYV-CONH2 | 1.94 ± 0.4 | | nd | | n/a |
| SYN1169 | 79 | Ac-YMTPenKWDDGFSPenEYV-CONH2 | 0.87 ± 0.1 | | nd | | n/a |
| SYN531 | 6 | Ac-AGVMKCWWDEEMLCRAFGTGGGK-CONH2 | 0.45, 0.30 | steadystate | 44.4 | | 99 |
| SYN1532 | 80 | Ac-VMKCWWDEEMLCRAF-CONH2 | 0.154 | steadystate | 17.3 | | 112 |
| SYN1533 | 81 | Ac-VMHCWWDEEMLCRAF-CONH2 | 0.558 | steady state | 59.1 | | 106 |
| SYN1534 | 82 | Ac-VMRCWWDEEMLCRAF-CONH2 | 0.162 | steadystate | 20.2 | | 125 |
| SYN1535 | 83 | Ac-VMKCFWDEEMLCRAF-CONH2 | 2.6 | steadystate | 91.3 | | 35 |
| SYN1536 | 84 | Ac-VMKCWWDEEFLCRAF-CONH2 | 0.031*, 0.018 | steadystate | 1.1 | | 61 |
| SYN1537 | 85 | Ac-VMKCWWDEEMRCRAF-CONH2 | 0.616 | steadystate | 63.2 | | 103 |
| SYN1538 | 86 | Ac-VMKCWWDEEMLCEAF-CONH2 | 0.267 | steadystate | 18.9 | | 71 |
| SYN1539 | 87 | Ac-VMKCWWDEEMLCRYF-CONH2 | 0.104 | steadystate | 8.6 | | 83 |
| SYN1540 A | 88 | Ac-VMKCWWDEEMLCRAV-CONH2 | 0.572 | steadystate | 45.7 | | 80 |
| SYN1540 B | 89 | Ac-VMKCWWDEEMLCRAV-CONH2 | 0.702 | steadystate | not tested | | |
| SYN1559 | 90 | Ac-VMHAFWDEEFRAEYV-CONH2 | nb | aggregates/non specific | | | | note:
pH 7.4 data only 100 uM; Therefore, Kd may be higher; SYN1383: No block in IgG competition ELISA at 100 micromolar In various embodiments, the present invention provide for an isolated polypeptide that specifically binds to non-IgG and non-albumin competitive site on a FCRN alpha 3 domain comprising two or more peptide subunits consisting of the amino acid sequence as described above. In various embodiments, isolated polypeptide comprises four peptide subunits.

In various embodiments, the two or more polypeptide subunits are linked by direct fusion.

In various embodiments, the two or more polypeptide subunits are linked by a linker.

In certain embodiments, the linker is a peptide linker comprising 1-10, 2-10, 3-10, 3-5, such as 1, 2, 3, 4, 5, 6, 7, 8, 9, or 10 amino acids. In certain embodiments, the linker is a glycine linker comprising 1-10 glycine residues (SEQ ID NO: 14). In certain embodiments, the linker is a glycine-serine linker comprising 1-10 glycine and serine residues (SEQ ID NO: 15). In certain embodiments, the glycine linker comprises 3-5 glycine residues (SEQ ID NO: 16). In certain embodiments, the linker is a glycine-serine linker comprising 3-5 glycine and serine residues (SEQ ID NO: 17).

In certain embodiments, the linker is a mini-PEG™ as described herein.

In some aspects, the linker can be formed from the following formula: H—(O—CH2-CH2)n-OH, wherein n is an integer from 2-12. In certain embodiments, n is an integer from 2-5.

Additional examples of linkers are further described herein.

In various embodiments, the isolated polypeptide is a cyclic polypeptide.

Also provided by the present invention are compositions comprising the isolated polypeptides. The compositions may comprise buffers, fillers or carriers. In some aspects of all the embodiments of the invention, the composition is a pharmaceutical composition comprising the peptides of the invention and further comprising a pharmaceutically acceptable carrier.

This invention is also based, at least in part, on a finding that certain residues on human serum albumin are relevant to FCRN binding. These residues include, for example, Glu565, Asn111 or Asn109 of SEQ ID NO:8

As such, various embodiments of the present invention provide for a method of screening for loss or gain of function mutations in human serum albumin (HSA) comprising: providing a mutant protein comprising SEQ ID NO:8, wherein one or more amino acids selected from Glu565, Asn111 or Asn109 have been mutated to any other amino acid or an amino acid analog; contacting the mutant protein with human FcRn; detecting binding affinity of the human FcRn with the mutant protein; comparing the binding activity of the mutant protein to human FcRn to binding activity of the a wild-type protein comprising SEQ ID NO: 8 to human FcRn; identifying a loss of function mutation when the binding activity of the mutant protein is decreased or abolished compared to the wild-type protein and identifying a gain of function mutation when the binding activity of the mutant protein is increased compared to the wild type protein. In various embodiments, the method can further comprise mutating one or more of the residues selected from Glu565, Asn111 and Asn109 of SEQ ID NO: 8.

Various embodiments of the present invention provide for a method of screening for loss or gain of function mutations in human serum albumin (HSA) consisting of: providing a mutant protein comprising SEQ ID NO:8, wherein one or more amino acids selected from Glu565, Asn111 or Asn109 have been mutated to any other amino acid or an amino acid analog; contacting the mutant protein with human FcRn; detecting binding affinity of the human FcRn with the mutant protein; comparing the binding activity of the mutant protein to human FcRn to binding activity of the a wild-type protein comprising SEQ ID NO: 8 to human FcRn; identifying a loss of function mutation when the binding activity of the mutant protein is decreased or abolished compared to the wild-type protein and identifying a gain of function mutation when the binding activity of the mutant protein is increased compared to the wild type protein.

Various embodiments of the present invention provide for a method of screening for loss or gain of function mutations in human serum albumin (HSA) consisting of: providing a mutant protein comprising SEQ ID NO:8, wherein one or more amino acids selected from Glu565, Asn111 or Asn109 have been mutated to any other amino acid or an amino acid analog; contacting the mutant protein with human FcRn; detecting binding affinity of the human FcRn with the mutant protein; comparing the binding activity of the mutant protein to human FcRn to binding activity of the a wild-type protein comprising SEQ ID NO: 8 to human FcRn; identifying a loss of function mutation when the binding activity of the mutant protein is decreased or abolished compared to the wild-type protein and identifying a gain of function mutation when the binding activity of the mutant protein is increased compared to the wild type protein; and mutating one or more of the residues selected from Glu565, Asn111 and Asn109 of SEQ ID NO: 8.

In various embodiments, the method of screening for loss or gain of function mutations do not comprise using a test compound for purposes of detecting whether the test compound inhibits binding between the FcRn polypeptide (or fragments thereof) and albumin polypeptide (or fragments thereof).

Detecting the affinity can be performed, for example, using surface plasmon resonance, X-ray crystallography, nuclear magnetic resonance spectroscopy, size-exclusion or affinity chromatography, isothermal titration calorimetry, affinity electrophoresis, Bio-Layer Interferometry, dual polarization interferometry (DPI), fluorescence polarization/anisotropy, fluorescence correlation spectroscopy, or fluorescence correlation spectroscopy. In certain embodiments, the steps of comparing and identifying can be performed by a non-human machine, as further described herein.

Various aspects of the embodiments of the present invention are further described herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms.

In some aspects, one can use "modified polypeptides" which refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids.

In some embodiments, a polypeptide may be derived, isolated and optionally purified from a natural biological source. These embodiments include, for example, polypeptides that are used in the methods of the present invention. In other embodiments, a polypeptide may be produced by recombinant technology, isolated and optionally purified, using genetic code encoding the polypeptide in a cellular system, either in prokaryotic or eukaryotic expression systems. These embodiments include, for example, isolated polypeptides of the present invention as well as polypeptides that are used in the methods of the present invention. The nucleic acids encoding the recombinant peptides can be optimized for synthesis in a particular cell using routine methods. The peptides may also be synthesized using well-known chemical peptide synthesis.

A fragment of the polypeptide can vary between 10 and 50 amino acids if the peptide is a monomer or a dimer. Longer peptides are contemplated if the peptide is fused with another peptide or more than two, such as three or four subunits are used. Typically, it is advantageous to use shorter peptides. In our example we used a 37-mer, which included a three glycine residue bridge between two subunits of SEQ ID NO: 1. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

Analogs, Derivatives, Mimetics and Fragments of "SYN1753", "SYN3258", "SYN514", "SYN515", and "SYN531" Polypeptides Various embodiments of the present invention provide for analogs, derivatives, mimetics and fragments of the isolated polypeptide (e.g., "SYN1753", "SYN3258") that specifically block the interaction between neonatal Fc receptor (FCRN) and albumin and are based on the peptides as described herein.

Other embodiments provide for analogs, derivatives, mimetics and fragments of the isolated polypeptide (e.g., "SYN514", "SYN515", "SYN531") capable of binding to a non-IgG and non-albumin competitive site on a FCRN alpha 3 domain In various embodiments, the isolated polypeptide comprises at least one amino acid analog, such as a D-amino acid, or amino acid mimetic.

In various embodiments, the isolated polypeptide comprises a modified peptide backbone.

In other embodiments, the isolated polypeptide comprises a hydrophilic unstructured polymer for the purposes of extending in vivo pharmacokinetic properties. Examples of hydrophilic unstructured polymer include XTEN from Amunix. XTEN can be characterized as (a) having amino acid residues that is at least 36 to about 3000 amino acid residues; (b) the sum of glycine (G), alanine (A), serine (S), threonine (T), glutamate (E) and proline (P) residues constitutes more than about 90% of the total amino acid residues of the XTEN; (c) the XTEN sequence is substantially non-repetitive such that (i) the XTEN sequence contains no three contiguous amino acids that are identical unless the amino acids are serine, (ii) at least about 80% of the XTEN sequence consists of non-overlapping sequence motifs, each of the sequence motifs comprising about 9 to about 14 amino acid residues, wherein any two contiguous amino acid residues does not occur more than twice in each of the sequence motifs; or (iii) the XTEN sequence has a subsequence score of less than 10; (d) the XTEN sequence has greater than 90%>random coil formation as determined by GOR algorithm; (e) the XTEN sequence has less than 2% alpha helices and 2% beta-sheets as determined by Chou-Fasman algorithm; and (f) the XTEN sequence lacks a predicted T-cell epitope when analyzed by TEPITOPE algorithm, wherein the TEPITOPE algorithm prediction for epitopes within the XTEN sequence is based on a score of −9. XTEN is also described in European Patent Publication No. EP2552967, which is hereby incorporated by reference as though fully set forth in its entirety.

In various embodiments, the isolated polypeptide comprises polyethylene glycol (PEG) for the purposes of extending in vivo pharmacokinetic properties. Suitable PEG's are further discussed herein.

In various embodiments, the isolated polypeptide comprises HTHGMDELKY-OH. (SEQ ID NO: 91) See e.g., Zeng et al. (Synthetic Polymer Nanoparticles with Antibody-Like Affinity for a Hydrophilic Peptide, ACS Nano. 2010 Jan. 26; 4(1): 199), herein incorporated by reference as though fully set forth in its entirety.

In various embodiments, the isolated polypeptide is acetylated. In various embodiments, the isolated polypeptide further comprises at least one second protein or peptide to form a fusion peptide. In various embodiments, the at least second protein or peptide comprises an epitope tag or a half-life extender or both.

An "analog" of a molecule such as a peptide refers to a molecule similar in function to either the entire molecule or to a fragment thereof. The term "analog" is also intended to include allelic species and induced variants. Analogs typically differ from naturally occurring peptides at one or a few positions, often by virtue of conservative substitutions. Analogs typically exhibit at least 80 or 90% sequence identity with natural peptides. Some analogs also include unnatural amino acids or modifications of N or C terminal amino acids. Examples of unnatural amino acids are, for example but not limited to; disubstituted amino acids, N-alkyl amino acids, lactic acid, 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine. Fragments and analogs can be screened for prophylactic or therapeutic efficacy in transgenic animal models as described below. Formula I of the present invention includes the inventive peptides and analogs.

"Conservative amino acid substitutions" result from replacing one amino acid with another having similar structural and/or chemical properties, such as the replacement of a leucine with an isoleucine or valine, an aspartate with a glutamate, or a threonine with a serine. Thus, a "conservative substitution" of a particular amino acid sequence refers to substitution of those amino acids that are not critical for polypeptide activity or substitution of amino acids with other amino acids having similar properties (e.g., acidic, basic, positively or negatively charged, polar or non-polar, etc.) such that the substitution of even critical amino acids does not reduce the activity of the peptide, (i.e. the ability of the peptide to penetrate the blood brain barrier (BBB)). Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984), incorporated by reference in its entirety.) In some embodiments, individual substitutions, deletions or additions that alter, add or delete a single amino acid or a small percentage of amino acids can also be considered "conservative substitutions" if the change does not reduce the activity of the peptide. Insertions or deletions are typically in the range of about 1 to 5 amino acids. The choice of conservative amino acids may be selected based on the location of the amino acid to be substituted in the peptide, for example if the amino acid is on the exterior of the peptide and expose to solvents, or on the interior and not exposed to solvents.

One can make conservative substitutions to SEQ ID NO: 1 or SEQ ID NO: 2, so long as they do not affect its capacity to specifically block or reduce the binding of albumin to FcRn. One can make conservative substitutions to SEQ ID NO: 4 or SEQ ID NO:5 so long as they do not affect its capacity to specifically bind to a non-IgG and non-albumin competitive site on a FCRN alpha 3 domain.

In alternative embodiments, one can select the amino acid which will substitute an existing amino acid based on the location of the existing amino acid, i.e. its exposure to solvents (i.e. if the amino acid is exposed to solvents or is present on the outer surface of the peptide or polypeptide as compared to internally localized amino acids not exposed to solvents). Selection of such conservative amino acid substitutions are well known in the art, for example as disclosed in Dordo et al, J. MoI Biol, 1999, 217, 721-739 and Taylor et al, J. Theor. Biol. 119(1986); 205-218 and S. French and B. Robson, J. MoI. Evol. 19(1983)171. Accordingly, one can select conservative amino acid substitutions suitable for amino acids on the exterior of a protein or peptide (i.e. amino acids exposed to a solvent), for example, but not limited to, the following substitutions can be used: substitution of Y with F, T with S or K, P with A, E with D or Q, N with D or G, R with K, G with N or A, T with S or K, D with N or E, I with L or V, F with Y, S with T or A, R with K, G with N or A, K with R, A with S, K or P.

In alternative embodiments, one can also select conservative amino acid substitutions encompassed suitable for amino acids on the interior of a protein or peptide, for example one can use suitable conservative substitutions for amino acids is on the interior of a protein or peptide (i.e. the amino acids are not exposed to a solvent), for example but not limited to, one can use the following conservative substitutions: where Y is substituted with F, T with A or S, I with L or V, W with Y, M with L, N with D, G with A, T with A or S, D with N, I with L or V, F with Y or L, S with A or T and A with S, G, T or V. In some embodiments, non-conservative amino acid substitutions are also encompassed within the term of variants.

The term "derivative" as used herein refers to peptides which have been chemically modified, for example but not limited to by techniques such as ubiquitination, labeling, pegylation (derivatization with polyethylene glycol), lipidation, glycosylation, or addition of other molecules. A molecule also a "derivative" of another molecule when it contains additional chemical moieties not normally a part of the molecule. Such moieties can improve the molecule's solubility, absorption, biological half-life, etc. The moieties can alternatively decrease the toxicity of the molecule, eliminate or attenuate any undesirable side effect of the molecule, etc. Moieties capable of mediating such effects are disclosed in Remington's Pharmaceutical Sciences, 18th edition, A. R. Gennaro, Ed., Mack Publ., Easton, Pa. (1990), incorporated herein, by reference, in its entirety.

Thus, in certain aspects of all the embodiments of the invention, the peptides of the invention comprise peptide derivatives, such as pegylated peptides.

Additional Modifications to "SYN1753", "SYN3258" "SYN514", "SYN515", and "SYN531" polypeptides The peptide can be modified to extend the shelf life and/or bioavailability using one or more non-natural peptide bonds or amino acids or by attaching to the peptide functional groups such as, e.g., polyethylene glycol (PEG).

In some aspects, the PEG can be a "mini-PEG™". For example, 8-Amino-3,6-Dioxaoctanoic Acid, (AEEA). These mini-PEG"s are available from Peptides International; for example, as noted in the following table:

Fmoc-mini-PEG ™
Fmoc-8-Amino-3,6-Dioxaoctanoic Acid
9-Fluorenylmethoxycarbonyl-8-Amino-3,6-Dioxaoctanoic Acid
(M.W. 385.42) $C_{21}H_{23}NO_6$
Fmoc-AEEA
Fmoc-mini-PEG-3 ™
Fmoc-11-Amino-3,6,9-Trioxaundecanoic Acid (Syrup)
9-Fluorenylmethoxycarbonyl-11-Amino-3,6,9-Trioxaundecanoic Acid
(M.W. 429.47) $C_{23}H_{27}NO_7$
Fmoc-AEEEA
Boc-mini-PEG ™
Boc-8-Amino-3,6-Dioxaoctanoic Acid•DCHA
tert-Butyloxycarbonyl-8-Amino-3,6-Dioxaoctanoic Acid•
Dicyclohexylamine
(M.W. 263.29•181.3) $C_{11}H_{21}NO_6•C_{12}H_{23}N$
Boc-AEEA
Boc-mini-PEG-3 ™
Boc-11-Amino-3,6,9-Trioxaundecanoic Acid•DCHA
tert-Butyloxycarbonyl-11-Amino-3,6,9-Trioxaundecanoic Acid•
Dicyclohexylamine
(M.W. 307.35•181.32) $C_{13}H_{25}NO_7•C_{12}H_{23}N$
Boc-AEEEA AEEA = [2-(2-Amino-ethoxy)-ethoxy]-acetic acidAEEEA = {2-[2-(2-Amino-ethoxy)-ethoxy]-ethoxy}-acetic acid In some aspects, the PEG can have the following formula: H—(O—$CH_2$-$CH_2$)n-OH, wherein n is an integer from 2-12. In certain embodiments, n is an integer from 2-5.

In some aspects, the polypeptide or protein is a "modified polypeptide" comprising non-naturally occurring amino acids. In some aspects, the polypeptides comprise a combination of naturally occurring and non-naturally occurring amino acids, and in some embodiments, the peptides comprise only non-naturally occurring amino acids.

"Modified peptide" may include the incorporation of non-natural amino acids into the peptides of the invention, including synthetic non-native amino acids, substituted amino acids, or one or more D-amino acids into the peptides (or other components of the composition, with exception for protease recognition sequences) is desirable in certain situations. D-amino acid-containing peptides exhibit increased stability in vitro or in vivo compared to L-amino acid-containing forms. Thus, the construction of peptides incorporating D-amino acids can be particularly useful when greater in vivo or intracellular stability is desired or required. More specifically, D-peptides are resistant to endogenous peptidases and proteases, thereby providing better oral trans-epithelial and transdermal delivery of linked drugs and conjugates, improved bioavailability of membrane-permanent complexes (see below for further discussion), and prolonged intravascular and interstitial lifetimes when such properties are desirable. The use of D-isomer peptides can also enhance transdermal and oral trans-epithelial delivery of linked drugs and other cargo molecules. Additionally, D-peptides cannot be processed efficiently for major histocompatibility complex class II-restricted presentation to T helper cells, and are therefore less likely to induce humoral immune responses in the whole organism. Peptide conjugates can therefore be constructed using, for example, D-isomer forms of cell penetrating peptide sequences, L-isomer forms of cleavage sites, and D-isomer forms of therapeutic peptides. Therefore, in some embodiments the peptides as disclosed comprise L and D amino acids, wherein no more than 1, 2, 3, 4, 5, 6, 7, 8, 9, or 10 D-amino acids are included. In certain aspects, the peptides comprise more than 10 D-amino acids, and in certain aspects all the amino acids of the peptides are D-amino acids.

Modification of Amino Acids

In some embodiments, the peptide fragments, analogs, or derivatives comprise, consist essentially of, or consist of natural amino acids.

In some embodiments, the peptide fragments, analogs, or derivatives comprise, consist essentially of, or consist of amino acid equivalents or other non-amino groups, while still retaining the functional activity of a peptide as compared to the peptide fragments, analogs, or derivatives with natural amino acids. Peptide equivalents can differ from conventional peptides by the replacement of one or more amino acids with related organic acids (such as PABA), amino acids or the like or the substitution or modification of side chains or functional groups.

In some embodiments the peptide fragments, analogs, or derivatives are linear. In some embodiments, the peptide fragments, analogs, or derivatives are cyclic.

As used herein, the term "amino acid" and any reference to a specific amino acid is meant to include naturally occurring amino acids.

In some embodiments the amino acids used are naturally occurring proteogenic and non-proteogenic amino acids.

In some embodiments, the amino acids are non-naturally occurring amino acids, and their analogs.

As used herein, the term "amino acid equivalent" refers to compounds which depart from the structure of the naturally occurring amino acids, but which have substantially the structure of an amino acid, such that they can be substituted within a peptide which retains its activity, e.g., biological activity. Thus, for example, in some embodiments amino acid equivalents can also include amino acids having side chain modifications or substitutions, and also include related organic acids, amides or the like.

In some embodiments, the amino acids are non-naturally occurring amino acids, and their analogs.

Any amino acids derivatives known to one of the skills in the art can be used to make the peptide fragments of the invention (e.g. commercially available amino acids derivatives found in the Bachem catalog). For example, the following natural or non-natural amino acids can be used in making the peptide fragments of the invention: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, homocysteine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine (3-mercapto-D-valine), ornithine, citruline, alpha-methyl-alanine, para-benzoylphenylalanine, para-aminophenylalanine, p-fluorophenylalanine, phenylglycine, propargylglycine, sarcosine, and tert-butylglycine), diaminobutyric acid, 7-hydroxy-tetrahydroisoquinoline carboxylic acid, naphthylalanine, biphenylalanine, cyclohexylalanine, amino-isobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, and derivatives thereof. One of skill in the art would know that this definition includes, D- and L-amino acids, alpha- and beta-amino acids, chemically modified amino acids, naturally occurring non-proteogenic amino acids, rare amino acids, and chemically synthesized compounds that have properties known in the art to be characteristic of an amino acid. As used herein, the term "proteogenic" indicates that the amino acid can be incorporated into a protein in a cell through well-known metabolic pathways.

In some embodiments, the peptide comprises at least one (e.g., 1, 2, 3, 4, 5, 6, 7, 8, 9, 10 or more) amino acid selected from the group comprising homocysteine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine (3-mercapto-D-valine), ornithine, citruline, alpha-methyl-alanine, para-benzoylphenylalanine, para-amino phenylalanine, p-fluorophenylalanine, phenylglycine, propargylglycine, sarcosine, and tert-butylglycine), diaminobutyric acid, 7-hydroxy-tetrahydroisoquinoline carboxylic acid, naphthylalanine, biphenylalanine, cyclohexylalanine, amino-isobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, and derivatives thereof. In some embodiments, the peptide comprises at least one (e.g., 1, 2, 3, 4, 5, 6, 7, 8, 9, 10 or more) amino acid selected from any amino acid known to one of ordinary skill in the art.

In some embodiments, the peptide comprises at least one (e.g., 1, 2, 3, 4, 5, 6, 7, 8, 9, 10 or more) D-amino acids. In some aspects, all 17 amino acid residues of SEQ ID NO: 1 are D-amino acids. D-amino acid can be present at any position in the peptide, for example reading from the N-terminal at position 1, 2, 3, 4, 5, 6, 7, 8, 9, 10, 11, 12, 13, 14, 15, 16, and/or 17 of SEQ ID NO: 1. When more than one D-amino acid is present in a peptide, they can be positioned next to or not next to each other. In other aspects, all amino acid residues of SEQ ID NO: 4 or SEQ ID NO:5 are D-amino acids. D-amino acid can be present at any position in the peptide, for example reading from the N-terminal at position 1, 2, 3, 4, 5, 6, 7, 8, 9, 10, 11, 12, 13, 14, 15, 16, 17, 18, 19, 20, 21, 22, and/or 23 of SEQ ID NO: 4 or SEQ ID NO:5. When more than one D-amino acid is present in a peptide, they can be positioned next to or not next to each other.

The peptides of the invention can also comprise one or more (e.g., 1, 2, 3, 4, 5, 6, 7, 8, 9, 10 or more) of beta-amino acids. Beta-amino acid can be present at any position in the peptide, for example reading from the N-terminal at position 1, 2, 3, 4, 5, 6, 7, 8, 9, 10, 11, 12, 13, 14, 15, 16, and/or 17. In some aspects all 17 amino acid residues of the SEQ ID NO: 1 are substituted with beta-amino acids. When more than one beta-amino acid is present in a peptide, they can be positioned next to each other or next to another amino acid. In other aspects all amino acid residues of SEQ ID NO: 4 or SEQ ID NO:5 are substituted with beta-amino acids. When more than one beta-amino acid is present in a peptide, they can be positioned next to each other or next to another amino acid.

In some embodiments, the amino acids comprise natural and non-natural amino acids bearing a conventional amino protecting group (e.g. acetyl or benzyloxycarbonyl), natural and unnatural amino acids protected at the carboxy terminus (e.g. as a ($C_1$-$C_6$ alkyl, phenyl or benzyl ester or amide; or as an alpha-methylbenzyl amide), as well as natural and unnatural amino acids protected at side chain reactive groups. Suitable protecting groups are known to those skilled in the art (See for example, Greene, T. W and Wutz, P. G. M. Protecting Groups In Organic Synthesis, 2nd edition, John Wiley & Sons, Inc., New York (1991) and references cited therein). In some embodiments, the amino acids comprise natural and non-natural amino acids bearing a capping group. In some embodiments, the capping group is a protecting group. In some embodiment, the capping group is not a protecting group. In some embodiments, the capping group results from chemical modifications. In some embodiments, the chemical modification is the acylation of sidechains (e.g. on amines). In some embodiments, the chemical modification is the alkylation of an alcohol. In some embodiments, the chemical modification is the alkylation of an amine.

It is known in the art that limited modifications can be made to a peptide without destroying its biological function. Thus, in some embodiments one can modify the peptides of the present invention, such as the SEQ ID NO: 1, SEQ ID NO:2, SEQ ID NO: 4 or SEQ ID NO:5. Such modifications should be made in a way that does not substantially alter the function of the peptide fragment when compared to a fragment of the wild type peptide. As discussed above, in some embodiments, the modified peptide fragments retain at least 60% of the activity of the wild-type peptide, in some embodiments, they retain at least 70%, at least 80%, at least 90%, at least 95%, or more of the activity of the wild-type peptide of SEQ ID NO: 1, namely, the capacity to inhibit, reduce or block binding of albumin to FcRn in an assay. The modified peptide can also be more active than the corresponding wild-type peptide. Also as discussed above, in some embodiments, the modified peptide fragments retain at least 60% of the activity of the wild-type peptide, in some embodiments, they retain at least 70%, at least 80%, at least 90%, at least 95%, or more of the activity of the wild-type peptide of SEQ ID NO: 4 or SEQ ID NO:5, namely, the capacity bind to a non-IgG and non-albumin competitive site on a FCRN alpha 3 domain.

For example, a bioassay of FcRn dependent albumin transcytosis using madin darby canine kidney cells transfected with human FcRn and beta-2-microglobulin can be used measure the binding capacity of the modified peptides, and the peptide of SEQ ID NO: 1 can be used as a positive standard. If the binding capacity is not less than about 75% of the binding capacity of SEQ ID NO: 1, the peptide is considered capable of inhibiting the binding of albumin to FcRn. In some aspects, if the binding capacity is not less than 80%, 90% or 95%, the peptide is considered capable of inhibiting the binding of albumin to FcRn.

The term "peptide bond" means a covalent amide linkage formed by loss of a molecule of water between the carboxyl group of one amino acid and the amino group of a second amino acid.

In some embodiments, one can also use a "peptide bond replacement" to make a more stable peptide. The term "peptide bond replacement", as used herein, refers to a linkage, such as a covalent linkage, between the carboxyl group of one amino acid and the amino group of a second amino acid. Exemplary peptide bond replacements include, but are not limited to, urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, and olefinic group. In some embodiments, the peptide bond replacement comprises hydroxyethyl isosteres, dihydroxyethyl isosteres (e.g., those found in HIV protease and other protease inhibitors). One or more of the peptide bonds in the peptide fragments of the invention can be replaced with a peptide bond replacement. The peptide bond can also be replaced by a linker.

The choice of including a modification into a peptide of the present invention depends, in part, on the desired characteristics of the peptide. For example, the incorporation of one or more (D)-amino acids can confer increasing stability on the peptide in vitro or in vivo, thus affecting shelf-life, serum half-life or bioavailability. The incorporation of one or more (D)-amino acids also can increase or decrease the binding activity of the peptide as determined, for example, using the binding assays by methods well known in the art. In some cases it is desirable to design a peptide which retains activity for a longer period of time, for example, when designing a peptide to administer to a subject. In these cases, the incorporation of one or more (D)-amino acids or replacement of amide backbone linkages in the peptide can stabilize the peptide against endogenous peptidases in vivo, thereby prolonging the subject's exposure to the peptide.

Modification and Derivation of Peptides

In some embodiments, the peptides described herein are peptidomimetics. As used herein, the term "peptidomimetic" refers to a non-peptide or peptide-like molecule that is a topological analog of the corresponding peptide or has the activity of the peptide on which it is structurally based. See, for example, Goodman and Ro, *Peptidomimetics for Drug Design*, in "Burger's Medicinal Chemistry and Drug Discovery", Vol. 1 (ed. M. E. Wolff; John Wiley & Sons 1995), pages 803-861. Peptidomimetics provide various advantages over a peptide, including that a peptidomimetic can be more stable during passage through the digestive tract and, therefore, useful for oral administration. A peptidomimetic can comprise a non-peptide backbone used in the art in the design of peptidomimetics, such as a glucose scaffold, a pyrrolidine scaffold, a steroidal scaffold, a benzodiazepine scaffold, and the like.

A variety of peptidomimetics are known in the art including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an α-methylated amino acid; α,α-dialkylglycine or α-aminocycloalkane carboxylic acid; an $N^\alpha$—$C^\alpha$ cyclized amino acid; an $N^\alpha$-methylated amino acid; α, β- or γ-amino cycloalkane carboxylic acid; an α,β-unsaturated amino acid; a β,β-dimethyl or β-methyl amino acid; α,β-substituted-2,3-methano amino acid; an N—$C^\delta$ or $C^\alpha$—$C^\delta$ cyclized amino acid; a substituted proline or another amino acid mimetic. A peptidomimetic which mimics peptide secondary structure can contain, for example, a nonpeptidic β-turn mimic; γ-turn mimic; mimic of β-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylene-sulfoxide bond; methylene ether bond; ethylene bond; thioamide bond; transolefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

Methods for identifying peptidomimetics are well known in the art and include, for example, the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). This structural depository is continually updated as new crystal structures are determined and can be screened for compounds having suitable shapes, for example, the same shape as a peptide described herein. Another database, the Available Chemicals Directory (Molecular Design Limited, Information Systems; San Leandro Calif.), contains about 100,000 compounds that are commercially available and also can be searched to identify potential peptidomimetics of a peptide describe herein. Methods of preparing peptidomimetics are described for example in Methods in Molecular Medicine: Peptidomimetics Protocols, W. M. Kazmierski (Ed.) (1999) $1^{st}$ Edition, Humana Press, Totowa, N.J.

A wide variety of ligands or tags can be coupled with the peptides described herein. In some embodiments, ligands include naturally occurring molecules, in some embodiments recombinant or synthetic molecules. Exemplary ligands include, but are not limited to, polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG, e.g., PEG-2K, PEG-5K, PEG-10K, PEG-12K, PEG-15K, PEG-20K, PEG-40K), MPEG, [MPEG]2, polyvinyl alcohol (PVA), polyurethane, poly(2-ethylacryllic acid), N-isopropylacrylamide polymers, polyphosphazine, polyethylenimine, cationic groups, spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, thyrotropin, melanotropin, lectin, glycoprotein, surfactant protein A, mucin, glycosylated polyaminoacids, transferrin, bisphosphonate, polyglutamate, polyaspartate, aptamer, asialofetuin, hyaluronan, procollagen, immunoglobulins (e.g., antibodies), insulin, transferrin, albumin, sugar-albumin conjugates, intercalating agents (e.g., acridines), cross-linkers (e.g. psoralen, mitomycin C), porphyrins (e.g., TPPC4, texaphyrin, Sapphyrin), polycyclic aromatic hydrocarbons (e.g., phenazine, dihydrophenazine), artificial endonucleases (e.g., EDTA), lipophilic molecules (e.g, steroids, bile acids, cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine), peptides (e.g., an alpha helical peptide, amphipathic peptide, RGD peptide, cell permeation peptide, endosomolytic/fusogenic peptide), alkylating agents, phosphate, amino, mercapto, polyamino, alkyl, substituted alkyl, radiolabeled markers (e.g. iodophenylalanine, Tc99m, iodination), enzymes, haptens (e.g. biotin), transport/absorption facilitators (e.g., naproxen, aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, AP, antibodies, hormones and hormone receptors, lectins, carbohydrates, multivalent carbohydrates, vitamins (e.g., vitamin A, vitamin E, vitamin K, vitamin B, e.g., folic acid, B12, riboflavin, biotin and pyridoxal), vitamin cofactors, lipopolysaccharide, an activator of p38 MAP kinase, an activator of NF-κB, taxon, vincristine, vinblastine, cytochalasin, nocodazole, japlakinolide, latrunculin A, phalloidin, swinholide A, indanocine, myoservin, tumor necrosis factor alpha (TNFalpha), interleukin-1 beta, gamma interferon, natural or recombinant low density lipoprotein (LDL), natural or recombinant high-density lipoprotein (HDL), bovine serum albumin (BSA), ovalbumin, keyhole limpet hemocyanin (KLH), and a cell-permeation agent (e.g., a.helical cell-permeation agent).

In some embodiments, the peptide of the invention is conjugated with a label/tag, such as a fluorescent label or a biotin label. Without wishing to be bound by theory, such labeling allows one to easily track the peptide, if necessary or to assist in purification of the peptide fragment.

As used herein, the term "label" refers to a composition capable of producing a detectable signal indicative of the presence of a target. Suitable labels include fluorescent molecules, radioisotopes, nucleotide chromophores, enzymes, substrates, chemiluminescent moieties, magnetic particles, bioluminescent moieties, and the like. As such, a label is any composition detectable by spectroscopic, photochemical, biochemical, immunochemical, electrical, optical or chemical means needed for the methods and devices described herein. For example, the peptides can be labeled with a detectable tag which can be detected using an antibody specific to the label.

Exemplary fluorescent labeling reagents include, but are not limited to, Hydroxycoumarin, Succinimidyl ester, Aminocoumarin, Methoxycoumarin, Cascade Blue, Hydrazide, Pacific Blue, Maleimide, Pacific Orange, Lucifer yellow, NBD, NBD-X, R-Phycoerythrin (PE), a PE-Cy5 conjugate (Cychrome, R670, Tri-Color, Quantum Red), a PE-Cy7 conjugate, Red 613, PE-Texas Red, PerCP, Peridinin chlorophyll protein, TruRed (PerCP-Cy5.5 conjugate), FluorX, Fluoresceinisothyocyanate (FITC), BODIPY-FL, TRITC, X-Rhodamine (XRITC), Lissamine Rhodamine B, Texas Red, Allophycocyanin (APC), an APC-Cy7 conjugate, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, Alexa Fluor 750, Alexa Fluor 790, Cy2, Cy3, Cy3B, Cy3.5, Cy5, Cy5.5 or Cy7.

In another example, a monomer having a chemical group suitable for taking part in Click Chemistry reaction can be incorporated, e.g., an azide or alkyne group. In a subsequent operation, i.e., after incorporation of the precursor monomer into the peptide, a ligand having complementary chemical group, e.g., an alkyne or azide can be attached to the precursor monomer by coupling the alkyne and the azide together.

In some embodiments, the N terminal amino group is linked with R', C(O)R$^1$, C(O)OR$^1$, or C(O)NHR$^1$, wherein R$^1$ is a linear or branched C$_1$-C$_6$ alkyl, linear or branched C$_2$-C$_6$ alkenyl, aryl, heteroaryl, cyclyl, heterocyclyl, each of which can be optionally substituted.

In some embodiments, the C-terminal carboxyl oxygen is linked with R$^2$, wherein R$^2$ is a linear or branched C$_1$-C$_6$ alkyl, linear or branched C$_2$-C$_6$ alkenyl, aryl, heteroaryl, cyclyl, heterocyclyl, each of which can be optionally substituted.

In some embodiments, an amino group in at least one amino acid side chain is linked with R$^3$, C(O)R$^3$, C(O)OR$^3$, or C(O)NHR$^3$, wherein R$^3$ is a linear or branched C$_1$-C$_6$ alkyl, linear or branched $C_2$-$C_6$ alkenyl, aryl, heteroaryl, cyclyl, heterocyclyl, each of which can be optionally substituted.

In some embodiments, a carboxyl oxygen in at least one amino acid side chain is linked with $R^4$, $C(O)R^4$, $C(O)OR^4$, or $C(O)NHR^4$, wherein $R^4$ is a linear or branched $C_1$-$C_6$ alkyl, linear or branched $C_2$-$C_6$ alkenyl, aryl, heteroaryl, cyclyl, heterocyclyl, each of which can be optionally substituted.

Linkers can be simple, for example, 1-10 amino acid linkers, comprising, e.g., glycine or glycine and serine residues. The examples used a three glycine linker.

Other examples of useful linkers include the following:

| Name | Description | Sequence encoding amino acid linker | SEQ ID NO: |
|---|---|---|---|
| BBa_J176131 | PLrigid | gaagctgctgcaagagaagctgcagctagggagg ctgcagctagggaggctgctgcaaga | 97 |
| BBa_J18920 | 2aa GS linker | ggcagc | |
| BBa_J18921 | 6aa [GS]x linker | ggtagcggcagcggtagc | 98 |
| BBa_J18922 | 10aa [GS]x linker | ggtagcggcagcggtagcggtagcggcagc | 99 |
| BBa_K105012 | 10 aa flexible protein domain linker | ggtgaaaatagtattttcaatctggtggt | 100 |
| BBa_K133132 | 8 aa protein domain linker | tccgcttgttactgtgagctttcc | 101 |
| BBa_K157009 | Split fluorophore linker; Freiburg standard | cgaccagcctgtaagattccaaatgacctgaagcag aaagttatgaatcac | 102 |
| BBa_K157013 | 15 aa flexible glycine-serine protein domain linker; Freiburg standard | ggtggaggaggttctggaggcggtggaagtggtg gcggaggtagc | 103 |
| BBa_K243004 | Short Linker (Gly-Gly-Ser-Gly) (SEQ ID NO: 92) | ggtggttctggt | 104 |
| BBa_K243005 | Middle Linker (Gly-Gly-Ser-Gly) x2 (SEQ ID NO: 93) | ggtggttctggtggtggttctggt | 105 |
| BBa_K243006 | Long Linker (Gly-Gly-Ser-Gly)x3 (SEQ ID NO: 94) | ggtggttctggtggtggttctggtggtggttctggt | 106 |
| BBa_K243029 | GSAT Linker | ggtggttctgccggtggctccggttctggctccagc ggtggcagctctggtgcgtccggcacgggtactgc gggtggcactggcagcggttccggtactg gctctggc | 107 |
| BBa_K243030 | SEG | ggtggttctggcggcggttctgaaggtggcggctcc gaaggcggcggcagcgagggcggtggtagcgaa ggtggtggctccgagggtggcggttccggcg gcggtagc | 108 |
| BBa_K404300 | SEG-Linker | ggtggttctggcggcggttctgaaggtggcggctcc gaaggcggcggcagcgagggcggtggtagcgaa ggtggtggctccgagggtggcggttccggcg gcggtagc | 109 |
| BBa_K404301 | GSAT-Linker | ggtggttctgccggtggctccggttctggctccagc ggtggcagctctggtgcgtccggcacgggtactgc gggtggcactggcagcggttccggtactg gctctggc | 110 |
| BBa_K416001 | (Gly4Ser)3 Flexible Peptide Linker (SEQ ID NO: 95) | ggtggaggaggctctggtggaggcggtagcggag gcggagggtcg | 111 |
| BBa_K648005 | Short Fusion Protein Linker: GGSG (SEQ ID NO: 92) with standard 25 prefix/suffix | ggtggttctggt | 112 |
| BBa_K648006 | Long 10AA Fusion Protein Linker with Standard 25 Prefix/Suffix | ggtgaaaatttgtattttcaatctggtggt | 113 |
| BBa_K648007 | Medium 6AA Fusion Protein Linker: GGSGGS (SEQ ID NO: 96) with Standard 25 Prefix/Suffix | ggaggttcaggaggcagc | 114 |

Linkers

In some embodiments, the peptides form fusion peptides, such as dimeric peptides, for example cyclic dimeric peptides that are formed using "linkers." The peptides can also be fused to other peptides or proteins using linkers. Linkers are typically short peptide sequences that occur between protein domains. Linkers are often composed of flexible residues like glycine and serine so that the adjacent protein domains are free to move relative to one another. Longer linkers are used when it is necessary to ensure that two adjacent domains do not sterically interfere with one another.

Conjugation of Peptides

The peptide fragments of the invention can also be conjugated to either other peptides or other molecules to tailor, for example, the bioavailability, serum half-life or shelf-life of the peptide fragments, immunogenicity, tolerance by human body, or to affect the solubility of the peptides in pharmaceutically acceptable carriers.

Many strategies are known in the art for conjugating peptides to peptides and other molecules. For example, Hermanson, G. T., *Bioconjugate Techniques,* 2nd Ed., Academic Press (2008) and Niemeyr, C. M., *Bioconjugation Protocols: Strategies and Methods* (*Methods in Molecular Biology*), Humana Press (2004) provide a number of methods and techniques for conjugating peptides to other molecules. Contents of both of these are herein incorporated by reference in their entirety for all purposes. For a review of site-specific introduction of non-natural amino acids into peptides for conjugation see A. J. de Graaf, et al., *Biocoju-* gate Chemistry (2009) 20(7):1281-1295, contents of which are herein incorporated in its entirety. Int. Pat. App. Pub. No.: WO92/13095, contents of which are herein incorporated in its entirety, describes methods for PEGylation of peptides.

Peptide Synthesis

The polypeptides of the present invention can be synthesized chemically by e.g., solution or solid-phase peptide synthesis, or semi-synthesis in solution beginning with protein fragments coupled through conventional solution methods, as described by Dugas et al (1981). Alternatively, "SYN1753", "SYN3258", "SYN514", SYN515", and "SYN531" polypeptides, as well as their analogs, derivatives and fragments as described herein can be synthesized using e.g., recombinant methods.

Accordingly, various embodiments of the present invention also provide for nucleic acids encoding the isolated polypeptide that specifically blocks the interaction between neonatal FcRN and albumin, vectors comprising the nucleic acids, as well as cells comprising the vectors.

Peptides can be chemically synthesized using methods well known in the art. See for example, Merrifield et al., J. Am. Chem. Soc. 85:2149 (1964); Bodanszky, M., Principles of Peptide Synthesis, Springer-Verlag, New York, N.Y. (1984); Kimmerlin, T. and Seebach, D. J. Pept. Res. 65:229-260 (2005); Nilsson et al., Annu. Rev. Biophys. Biomol. Struct. (2005) 34:91-118; W. C. Chan and P. D. White (Eds.) Fmoc Solid Phase Peptide Synthesis: A Practical Approach, Oxford University Press, Cary, N.C. (2000); N. L. Benoiton, Chemistry of Peptide Synthesis, CRC Press, Boca Raton, Fla. (2005); J. Jones, Amino Acid and Peptide Synthesis, 2nd Ed, Oxford University Press, Cary, N.C. (2002); and P. Lloyd-Williams, F. Albericio, and E. Giralt, Chemical Approaches to the synthesis of peptides and proteins, CRC Press, Boca Raton, Fla. (1997), contents of all of which are herein incorporated by reference. Peptide derivatives can also be prepared as described in U.S. Pat. Nos. 4,612,302; 4,853,371; and 4,684,620, and U.S. Pat. App. Pub. No. 2009/0263843, contents of all which are herein incorporated by reference. Alternatively, a peptide can be synthesized using standard solution methods (see, for example, Bodanszky, 1984). Newly synthesized peptides can be purified, for example, by high performance liquid chromatography (HPLC), and can be characterized using, for example, mass spectrometry, mononuclear and multi-nuclear magnetic resonance, or amino acid sequence analysis.

The peptides of the present invention can be synthesized by using well known methods including recombinant methods and chemical synthesis. Recombinant methods of producing a peptide through the introduction of a vector including nucleic acid encoding the peptide into a suitable host cell is well known in the art, such as is described in Sambrook et al., Molecular Cloning: A Laboratory Manual, 2d Ed, Vols 1 to 8, Cold Spring Harbor, N.Y. (1989); M. W. Pennington and B. M. Dunn, Methods in Molecular Biology: Peptide Synthesis Protocols, Vol 35, Humana Press, Totawa, N.J. (1994), contents of both of which are herein incorporated by reference. Peptides can also be chemically synthesized using methods well known in the art. See for example, Merrifield et al., J. Am. Chem. Soc. 85:2149 (1964); Bodanszky, M., Principles of Peptide Synthesis, Springer-Verlag, New York, N.Y. (1984); Kimmerlin, T. and Seebach, D. J. Pept. Res. 65:229-260 (2005); Nilsson et al., Annu. Rev. Biophys. Biomol. Struct. (2005) 34:91-118; W. C. Chan and P. D. White (Eds.) Fmoc Solid Phase Peptide Synthesis: A Practical Approach, Oxford University Press, Cary, N.C. (2000); N. L. Benoiton, Chemistry of Peptide Synthesis, CRC Press, Boca Raton, Fla. (2005); J. Jones, Amino Acid and Peptide Synthesis, $2^{nd}$ Ed, Oxford University Press, Cary, N.C. (2002); and P. Lloyd-Williams, F. Albericio, and E. Giralt, Chemical Approaches to the synthesis of peptides and proteins, CRC Press, Boca Raton, Fla. (1997), contents of all of which are herein incorporated by reference. Peptide derivatives can also be prepared as described in U.S. Pat. Nos. 4,612,302; 4,853,371; and 4,684,620, and U.S. Pat. App. Pub. No. 2009/0263843, contents of all which are herein incorporated by reference. Systems for cloning and expressing polypeptide of the invention include various microorganisms and cells that are well known in recombinant technology. These include, for example, various strains of E. coli, Bacillus, Streptomyces, and Saccharomyces, as well as mammalian, yeast and insect cells. The "SYN1753", "SYN3258", "SYN514", SYN515" and "SYN531" polypeptides can be produced as a polypeptide or fusion protein. Suitable vectors for producing peptides are known and available from private and public laboratories and depositories and from commercial vendors. See Sambrook et al, (1989). Recipient cells capable of expressing the gene product are then transfected. The transfected recipient cells are cultured under conditions that permit expression of the recombinant gene products, which are recovered from the culture. Host mammalian cells, such as Chinese Hamster ovary cells (CHO) or COS-1 cells, can be used. These hosts can be used in connection with poxvirus vectors, such as vaccinia or swinepox. Suitable non-pathogenic viruses that can be engineered to carry the synthetic gene into the cells of the host include poxviruses, such as vaccinia, adenovirus, retroviruses and the like. A number of such non-pathogenic viruses are commonly used for human gene therapy, and as carrier for other vaccine agents, and are known and selectable by one of skill in the art. The selection of other suitable host cells and methods for transformation, culture, amplification, screening and product production and purification can be performed by one of skill in the art by reference to known techniques (see, e.g., Gething et al, 1981).

A purified "SYN1753", "SYN3258", "SYN514", SYN515" and "SYN531" polypeptide fragment, analog and/or derivative refers to a composition isolated from other components, wherein "SYN1753", "SYN3258", "SYN514", SYN515" and "SYN531" polypeptides, polypeptide fragment, analog and/or derivative is purified to any degree relative to its naturally-obtainable state. An isolated or purified peptide, therefore, also refers to a peptide free from the environment in which it may naturally occur. Generally, "purified" will refer to a "SYN1753", "SYN3258", "SYN514", SYN515" and "SYN531" polypeptides, fragment, analog and/or derivative composition that has been subjected to fractionation to remove various other components, and which composition substantially retains its expressed biological activity. Where the term "substantially purified" is used, this designation will refer to a composition in which the "SYN1753", "SYN3258", "SYN514", SYN515", and "SYN531" polypeptide, fragment, analog and/or derivative forms the major component of the composition, such as constituting about 50%, about 60%, about 70%, about 80%, about 90%, about 95%, or more of the proteins in the composition.

In one embodiment the peptide of the invention is isolated and/or purified. Protein purification techniques are well known to those of skill in the art. These techniques involve, at one level, the homogenization and crude fractionation of the cells, tissue or organ to polypeptide and non-polypeptide fractions. The peptide of interest may be further purified using chromatographic and electrophoretic techniques to achieve partial or complete purification (or purification to homogeneity). Analytical methods particularly suited to the preparation of a pure peptide are ion-exchange chromatography, gel exclusion chromatography, polyacrylamide gel electrophoresis, affinity chromatography, immunoaffinity chromatography and isoelectric focusing. An example of receptor protein purification by affinity chromatography is disclosed in U.S. Pat. No. 5,206,347, the entire text of which is incorporated herein by reference. A particularly efficient method of purifying peptides is fast performance liquid chromatography (FPLC) or even high performance liquid chromatography (HPLC).

Various techniques suitable for use in protein purification are known to those of skill in the art and include, for example, precipitation with ammonium sulfate, polyethylene glycol (PEG), antibodies and the like, or by heat denaturation, followed by: centrifugation; chromatography steps such as ion exchange, gel filtration, reverse phase, hydroxyapatite and affinity chromatography; isoelectric focusing; gel electrophoresis; and combinations of these and other techniques. As is generally known in the art, it is believed that the order of conducting the various purification steps may be changed, or that certain steps may be omitted, and still result in a suitable method for the preparation of a substantially purified protein or peptide.

Various methods for quantifying the degree of purification of a "SYN1753", "SYN3258", "SYN514", SYN515" and "SYN531" polypeptide, fragment, analog and/or derivative are known to those of skill in the art and include, for example, determining the specific activity of an active fraction, or assessing the amount of polypeptides within a fraction by SDS/PAGE analysis. There is no general requirement that the "SYN1753", "SYN3258", "SYN514", SYN515" and "SYN531" polypeptide, fragment, analog and/or derivative be provided in the most purified state. Indeed, it is contemplated that less purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

Affinity chromatography is a chromatographic procedure that relies on the specific affinity between a substance to be isolated and a molecule to which it can specifically bind (e.g., a receptor-ligand interaction). The column material is synthesized by covalently coupling one of the binding partners to an insoluble matrix. The column material is then able to specifically adsorb the substance from the solution. Elution occurs by changing the conditions to those in which binding will not occur (e.g., altered pH, ionic strength, temperature, etc.). The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand.

Synthesis of beta-amino acids and their derivatives are described for example in Basler B, Schuster O, and Bach T. *Conformationally constrained beta-amino acid derivatives by intramolecular [2+2]-photocycloaddition of a tetronic acid amide and subsequent lactone ring opening*. J. Org. Chem. (2005) 70(24):9798-808; and Murray J K, Farooqi B, Sadowsky J D, Scalf M, Freund W A, Smith L M, Chen J, Gellman S H. *Efficient synthesis of a beta peptide combinatorial library with microwave irradiation*. JACS (2005) 127(38):13271-80.

In some embodiments, the peptides of the present invention comprise a constrained secondary conformation. As used herein, the terms "constrained secondary structure," "stabilized" and "conformationally stabilized" indicate that at least one peptide bond comprising the peptide is not able to rotate freely but instead is maintained in a relatively fixed structure. Various methods for constraining the secondary structure of a peptide are well known in the art. For example, a peptide can be stabilized into a constrained secondary structure by incorporating the peptide into a larger peptide sequence that forms a known secondary structure. For example, a peptide of the present invention can be stabilized by incorporating it into a sequence that forms a helix such as an alpha helix or a triple helix, according to methods described, for example, by Dedhar et al., J. Cell. Biol. 104:585 (1987); by Rhodes et al., Biochem 17:3442 (1978); and by Carbone et al., Immunol 138:1838 (1987), each of which is incorporated herein by reference. Additionally, the peptides can be incorporated into larger linear, cyclic or branched peptides, so long as their biological activity is retained.

One method for constraining the secondary structure of a newly synthesized linear peptide is to cyclize the peptide using any of various methods well known in the art. For example, a cyclic peptide can be prepared or may result from the formation of disulfide bridges between two cysteine residues in a sequence. In another example, a cyclized peptide of the present invention can be prepared by forming a peptide bond between nonadjacent amino acid residues as described, for example, by Schiller et al., Int. J. Pept. Prot. Res. 25:171 (1985), which is incorporated herein by reference. Peptides can be synthesized on the Merrifield resin by assembling the linear peptide chain using Na-Fmoc-amino acids and Boc and tertiary-butyl proteins. Following the release of the peptide from the resin, a peptide bond can be formed between the amino and carboxyl termini.

A newly synthesized linear peptide can also be cyclized by the formation of a bond between reactive amino acid side chains. For example, a peptide containing a cysteine-pair can be synthesized and a disulfide bridge can be formed by oxidizing a dilute aqueous solution of the peptide with $K_3[Fe(CN)_6]$. Alternatively, a lactam such as an epsilon-(gamma-glutamyl)-lysine bond can be formed between lysine and glutamic acid residues, a lysine or leucine bond can be formed between lysine and leucine residues or a dityrosine bond can be formed between two tyrosine residues. A peptide can be cyclized by adding a cysteine residue at each of the N-terminal and C-terminal. Methods for forming these and other bonds are well known in the art and are based on well-known rules of chemical reactivity (Morrison and Boyd, Organic Chemistry, 6th Ed. (Prentice Hall, 1992), which is herein incorporated by reference).

The Polyethylene glycol (PEG) can be conjugated to the peptide compounds as described herein. PEGylation can be achieved by incubation of a reactive derivative of PEG with the target macromolecule. The conjugation to PEG can be performed either enzymatically or chemically, the methods of which are well established in the art (Chapman, 2002; Veronese and Pasut, 2005). With PEGylation the total size of a peptide can be increased, which reduces the chance of renal filtration and can increase the circulating half-life of the peptide. PEGylation further protects peptides from proteolytic degradation and slows the clearance from the blood. In addition, PEGylation reduces immunogenicity and increases solubility of macromolecules (e.g., peptides). The improved pharmacokinetics by the addition of PEG is due to several different mechanisms: increase in size of the molecule, protection from proteolysis, reduced antigenicity, and the masking of specific sequences from cellular receptors. For example, in the case of antibody fragments (Fab), a 20-fold increase in plasma half-life has been achieved by PEGylation (Chapman, 2002).

PEG moieties useful with the compositions and methods described herein include PEG polymers, derivatives and PEG lipids. PEG polymers can be e.g., linear, branched or multi-armed, among others. The PEG conjugate according to the present invention may be of any molecular weight, for example, the molecular weight may be between 500 and 100,000 Da, between 500 and 60,000 Da, between 1000 and 40,000 Da, or between 5000 and 40,000 Da. PEGs having molecular weights of 10000 Da, 20000 Da, 30000 Da or 40000 Da may be used with the peptides described herein.

The term "fusion protein" as used herein refers to a recombinant protein of two or more proteins. Fusion proteins can be produced, for example, by a nucleic acid sequence encoding one protein is joined to the nucleic acid encoding another protein such that they constitute a single open-reading frame that can be translated in the cells into a single polypeptide harboring all the intended proteins. The order of arrangement of the proteins can vary. Fusion proteins can include an epitope tag or a half-life extender. Epitope tags include biotin, FLAG tag, c-myc, hemaglutinin, His6 (SEQ ID NO: 115), digoxigenin, FITC, Cy3, Cy5, green fluorescent protein, V5 epitope tags, GST, β-galactosidase, AU1, AU5, and avidin.

In some aspects of the present invention, certain polypeptides of the present invention are generally used to block the interaction between neonatal Fc receptor (FCRN) and albumin and to thereby treat diseases and conditions as described herein. In certain embodiments, these polypeptides block or reduce the interaction by about 10-98%, for example, 25-95%, 30-95%, 40-95%, 50-95%, 60-95%, 60-98%, 75-98%, for example about 10%, 15%, 20%, 25%, 30, 34, 40, 45, 50, 55, 60, 65, 70, 75, 80, 85, 90, 95, 96, 97, 98, or about 99%.

The normal range for serum albumin level is about 3.4-5.4 grams per deciliter (g/dL). In some aspects, an amount of albumin binding is blocked by certain polypeptides of the present invention, resulting in a clinically and/or therapeutically significant reduction in serum albumin levels, which can be readily determined by one of ordinary skill in the art, or for example, by a reduction in the symptoms of the diseases or conditions. In other aspects, the serum albumin level is normalized by the FCRN and polypeptide interaction.

In other aspects of the present invention, certain polypeptides of the present invention are generally used to bind to a non-IgG and non-albumin competitive site on a FCRN alpha 3 domain, and thereby to tract neonatal Fc receptor FCRN without inhibiting IgG or albumin binding or function.

The term gene "expression" as used herein refers to a process by which a gene produces the polypeptide. The process includes any manifestation of the functional presence of the gene within the cell including, without limitation, gene knockdown as well as both transient expression and stable expression. It includes, without limitation, the translation of such mRNA into polypeptide(s), as well as any processes which regulate either transcription or translation, such as SEQ ID NO:1, SEQ ID NO:2, SEQ ID NO:4, SEQ ID NO:5 or conservatively substituted variants thereof or fusion proteins comprising SEQ ID NO:1, SEQ ID NO:2, SEQ ID NO:4, or SEQ ID NO:5.

As used herein, the terms "treat" or "treatment" refer to therapeutic treatment, wherein the object is to reduce one or more symptom of the disease or condition or slow down (lessen) an undesired physiological change or disorder. The term "prevention" refers to prophylactic or preventative measures, wherein the object is to prevent or slow down (lessen) an undesired physiological change or disorder, such as the progression of albumin caused damage in diabetes. Beneficial or desired clinical results of the treatment include, but are not limited to, alleviation of symptoms, diminishment of extent of disease, stabilized (i.e., not worsening) state of disease, delay or slowing of disease progression, amelioration or palliation of the disease state, and remission, whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. In certain embodiments, the mammal is a human subject.

As used herein, a "therapeutically effective amount" refers to an amount effective, at dosages and for periods of time necessary, to achieve the desired therapeutic result. A therapeutic result may be, e.g., lessening of symptoms, prolonged survival, improved mobility, and the like. A therapeutic result need not be a "cure."

As used herein, a "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

As used herein, the term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T. C, G. U. or I) or residue occurs in both sequences to yield the number of matched positions, dividing the number of matched positions by the total number of positions in the comparison window (i.e., the window size), and multiplying the result by 100 to yield the percentage of sequence identity.

The term "substantial identity" as used herein denotes a characteristic of a polynucleotide or amino acid sequence, wherein the polynucleotide or amino acid comprises a sequence that has at least 85% sequence identity, preferably at least 90% to 95% sequence identity, more usually at least 99% sequence identity as compared to SEQ ID NO:1, SEQ ID NO:2, SEQ ID NO:4, or SEQ ID NO:5 by comparing the reference sequence, i.e., SEQ ID NO:1, SEQ ID NO:2, SEQ ID NO:4, or SEQ ID NO:5 to the sequence which can include deletions or additions which total 20 percent or less of the reference sequence over the comparison window. The reference sequence can be a subset of a larger sequence. The term "similarity", when used to describe a polypeptide, is determined by comparing the amino acid sequence and the conserved amino acid substitutes of one polypeptide to the sequence of a second polypeptide.

As used herein, the terms "homologous" or "homologues" are used interchangeably, and when used to describe a polynucleotide or polypeptide, indicates that two polynucleotides or polypeptides, or designated sequences thereof, when optimally aligned and compared, for example using BLAST, version 2.2.14 with default parameters for an alignment (see herein) are identical, with appropriate nucleotide insertions or deletions or amino-acid insertions or deletions, in at least 70% of the nucleotides, usually from about 75% to 99%, and more preferably at least about 98 to 99% of the nucleotides. The term "homolog" or "homologous" as used herein also refers to homology with respect to structure and/or function. With respect to sequence homology, sequences are homologs if they are at least 35%, at least 40%, at least 50%, at least 60 at least 70%, at least 80%, at least 90%, at least 95% identical, at least 97% identical, or at least 99% identical. Determination of homologs of the genes or peptides of the present invention can be easily ascertained by the skilled artisan.

The term "substantially homologous" refers to sequences that are at least 90%, at least 95% identical, at least 96%, identical at least 97% identical, at least 98% identical or at least 99% identical to SEQ ID NO:1, SEQ ID NO:2, SEQ ID NO:4, SEQ ID NO:5 or SEQ ID NO:6.

The homologous sequences typically retain the functionally important amino acid residues, such as outlined in the formula $X_1$-Y-$X_2$-C-$X_3$-$X_4$-W-$X_5$-$X_6$-$X_7$-W-C-$X_8$-$X_9$-V-$X_{10}$-$X_{11}$, wherein $X_1$, $X_2$, $X_3$, $X_4$, $X_5$, $X_6$, $X_7$, $X_8$, $X_9$, $X_{10}$, and $X_{11}$ (SEQ ID NO:7) is each independently selected from any amino acid, and wherein at least $X_{10}$ and $X_{11}$ can be deleted.

In some aspects, $X_1$ is R or a conservative amino acid substitution of R, $X_2$ is F or a conservative amino acid substitution of F, $X_3$ is T or a conservative amino acid substitution of T, $X_4$ is K or a conservative amino acid substitution of K, $X_5$ is H or a conservative amino acid substitution of H, $X_6$ is G or a conservative amino acid substitution of G, $X_7$ is C or a conservative amino acid substitution of C, $X_8$ is E or a conservative amino acid substitution of E, $X_9$ is E or a conservative amino acid substitution of E, $X_{10}$ is G, a conservative amino acid substitution of G, or is deleted, and $X_{11}$ is T, a conservative amino acid substitution of T, or is deleted (embodiment disclosed as SEQ ID NO: 9).

In some aspects $X_1$ is R or a conservative amino acid substitution of R, $X_2$ is F or a conservative amino acid substitution of F, $X_3$ is T or a conservative amino acid substitution of T, $X_4$ is K or a conservative amino acid substitution of K, $X_5$ is K or a conservative amino acid substitution of K, $X_6$ is H or a conservative amino acid substitution of H, $X_7$ is G or a conservative amino acid substitution of G, $X_8$ is E or a conservative amino acid substitution of E, $X_9$ is E or a conservative amino acid substitution of E, $X_{10}$ is G, a conservative amino acid substitution of G, or is deleted, and $X_{11}$ is T, a conservative amino acid substitution of T, or is deleted (an embodiment disclosed as SEQ ID NO: 124).

In some homologs, $X_1$ is R, and/or $X_2$ is F (embodiments disclosed as SEQ ID NOS 10-11). In other homologs, a 2 of 4 combination of wherein $X_1$ is R, $X_2$ is F, $X_7$ is G, and $X_{10}$ is E (embodiments disclosed as SEQ ID NOS 12-13), or a 3 of 4 combination of wherein $X_1$ is R, $X_2$ is F, $X_7$ is G, and $X_{10}$ is E (embodiments disclosed as SEQ ID NOS 12-13), or $X_1$ is R, $X_2$ is F, $X_7$ is G, and $X_{10}$ is E (embodiments disclosed as SEQ ID NOS 12-13).

For example, one can thus create an isolated polypeptide that specifically blocks the interaction between neonatal Fc receptor (FCRN) and albumin comprising at least one peptide subunit consisting of an amino acid sequence that is at least 90% identical to RYFCTKWKHGWCEEVGT (SEQ ID NO:1).

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, for example, by the local homology algorithm of Smith and Waterman (Adv. Appl. Math. 2:482 (1981), which is incorporated by reference herein), by the homology alignment algorithm of Needleman and Wunsch (J. Mol. Biol. 48:443-53 (1970), which is incorporated by reference herein), by the search for similarity method of Pearson and Lipman (Proc. Natl. Acad. Sci. USA 85:2444-48 (1988), which is incorporated by reference herein), by computerized implementations of these algorithms (e.g., GAP, BESTFIT, FASTA, and TFASTA in the Wisconsin Genetics Software Package, Genetics Computer Group, 575 Science Dr., Madison, Wis.), or by visual inspection. (See generally Ausubel et al. (eds.), Current Protocols in Molecular Biology, 4th ed., John Wiley and Sons, New York (1999)).

One example of a useful algorithm is PILEUP. PILEUP creates a multiple sequence alignment from a group of related sequences using progressive, pairwise alignments to show the percent sequence identity. It also plots a tree or dendogram showing the clustering relationships used to create the alignment. PILEUP uses a simplification of the progressive alignment method of Feng and Doolittle (J. Mol. Evol. 25:351-60 (1987), which is incorporated by reference herein). The method used is similar to the method described by Higgins and Sharp (Comput. Appl. Biosci. 5:151-53 (1989), which is incorporated by reference herein). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for determining percent sequence identity and sequence similarity is the BLAST algorithm, which is described by Altschul et al. (J. Mol. Biol. 215:403-410 (1990), which is incorporated by reference herein). (See also Zhang et al., Nucleic Acid Res. 26:3986-90 (1998); Altschul et al., Nucleic Acid Res. 25:3389-402 (1997), which are incorporated by reference herein). Software for performing BLAST analyses is publicly available through the National Center for Biotechnology Information internet web site. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990), supra). These initial neighborhood word hits act as seeds for initiating searches to find longer HSPs containing them. The word hits are then extended in both directions along each sequence for as far as the cumulative alignment score can be increased. Extension of the word hits in each direction is halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff and Henikoff, Proc. Natl. Acad. Sci. USA 89:10915-9 (1992), which is incorporated by reference herein) alignments (B) of 50, expectation (E) of 10, M=5, N=−4, and a comparison of both strands.

In addition to calculating percent sequence identity, the BLAST algorithm also performs a statistical analysis of the similarity between two sequences (see, e.g., Karlin and Altschul, Proc. Natl. Acad. Sci. USA 90:5873-77 (1993), which is incorporated by reference herein). One measure of similarity provided by the BLAST algorithm is the smallest sum probability (P(N)), which provides an indication of the probability by which a match between two nucleotide or amino acid sequences would occur by chance. For example, an amino acid sequence is considered similar to a reference amino acid sequence if the smallest sum probability in a comparison of the test amino acid to the reference amino acid is less than about 0.1, more typically less than about 0.01, and most typically less than about 0.001.

Polypeptides described herein may be cyclic. Cyclization of the polypeptides reduces the conformational freedom of linear peptides and results in a more structurally constrained molecule. Many methods of peptide cyclization are known in the art. For example, "backbone to backbone" cyclization by the formation of an amide bond between the N-terminal and the C-terminal amino acid residues of the peptide. The "backbone to backbone" cyclization method includes the formation of disulfide bridges between two .alpha.-thio amino acid residues (e.g., cysteine, homocysteine). Certain peptides of the present invention include modifications on the N- and C-terminus of the peptide to form a cyclic polypeptide. Such modifications include, but are not limited, to cysteine residues, acetylated cysteine residues, cysteine residues with a NH2 moiety and biotin. Other methods of peptide cyclization are described in Li & Roller, Curr. Top. Med. Chem. 3:325-341 (2002) and U.S. Patent Publication No. U.S. 2005-0260626 A1, which are incorporated by reference herein in their, entirety.

Compositions and Administration

Various embodiment of the present invention also provide for compositions comprising the isolated polypeptide as disclosed herein or a mutant, variant, analog or derivative thereof, or nucleic acids, vectors comprising the nucleic acids, or cells comprising the vectors.

The administration of one or more peptides as disclosed herein or a mutant, variant, analog or derivative thereof, or nucleic acids, or vectors comprising the nucleic acids may be by any suitable means that results in a concentration of the polypeptide that treats the disorder. The compound may be contained in any appropriate amount in any suitable carrier substance, and is generally present in an amount of 1-95%, or 2-75% or 1-50% by weight of the total weight of the composition. The composition may be provided in a dosage form that is suitable for the oral, parenteral (e.g., intravenously or intramuscularly), intraperitoneal, rectal, cutaneous, nasal, vaginal, inhalant, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols. The pharmaceutical compositions may be formulated according to conventional pharmaceutical practice (see, e.g., Remington: The Science and Practice of Pharmacy, 20th edition, 2000, ed. A. R. Gennaro, Lippincott Williams & Wilkins, Philadelphia, and Encyclopedia of Pharmaceutical Technology, eds. J. Swarbrick and J. C. Boylan, 1988-1999, Marcel Dekker, New York, incorporated, herein, by reference in its entirety).

Pharmaceutical compositions according to the invention may be formulated to release the active compound immediately upon administration or at any predetermined time or time period after administration. The latter types of compositions are generally known as controlled release formulations, which include (i) formulations that create substantially constant concentrations of the agent(s) of the invention within the body over an extended period of time; (ii) formulations that after a predetermined lag time create substantially constant concentrations of the agent(s) of the invention within the body over an extended period of time; (iii) formulations that sustain the agent(s) action during a predetermined time period by maintaining a relatively constant, effective level of the agent(s) in the body with concomitant minimization of undesirable side effects associated with fluctuations in the plasma level of the agent(s) (sawtooth kinetic pattern); (iv) formulations that localize action of agent(s), e.g., spatial placement of a controlled release composition adjacent to or in the diseased tissue or organ; (v) formulations that achieve convenience of dosing, e.g., administering the composition once per week or once every two weeks; and (vi) formulations that target the action of the agent(s) by using carriers or chemical derivatives to deliver the therapeutic to a particular target cell type. Administration of the protein in the form of a controlled release formulation is especially preferred for compounds having a narrow absorption window in the gastrointestinal tract or a relatively short biological half-life.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the protein is formulated with appropriate excipients into a pharmaceutical composition that, upon administration, releases the protein in a controlled manner. Examples include single or multiple unit tablet or capsule compositions, oil solutions, suspensions, emulsions, microcapsules, molecular complexes, microspheres, nanoparticles, patches, and liposomes.

As used herein, the phrases "parenteral administration" and "administered parenterally" as used herein mean modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub-capsular, subarachnoid, intraspinal, intracerebrospinal, and intrasternal injection and infusion. The phrases "systemic administration," "administered systemically", "peripheral administration" and "administered peripherally" as used herein mean the administration therapeutic compositions other than directly into a tumor such that it enters the animal's system and, thus, is subject to metabolism and other like processes.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent or encapsulating material, involved in maintaining the activity of or carrying or transporting the subject agents from one organ, or portion of the body, to another organ, or portion of the body. In addition to being "pharmaceutically acceptable" as that term is defined herein, each carrier must also be "acceptable" in the sense of being compatible with the other ingredients of the formulation. The pharmaceutical formulation comprising the one or more peptides as disclosed herein or a mutant, variant, analog or derivative thereof in combination with one or more pharmaceutically acceptable ingredients. The carrier can be in the form of a solid, semi-solid or liquid diluent, cream or a capsule. These pharmaceutical preparations are a further object of the invention. Usually the amount of active compounds is between 0.1-95% by weight of the preparation, preferably between 0.2-20% by weight in preparations for parenteral use and preferably between 1 and 50% by weight in preparations for oral administration. For the clinical use of the methods of the present invention, targeted delivery composition of the invention is formulated into pharmaceutical compositions or pharmaceutical formulations for parenteral administration, e.g., intravenous; mucosal, e.g., intranasal; enteral, e.g., oral; topical, e.g., transdermal; ocular, e.g., via corneal scarification or other mode of administration. The pharmaceutical composition contains a compound of the invention in combination with one or more pharmaceutically acceptable ingredients. The carrier can be in the form of a solid, semi-solid or liquid diluent, cream or a capsule.

The term "pharmaceutically acceptable carriers" is intended to include all solvents, diluents, or other liquid vehicle, dispersion or suspension aids, surface active agents, isotonic agents, thickening or emulsifying agents, preservatives, solid binders, lubricants and the like, as suited to the particular dosage form desired. Typically, such compounds are carried or transported from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its functional derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

The term "pharmaceutical composition" is used herein refer to compositions or formulations that usually comprise an excipient, such as a pharmaceutically acceptable carrier that is conventional in the art and that is suitable for administration to mammals, and preferably humans or human cells. Such compositions can be specifically formulated for administration via one or more of a number of routes, including but not limited to, oral, ocular parenteral, intravenous, intraarterial, subcutaneous, intranasal, sublingual, intraspinal, intracerebroventricular, and the like. In addition, compositions for topical (e.g., oral mucosa, respiratory mucosa) and/or oral administration can form solutions, suspensions, tablets, pills, capsules, sustained-release formulations, oral rinses, or powders, as known in the art are described herein. The compositions also can include stabilizers and preservatives. For examples of carriers, stabilizers and adjuvants, University of the Sciences in Philadelphia (2005) Remington: The Science and Practice of Pharmacy with Facts and Comparisons, 21st Ed.

In certain embodiments, the compounds of the present invention may contain one or more acidic functional groups and, thus, are capable of forming pharmaceutically acceptable salts with pharmaceutically acceptable bases. The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. These may include cations based on the alkali and alkaline earth metals such as sodium, lithium, potassium, calcium, magnesium and the like, as well as nontoxic ammonium, quaternary ammonium, and amine cations including, but not limited to ammonium, tetramethylanunonium, tetraethyl ammonium, methyl amine, dimethyl amine, trimethylamine, triethylamine, ethylamine, and the like (see, e.g., Berge S. M., et al. (1977) J. Pharm. Sci. 66, 1, which is incorporated herein by reference).

The term "pharmaceutically acceptable esters" refers to the relatively nontoxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. The term is further intended to include lower hydrocarbon groups capable of being solvated under physiological conditions, e.g., alkyl esters, methyl, ethyl and propyl esters.

As used herein, "pharmaceutically acceptable salts or prodrugs" are salts or prodrugs that are, within the scope of sound medical judgment, suitable for use in contact with the tissues of subject without undue toxicity, irritation, allergic response, and the like, commensurate with a reasonable benefit/risk ratio, and effective for their intended use.

The term "prodrug" refers to compounds that are rapidly transformed in vivo to yield the functionally active one or more peptides as disclosed herein or a mutant, variant, analog or derivative thereof. A thorough discussion is provided in T. Higachi and V. Stella, "Pro-drugs as Novel Delivery Systems," Vol. 14 of the A. C. S. Symposium Series, and in Bioreversible Carriers in: Drug Design, ed. Edward B. Roche, American Pharmaceutical Association and Pergamon Press, 1987, both of which are hereby incorporated by reference. As used herein, a prodrug is a compound that, upon in vivo administration, is metabolized or otherwise converted to the biologically, pharmaceutically or therapeutically active form of the compound. A prodrug of the one or more peptides as disclosed herein or a mutant, variant, analog or derivative thereof can be designed to alter the metabolic stability or the transport characteristics of one or more peptides as disclosed herein or a mutant, variant, analog or derivative thereof, to mask side effects or toxicity, to improve the flavor of a compound or to alter other characteristics or properties of a compound. By virtue of knowledge of pharmacodynamic processes and drug metabolism in vivo, once a pharmaceutically active form of the one or more peptides as disclosed herein or a mutant, variant, analog or derivative thereof, those of skill in the pharmaceutical art generally can design prodrugs of the compound (see, e.g., Nogrady (1985) Medicinal Chemistry A Biochemical Approach, Oxford University Press, N. Y., pages 388-392). Conventional procedures for the selection and preparation of suitable prodrugs are described, for example, in "Design of Prodrugs," ed. H. Bundgaard, Elsevier, 1985. Suitable examples of prodrugs include methyl, ethyl and glycerol esters of the corresponding acid.

Parenteral Compositions

The pharmaceutical composition may be administered parenterally by injection, infusion, or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation, or it may be presented as a dry powder to be reconstituted with water or another suitable vehicle before use. Apart from the active agent(s), the composition may include suitable parenterally acceptable carriers and/or excipients. The active agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing agents.

As indicated above, the pharmaceutical compositions according to the invention may be in a form suitable for sterile injection. To prepare such a composition, the suitable active agent(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, dextrose solution, and isotonic sodium chloride solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for intravenous, oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

Pharmaceutical compositions of this invention suitable for parenteral administration comprise one or more peptides as disclosed herein or a mutant, variant, analog or derivative thereof in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions comprising one or more peptides as disclosed herein or a mutant, variant, analog or derivative thereof include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug, such as one or more peptides as disclosed herein or a mutant, variant, analog or derivative thereof in liposomes or microemulsions which are compatible with body tissue.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of ordinary skill in the art.

Controlled Release Parenteral Compositions

Controlled release parenteral compositions may be in form of aqueous suspensions, microspheres, microcapsules, magnetic microspheres, oil solutions, oil suspensions, or emulsions. The composition may also be incorporated in biocompatible carriers, liposomes, nanoparticles, implants, or infusion devices.

Materials for use in the preparation of microspheres and/or microcapsules are, e.g., biodegradable/bioerodible polymers such as polygalactia poly-(isobutyl cyanoacrylate), poly(2-hydroxyethyl-L-glutamine), poly(lactic acid), polyglycolic acid, and mixtures thereof. Biocompatible carriers that may be used when formulating a controlled release parenteral formulation are carbohydrates (e.g., dextrans), proteins (e.g., albumin), lipoproteins, or antibodies. Materials for use in implants can be nonbiodegradable (e.g., polydimethyl siloxane) or biodegradable (e.g., poly(caprolactone), poly(lactic acid), poly(glycolic acid) or poly(ortho esters)) or combinations thereof.

Solid Dosage Forms for Oral Use

Formulations for oral use include tablets containing the active ingredient(s) in a mixture with non-toxic pharmaceutically acceptable excipients, and such formulations are known to the skilled artisan (e.g., U.S. Pat. Nos. 5,817,307; 5,824,300; 5,830,456; 5,846,526; 5,882,640; 5,910,304; 6,036,949; 6,036,949; and 6,372,218 hereby incorporated by reference). These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and anti-adhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the protein in a predetermined pattern (e.g., in order to achieve a controlled release formulation) or it may be adapted not to release the agent(s) until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material such as, e.g., glyceryl monostearate or glyceryl distearate, may be employed.

The solid tablet compositions may include a coating adapted to protect the composition from unwanted chemical changes, (e.g., chemical degradation prior to the release of the active substances). The coating may be applied on the solid dosage form in a similar manner as that described in Encyclopedia of Pharmaceutical Technology, supra.

The compositions of the invention may be mixed together in the tablet, or may be partitioned. In one example, a first agent is contained on the inside of the tablet, and a second agent is on the outside, such that a substantial portion of the second agent is released prior to the release of the first agent.

Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate, or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus, or spray drying equipment.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs.

In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration of one or more peptides as disclosed herein or a mutant, variant, analog or derivative thereof include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of the compounds of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel. In another aspect, biodegradable or absorbable polymers can provide extended, often localized, release of polypeptide agents. The potential benefits of an increased half-life or extended release for a therapeutic agent are clear. A potential benefit of localized release is the ability to achieve much higher localized dosages or concentrations, for greater lengths of time, relative to broader systemic administration, with the potential to also avoid possible undesirable side effects that may occur with systemic administration.

Bioabsorbable polymeric matrix suitable for delivery of the one or more peptides as disclosed herein or a mutant, variant, analog or derivative thereof can be selected from a variety of synthetic bioabsorbable polymers, which are described extensively in the literature. Such synthetic bioabsorbable, biocompatible polymers, which may release proteins over several weeks or months can include, for example, poly-α-hydroxy acids (e.g. polylactides, polyglycolides and their copolymers), polyanhydrides, polyorthoesters, segmented block copolymers of polyethylene glycol and polybutylene terephthalate (Polyactive™), tyrosine derivative polymers or poly(ester-amides). Suitable bioabsorbable polymers to be used in manufacturing of drug delivery materials and implants are discussed e.g. in U.S. Pat. Nos. 4,968,317, 5,618,563, among others, and in "Biomedical Polymers" edited by S. W. Shalaby, Carl Hanser Verlag, Munich, Vienna, New York, 1994 and in many references cited in the above publications. The particular bioabsorbable polymer that should be selected will depend upon the particular patient that is being treated.

Vectors of the Invention

Vectors comprising nucleic acids encoding the "SYN1753", "SYN3258", "SNY514", "SYN515", or "SYN531" polypeptides, or analogs, derivatives, or fragments thereof may be used to produce soluble polypeptides for use in the methods of the invention. The choice of vector and expression control sequences to which such nucleic acids are operably linked depends on the functional properties desired, e.g., protein expression, and the host cell to be transformed.

In a typical embodiment, a "SYN1753", "SYN3258", "SNY514", "SYN515", or "SYN531" polypeptide, or analog, derivative, or fragment thereof useful in the methods described herein is a recombinant protein produced by a cell (e.g., a CHO cell) that carries an exogenous nucleic acid encoding the protein. In other embodiments, the recombinant polypeptide is produced by a process commonly known as gene activation, wherein a cell that carries an exogenous nucleic acid that includes a promoter or enhancer is operably linked to an endogenous nucleic acid that encodes the polypeptide.

Routine techniques for making recombinant polypeptides (e.g., recombinant "SYN1753", "SYN3258", "SNY514", "SYN515", or "SYN531" polypeptides, or analogs, derivatives, or fragments thereof) may be used to construct expression vectors encoding the polypeptides of interest using appropriate transcriptional/translational control signals and the protein coding sequences. (See, for example, Sambrook et al., Molecular Cloning: A Laboratory Manual, 3d Ed. (Cold Spring Harbor Laboratory 2001)). These methods may include in vitro recombinant DNA and synthetic techniques and in vivo recombination, e.g., in vivo homologous recombination. Expression of a nucleic acid sequence encoding a polypeptide may be regulated by a second nucleic acid sequence that is operably linked to the polypeptide encoding sequence such that the polypeptide is expressed in a host transformed with the recombinant DNA molecule.

Expression control elements useful for regulating the expression of an operably linked coding sequence are known in the art. Examples include, but are not limited to, inducible promoters, constitutive promoters, secretion signals, and other regulatory elements. When an inducible promoter is used, it can be controlled, e.g., by a change in nutrient status, or a change in temperature, in the host cell medium.

Expression vectors capable of being replicated in a bacterial or eukaryotic host comprising a nucleic acid encoding a polypeptide are used to transfect a host and thereby direct expression of such nucleic acid to produce the polypeptide, which may then be isolated. The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Routine techniques for transfecting cells with exogenous DNA sequences may be used in the present invention. Transfection methods may include chemical means, e.g.; calcium phosphate, DEAE-dextran, or liposome; or physical means, e.g., microinjection or electroporation. The transfected cells are grown up by routine techniques. For examples, see Kuchler et al. (1977) Biochemical Methods in Cell Culture and Virology. The expression products are isolated from the cell medium in those systems where the protein is secreted from the host cell, or from the cell suspension after disruption of the host cell system by, e.g., routine mechanical, chemical, or enzymatic means. These methods may also be carried out using cells that have been genetically modified by other procedures, including gene targeting and gene activation (see Treco et al. WO 95/31560, herein incorporated by reference; see also Selden et al. WO 93/09222).

The vector can include a prokaryotic replicon, i.e., a DNA sequence having the ability to direct autonomous replication and maintenance of the recombinant DNA molecule extrachromosomally in a bacterial host cell. Such replicons are well known in the art. In addition, vectors that include a prokaryotic replicon may also include a gene whose expression confers a detectable marker such as a drug resistance. Examples of bacterial drug-resistance genes are those that confer resistance to ampicillin or tetracycline.

Vectors that include a prokaryotic replicon can also include a prokaryotic or bacteriophage promoter for directing expression of the coding gene sequences in a bacterial host cell. Promoter sequences compatible with bacterial hosts are typically provided in plasmid vectors containing convenient restriction sites for insertion of a DNA segment to be expressed. Examples of such plasmid vectors are pUC8, pUC9, pBR322 and pBR329 (BioRad), pPL and pKK223 (Pharmacia). Any suitable prokaryotic host can be used to express a recombinant DNA molecule encoding a protein used in the methods of the invention.

For the purposes of this invention, numerous expression vector systems may be employed. For example, one class of vector utilizes DNA elements which are derived from animal viruses such as bovine papilloma virus, polyoma virus, adenovirus, adeno-associated virus, herpes simplex virus-1, vaccinia virus, baculovirus, retroviruses (RSV, MMTV or MOMLV) or SV40 virus. Examples of such vectors can be found in PCT publications WO 2006/060089 and WO2002/056918 which are incorporated herein in their entireties. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. The neomycin phosphotransferase (neo) gene is an example of a selectable marker gene (Southern et al., J. Mol. Anal. Genet. 1:327-341 (1982)). Additional elements may also be needed for optimal synthesis of mRNA. These elements may include signal sequences, splice signals, as well as transcriptional promoters, enhancers, and termination signals.

In one embodiment, a proprietary expression vector of Biogen IDEC, Inc., referred to as NEOSPLA (U.S. Pat. No. 6,159,730) may be used. This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. This vector has been found to result in very high level expression upon transfection in CHO cells, followed by selection in G418 containing medium and methotrexate amplification. Of course, any expression vector which is capable of eliciting expression in eukaryotic cells may be used in the present invention. Examples of suitable vectors include, but are not limited to plasmids pcDNA3, pHCMV/Zeo, pCR3.1, pEF1/His, pIND/ GS, pRc/HCMV2, pSV40/Zeo2, pTRACER-HCMV, pUB6N5-His, pVAX$_1$, and pZeoSV2 (available from Invitrogen, San Diego, Calif.), and plasmid pCI (available from Promega, Madison, Wis.). Additional eukaryotic cell expression vectors are known in the art and are commercially available. Typically, such vectors contain convenient restriction sites for insertion of the desired DNA segment. Exemplary vectors include pSVL and pKSV-10 (Pharmacia), pBPV-1, pm12d (International Biotechnologies), pTDT1 (ATCC 31255), retroviral expression vector pMIG and pLL3.7, adenovirus shuttle vector pDC315, and AAV vectors. Other exemplary vector systems are disclosed e.g., in U.S. Pat. No. 6,413,777.

The recombinant expression vectors may carry sequences that regulate replication of the vector in host cells (e.g., origins of replication) and selectable marker genes. It will be appreciated by those skilled in the art that the design of the expression vector, including the selection of regulatory sequences may depend on such factors as the choice of the host cell to be transformed, the level of expression of protein desired, etc. Frequently used regulatory sequences for mammalian host cell expression include viral elements that direct high levels of protein expression in mammalian cells, such as promoters and enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdmlP)), polyoma and strong mammalian promoters such as native immunoglobulin and actin promoters. For further description of viral regulatory elements, and sequences thereof, see e.g., Stinski, U.S. Pat. No. 5,168,062; Bell, U.S. Pat. No. 4,510,245; and Schaffner, U.S. Pat. No. 4,968,615.

The selectable marker gene facilitates selection of host cells into which the vector has been introduced (see, e.g., Axel, U.S. Pat. Nos. 4,399,216; 4,634,665 and 5,179,017). For example, typically the selectable marker gene confers resistance to a drug, such as G418, hygromycin or methotrexate, on a host cell into which the vector has been introduced. Frequently used selectable marker genes include the dihydrofolate reductase (DHFR) gene (for use in dhfr-host cells with methotrexate selection/amplification) and the neo gene (for G418 selection).

Vectors comprising polynucleotides encoding "SYN1753", "SYN3258", "SNY514", "SYN515", or "SYN531" polypeptides, or analogs, derivatives, or fragments thereof can be used for transformation of a suitable host cell. Transformation can be by any suitable method. Methods for introduction of exogenous DNA into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors.

Transformation of host cells can be accomplished by conventional methods suited to the vector and host cell employed. For transformation of prokaryotic host cells, electroporation and salt treatment methods can be employed (Cohen et al., Proc. Natl. Acad. Sci. USA 69:2110-14 (1972)). For transformation of vertebrate cells, electroporation, cationic lipid or salt treatment methods can be employed. See, e.g., Graham et al., Virology 52:456-467 (1973); Wigler et al., Proc. Natl. Acad. Sci. USA 76:1373-76 (1979).

The host cell line used for protein expression is most preferably of mammalian origin; those skilled in the art are credited with ability to preferentially determine particular host cell lines which are best suited for the desired gene product to be expressed therein. Exemplary host cell lines include, but are not limited to NSO, SP2 cells, baby hamster kidney (BHK) cells, monkey kidney cells (COS), human hepatocellular carcinoma cells (e.g., Hep G2), A549 cells DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/0 (mouse myeloma), P3x63-Ag3.653 (mouse myeloma), BFA-1c1BPT (bovine endothelial cells), RAH (human lymphocyte) and 293 (human kidney). Host cell lines are typically available from commercial services, the American Tissue Culture Collection or from published literature.

Expression of polypeptides from production cell lines can be enhanced using known techniques. For example, the glutamine synthetase (GS) system is commonly used for enhancing expression under certain conditions. See, e.g., European Patent Nos. 0 216 846, 0 256 055, and 0 323 997 and European Patent Application No. 89303964.4.

In some embodiments, the invention provides recombinant DNA molecules (rDNA) that contain a coding sequence. As used herein, a rDNA molecule is a DNA molecule that has been subjected to molecular manipulation. Methods for generating rDNA molecules are well known in the art, for example, see Sambrook et al., Molecular Cloning—A Laboratory Manual, Cold Spring Harbor Laboratory Press (1989). In some rDNA molecules, a coding DNA sequence is operably linked to expression control sequences and vector sequences. A vector of the present invention may be at least capable of directing the replication or insertion into the host chromosome, and preferably also expression, of the structural gene included in the rDNA molecule.

Expression vectors compatible with eukaryotic cells, preferably those compatible with vertebrate cells, can also be used to form a rDNA molecules that contains a coding sequence. Eukaryotic cell expression vectors are well known in the art and are available from several commercial sources. Typically, such vectors are provided containing convenient restriction sites for insertion of the desired DNA segment. Examples of such vectors are pSVL and pKSV-10 (Pharmacia), pBPV-1, pML2d (International Biotechnologies), pTDT1 (ATCC® 31255) and other eukaryotic expression vectors.

Eukaryotic cell expression vectors used to construct the rDNA molecules of the present invention may further include a selectable marker that is effective in an eukaryotic cell, preferably a drug resistance selection marker. A preferred drug resistance marker is the gene whose expression results in neomycin resistance, i.e., the neomycin phosphotransferase (neo) gene. (Southern et al., J. Mol. Anal. Genet. 1:327-341 (1982)). Alternatively, the selectable marker can be present on a separate plasmid, the two vectors introduced by co-transfection of the host cell, and transfectants selected by culturing in the appropriate drug for the selectable marker.

Other embodiments of the invention use a lentiviral vector for expression of the polynucleotides of the invention. Lentiviruses can infect noncycling and postmitotic cells, and also provide the advantage of not being silenced during development allowing generation of transgenic animals through infection of embryonic stem cells. Milhavet et al., Pharmacological Rev. 55:629-648 (2003). Other polynucleotide expressing viral vectors can be constructed based on, but not limited to, adeno-associated virus, retrovirus, adenovirus, or alphavirus.

Transcription of the polynucleotides of the invention can be driven from a promoter for eukaryotic RNA polymerase I (pol I), RNA polymerase II (pol II), or RNA polymerase III (pol III). Transcripts from pol II or pol III promoters are expressed at high levels in all cells; the levels of a given pol II promoter in a given cell type depends on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, Proc. Natl. Acad. Sci. USA 87:6743-7 (1990); Gao and Huang, Nucleic Acids Res. 21:2867-72 (1993); Lieber et al., Methods Enzymol. 217:47-66 (1993); Zhou et al., Mol. Cell. Biol. 10:4529-37 (1990)). Several investigators have demonstrated that polynucleotides expressed from such promoters can function in mammalian cells (e.g. Kashani-Sabet et al., Antisense Res. Dev. 2:3-15 (1992); Ojwang et al., Proc. Natl. Acad. Sci. USA 89:10802-6 (1992); Chen et al., Nucleic Acids Res. 20:4581-9 (1992); Yu et al., Proc. Natl. Acad. Sci. USA 90:6340-4 (1993); L'Huillier et al., EMBO J. 11:4411-8 (1992); Lisziewicz et al., Proc. Natl. Acad. Sci. U.S.A 90:8000-4 (1993); Thompson et al., Nucleic Acids Res. 23:2259 (1995); Sullenger & Cech, Science 262:1566 (1993)).

Host Cells and Methods of Recombinantly Producing Protein of the Invention

Nucleic acid molecules encoding "SYN1753", "SYN3258", "SNY514", "SYN515", or "SYN531" polypeptides, or analogs, derivatives, or fragments thereof of this invention and vectors comprising these nucleic acid molecules can be used for transformation of a suitable host cell. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors.

Transformation of appropriate cell hosts with a rDNA molecule of the present invention is accomplished by well known methods that typically depend on the type of vector used and host system employed. With regard to transformation of prokaryotic host cells, electroporation and salt treatment methods can be employed (see, for example, Sambrook et al., Molecular Cloning—A Laboratory Manual, Cold Spring Harbor Laboratory Press (1989); Cohen et al., Proc. Natl. Acad. Sci. USA 69:2110-2114 (1972)). With regard to transformation of vertebrate cells with vectors containing rDNA, electroporation, cationic lipid or salt treatment methods can be employed (see, for example, Graham et al., Virology. 52:456-467 (1973); Wigler et al., Proc. Natl. Acad. Sci. USA 76:1373-1376 (1979)).

Successfully transformed cells, i.e., cells that contain a rDNA molecule of the present invention, can be identified by well-known techniques including the selection for a selectable marker. For example, cells resulting from the introduction of an rDNA of the present invention can be cloned to produce single colonies. Cells from those colonies can be harvested, lysed and their DNA content examined for the presence of the rDNA using a method such as that described by Southern, J. Mol. Biol. 98:503-517 (1975) or the proteins produced from the cell may be assayed by an immunological method.

Host cells for expression of a polypeptide of the invention for use in a method of the invention may be prokaryotic or eukaryotic. Mammalian cell lines available as hosts for expression are well known in the art and include many immortalized cell lines available from the American Type Culture Collection (ATCC®). These include, inter alia, Chinese hamster ovary (CHO) cells, NSO, SP2 cells, HeLa cells, baby hamster kidney (MK) cells, monkey kidney cells (COS), human hepatocellular carcinoma cells (e.g., Hep G2), A549 cells, and a number of other cell lines. Cell lines of particular preference are selected through determining which cell lines have high expression levels. Other useful eukaryotic host cells include plant cells. Other cell lines that may be used are insect cell lines, such as Sf9 cells. Exemplary prokaryotic host cells are E. coli and Streptomyces.

When recombinant expression vectors encoding the "SYN1753", "SYN3258", "SNY514", "SYN515", or "SYN531" polypeptides, or analogs, derivatives, or fragments thereof of the invention are introduced into mammalian host cells, they are produced by culturing the host cells for a period of time sufficient to allow for expression of the polypeptide in the host cells or, more preferably, secretion of the "SYN1753", "SYN3258", "SNY514", "SYN515", or "SYN531" polypeptides, or analogs, derivatives, or fragments thereof of the invention into the culture medium in which the host cells are grown. "SYN1753", "SYN3258", "SNY514", "SYN515", or "SYN531" polypeptides, or analogs, derivatives, or fragments thereof of the invention can be recovered from the culture medium using standard protein purification methods.

Further, expression of "SYN1753", "SYN3258", "SNY514", "SYN515", or "SYN531" polypeptides, or analogs, derivatives, or fragments thereof of the invention of the invention (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4.

A polypeptide produced by a cultured cell as described herein can be recovered from the culture medium as a secreted polypeptide, or, if it is not secreted by the cells, it can be recovered from host cell lysates. As a first step in isolating the polypeptide, the culture medium or lysate is generally centrifuged to remove particulate cell debris. The polypeptide thereafter is isolated, and preferably purified, from contaminating soluble proteins and other cellular components, with the following procedures being exemplary of suitable purification procedures: fractionation on immunoaffinity or ion-exchange columns; ethanol precipitation; reverse phase HPLC; chromatography on silica or on a cation-exchange resin such as DEAE; chromatofocusing; SDS PAGE; ammonium sulfate precipitation; and gel filtration, e.g., with Sephadex™ columns (Amersham Biosciences). Protease inhibitors may be used to inhibit proteolytic degradation during purification. One skilled in the art will appreciate that purification methods suitable for the polypeptide of interest may require modification to account for changes in the character of the polypeptide upon expression in recombinant cell culture.

The purification of polypeptides may require the use of, e.g., affinity chromatography, conventional ion exchange chromatography, sizing chromatography, hydrophobic interaction chromatography, reverse phase chromatography, gel filtration or other conventional protein purification techniques. See, e.g., Deutscher, ed. (1990) "Guide to Protein Purification" in Methods in Enzymology, Vol. 182.

Methods of Treatment and Uses for the Peptides

Various embodiments provide for a method of blocking the interaction of neonatal Fc receptor (FCRN) and albumin comprising contacting a system comprising neonatal Fc receptor (FCRN) and albumin with the "SYN1753" or "SYN3258" polypeptides, or analogs, derivatives, or fragments thereof of the invention as described herein. In various embodiments, the invention provides use of the peptides for treatment of conditions where blocking the interaction between neonatal Fc receptor (FCRN) and albumin is needed.

Various embodiments of the present invention provide for a method of blocking the interaction between neonatal Fc receptor (FCRN) and albumin in a subject in need thereof, comprising administering the "SYN1753" or "SYN3258" polypeptides, or analogs, derivatives, or fragments thereof of the invention as described herein to the subject. For example, an isolated polypeptide having Formula I is administered to the subject. In some aspects of all the embodiments of the invention, the subject is first diagnosed as having a condition wherein blocking the interaction between neonatal Fc receptor (FCRN) and albumin is useful as a treatment.

In various embodiments the "SYN1753" or "SYN3258" polypeptides, or analogs, derivatives, or fragments thereof of the invention as described herein that are administered to the subjects are not antigen-binding portions of antibodies.

In various embodiments blocking the interaction between neonatal Fc receptor (FcRn) and albumin decreases albumin level in the subject.

In various embodiments, blocking the interaction between neonatal Fc receptor (FcRn) and albumin treats a disease or condition caused by increased amount of albumin.

In various embodiments, the disease or condition is acute toxigenic exposure or sub-acute toxigenic exposure to a drug.

In various embodiments, the disease or condition is selected from the group consisting of diabetes, kernicterus, metabolic disorders such as metabolic syndrome, diabetes mellitus or hyperthyroidism tuberculosis, hepatitis, HIV, chronic inflammation, or infection. In some aspects of all the embodiments of the invention, the subject having disease or condition is selected from the group consisting of diabetes, kernicterus, metabolic disorders such as metabolic syndrome, diabetes mellitus or hyperthyroidism tuberculosis, hepatitis, HIV, chronic inflammation, or infection is first subjected to measurement of the albumin amount, and if the albumin amount in the subject is increased, then administering one or more peptides of the invention to the subject.

Tumors and inflamed tissues show increased accumulation of albumin as a result of leaky capillaries and defective lymphatic drainage. Consequently, albumin-based therapeutics or diagnostics accumulate at the site of tumour or inflammation. Because of tissue toxicity of the fused molecules, fine-tuning of albumin half-life may be an attractive approach to improve tumour targeting and imaging, as previously shown for IgGs with attenuated affinity for FcRn. The peptides described herein may serve as therapeutic or diagnostic for tumors and inflamed tissues as well. In some aspects of all the embodiments of the invention, the subject with tumor or inflammation is first subjected to analysis of albumin levels, and if the subject is determined to have increased albumin accumulation, and if the subject has increased albumin accumulation, then administering one or more of the peptides of the invention to treat the tumors or inflammation in the subject.

Various embodiments of the present invention provide for a use of the isolated "SYN1753" or "SYN3258" polypeptides, or analogs, derivatives, or fragments thereof of the invention as described herein the composition comprising "SYN1753" or "SYN3258" polypeptides, or analogs, derivatives, or fragments thereof of the invention as described herein for treating a disease or condition caused by increased amount of albumin, such as acute toxigenic exposure or sub-acute toxigenic exposure to a drug or toxin, diabetes, kernicterus, metabolic disorders such as metabolic syndrome, diabetes mellitus or hyperthyroidism, tuberculosis, hepatitis, HIV, chronic inflammation, or infection.

Drug or toxin used with respect to acute toxigenic exposure or sub-acute toxigenic exposure to a drug or toxin refers to a compound, drug, or molecule that binds albumin. While it may be desirable under some circumstances to decrease the concentration of an albumin-binding toxin in a subject, the term is not limited to a compound, drug, or molecule that is labeled as a "toxin." Examples of these drugs or toxins includes but are not limited to, copper, hematin, long-chain fatty acid, zinc, bilirubin, thyroxine, eicosanoids, tryptophan, vitamin D3, bile acids, calcium, magnesium, chloride, indomethacin, bromphenol blue, salicylate, warfarin, phenylbutazone, digoxin, furosemide, phenytoin, chlorpropamide, benzylpenicillin, Evans blue, diazepam, ibuprofen, naproxen, clofibrate, chlorpromazine, imipramine, quinidine, Ricin, and acetaminophen, as described in U.S. Pat. No. 8,232,067, which is incorporated by reference in its entirety as though fully set forth.

As used herein, the terms "treat" or "treatment" or "treating" refers to therapeutic treatment measures, wherein the object is to prevent or slow the development of the disease, such as reducing at least one effect or symptom of a condition, disease or disorder wherein albumin levels are desired to be lowered as when albumin levels are elevated or there are increased levels of albumin that possesses pathogenic properties. The latter includes for examined the presence of elevated levels of advanced glycation end-product (AGE)-modified (glycated) through ingestion of toxins or hyperglycemia associated with diabetes mellitus. tuberculosis, hepatitis, HIV, chronic inflammation, or infection.

Treatment is generally "effective" if one or more symptoms are improved or clinical markers or levels are within normal values or closer to the normal reference values than abnormal values reflecting high albumin levels, depending on the condition, as that term is defined herein. Alternatively, treatment is "effective" if the progression of a disease is slowed down, exhibition of a symptom or a marker for a disease is reduced. That is, "treatment" includes the improvement of symptoms or markers, slowing of progress or slowing of worsening of at least one symptom that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state. "Treatment" can also mean prolonging survival as compared to expected survival if not receiving treatment. Those in need of treatment include patients with one or more symptom of high albumin levels. The term treatment does not encompass "cure." In some aspects of all the embodiments of the invention, the treatment is effective if the albumin levels after the treatment are reduced compared to before the treatment. Thus, in some aspects of all the embodiments of the invention, the methods include a step of determining the albumin level in the subject before administering the one or more peptides, and after administering the one or more peptides, so that a dosage can be adjusted to an amount that causes reduction in or normalization of the albumin levels in the subject.

The term "effective amount" as used herein refers to the amount of a pharmaceutical composition comprising one or more peptides as disclosed herein or a mutant, variant, analog or derivative thereof, to decrease at least one or more symptom of the disease or disorder, and relates to a sufficient amount of pharmacological composition to provide the desired effect. The phrase "therapeutically effective amount" as used herein means a sufficient amount of the composition to treat a disorder, at a reasonable benefit/risk ratio applicable to any medical treatment. The term "therapeutically effective amount" therefore refers to an amount of the composition as disclosed herein that is sufficient to effect a therapeutically or prophylactically significant reduction in a symptom or clinical marker associated with high albumin levels when administered to a typical subject. Typically reduction of more than 20% of a disease marker, such as high albumin levels, is indicative of effective treatment. In some instances, reduction of more than 50% or more than 75% from the amount of albumin levels in the individual prior to administering the peptides of the invention is indicative of effective treatment.

A therapeutically or prophylactically significant reduction in a symptom is, e.g. at least about 10%, at least about 20%, at least about 30%, at least about 40%, at least about 50%, at least about 60%, at least about 70%, at least about 80%, at least about 90% improvement in a measured parameter as compared to a control or non-treated subject or the state of the subject prior to administering the peptide. Measured or measurable parameters include clinically detectable markers of disease, for example, elevated or depressed levels of a biological marker, such as glycated albumin levels, as well as parameters related to a clinically accepted scale of symptoms or markers for high albumin levels. It will be understood, however, that the total daily usage of the compositions and formulations as disclosed herein will be decided by the attending physician within the scope of sound medical judgment. The exact amount required will vary depending on factors such as the type of disease being treated, gender, age, and weight of the subject.

With reference to the treatment of a subject with high albumin levels, the term "therapeutically effective amount" refers to the amount that is safe and sufficient to delay the development of one or more symptom and results in decrease in the amount of albumin prior to administering the peptide. The amount can thus improve or cause a decrease in albumin levels. The effective amount for the treatment of a disease depends on the type of disease, the species being treated, the age and general condition of the subject, the mode of administration and so forth. Thus, it is not possible to specify the exact "effective amount." However, for any given case, an appropriate "effective amount" can be determined by one of ordinary skill in the art using only routine experimentation. The efficacy of treatment can be judged by an ordinarily skilled practitioner.

As used herein, the terms "administering," and "introducing" are used interchangeably herein and refer to the placement of the therapeutic agents such as one or more peptides as disclosed herein or a mutant, variant, analog or derivative thereof into a subject by a method or route which results in delivering of such agent(s) at a desired site. The compounds can be administered by any appropriate route which results in an effective treatment in the subject.

The one or more peptides as disclosed herein or a mutant, variant, analog or derivative thereof may be administered by any route known in the art or described herein, for example, oral, parenteral (e.g., intravenously or intramuscularly), intraperitoneal, rectal, cutaneous, nasal, vaginal, inhalant, skin (patch), or ocular. The one or more peptides as disclosed herein or a mutant, variant, analog or derivative thereof may be administered in any dose or dosing regimen. One can also use pumps, like the ones used for insulin administration. For example, various approaches are possible to increase the stability of orally administered peptides against proteolysis, including formulation in liposomes, coating with polymers and genetic engineering of resistant forms. Various approaches are possible to increase the stability of orally administered peptides against proteolysis, including formulation in liposomes, coating with polymers and genetic engineering of resistant forms (see, e.g., Reilly et al. Clin Pharmacokinet. 1997 April; 32(4):313-23).

Dosage

With respect to the therapeutic methods of the invention, it is not intended that the administration of the one or more peptides as disclosed herein or a mutant, variant, analog or derivative thereof and be limited to a particular mode of administration, dosage, or frequency of dosing; the present invention contemplates all modes of administration, including intramuscular, intravenous, intraperitoneal, intravesicular, intraarticular, intralesional, subcutaneous, or any other route sufficient to provide a dose adequate to treat the disease or disorder. The therapeutic may be administered to the patient in a single dose or in multiple doses. When multiple doses are administered, the doses may be separated from one another by, for example, one hour, three hours, six hours, eight hours, one day, two days, one week, two weeks, or one month. For example, the therapeutic may be administered for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the compositions. For example, the dosage of the therapeutic can be increased if the lower dose does not provide sufficient therapeutic activity.

While the attending physician ultimately will decide the appropriate amount and dosage regimen, therapeutically effective amounts of the one or more peptides as disclosed herein or a mutant, variant, analog or derivative thereof may be provided at a dose of 0.0001, 0.01, 0.01 0.1, 1, 5, 10, 25, 50, 100, 500, or 1,000 mg/kg or µg/kg. Effective doses may be extrapolated from dose-response curves derived from in vitro or animal model test bioassays or systems.

Dosages for a particular patient or subject can be determined by one of ordinary skill in the art using conventional considerations, (e.g. by means of an appropriate, conventional pharmacological protocol). A physician may, for example, prescribe a relatively low dose at first, subsequently increasing the dose until an appropriate response is obtained. The dose administered to a patient is sufficient to effect a beneficial therapeutic response in the patient over time, or, e.g., to reduce symptoms, or other appropriate activity, depending on the application. The dose is determined by the efficacy of the particular formulation, and the activity, stability or serum half-life of the one or more peptides as disclosed herein or a mutant, variant, analog or derivative thereof and the condition of the patient, as well as the body weight or surface area of the patient to be treated. The size of the dose is also determined by the existence, nature, and extent of any adverse side-effects that accompany the administration of a particular vector, formulation, or the like in a particular subject. Therapeutic compositions comprising one or more peptides as disclosed herein or a mutant, variant, analog or derivative thereof are optionally tested in one or more appropriate in vitro and/or in vivo animal models of disease, to confirm efficacy, tissue metabolism, and to estimate dosages, according to methods well known in the art. In particular, dosages can be initially determined by activity, stability or other suitable measures of treatment vs. non-treatment (e.g., comparison of treated vs. untreated cells or animal models), in a relevant assay. Formulations are administered at a rate determined by the LD50 of the relevant formulation, and/or observation of any side-effects of one or more peptides as disclosed herein or a mutant, variant, analog or derivative thereof. Administration can be accomplished via single or divided doses.

In determining the effective amount of one or more peptides as disclosed herein or a mutant, variant, analog or derivative thereof to be administered in the treatment or prophylaxis of disease the physician evaluates circulating plasma levels, formulation toxicities, and progression of the disease.

The efficacy and toxicity of the compound can be determined by standard pharmaceutical procedures in cell cultures or experimental animals, e.g., ED50 (the dose is effective in 50% of the population) and LD50 (the dose is lethal to 50% of the population). The dose ratio of toxic to therapeutic effects is the therapeutic index, and it can be expressed as the ratio, LD50/ED50. Pharmaceutical compositions which exhibit large therapeutic indices are preferred.

These compounds may be administered to humans and other animals for therapy by any suitable route of administration that works for small peptides, including orally, nasally, as by, for example, a spray, rectally, intravaginally, parenterally, intracisternally and topically, as by powders, ointments or drops, including buccally and sublingually.

Actual dosage levels of the active ingredients in the pharmaceutical compositions of this invention may be varied so as to obtain an amount of the active ingredient which is effective to achieve the desired therapeutic response for a particular subject, composition, and mode of administration, without being toxic to the subject.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

Methods of Tracking FcRn without Inhibiting IgG or Albumin Binding or Function

Various embodiments provide for a method of tracking FcRn without inhibiting IgG or albumin binding or function comprising contacting a system comprising neonatal Fc receptor (FCRN) with the "SYN514", "SYN515", or "SYN531" polypeptides, or analogs, derivatives, or fragments thereof of the invention as described herein, wherein "SYN514", "SYN515", or "SYN531" polypeptides, or analogs, derivatives, or fragments thereof further comprises a label to produce a signal; and tracking FCRN by detecting the signal. In various embodiments, the tracking is performed in vivo. Examples of labels are described above.

Non-Human Machines/Computer Implementation Systems and Methods

In certain embodiments, the methods of the invention implement a computer program for example, to compare the binding activity, to identify a loss or gain of function mutation. For example, a computer program can be used to perform the algorithms described herein. The computer programs can be executed using a non-human machine and caused to display the results in a format understandable to a clinician without the involvement of the clinician in the analysis process.

Numerous types of computer systems can be used to implement the analytic methods of this invention according to knowledge possessed by a skilled artisan in the bioinformatics and/or computer arts.

Several software components can be loaded into memory during operation of such a computer system. The software components can comprise both software components that are standard in the art and components that are special to the present invention. The methods of the invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.). In certain embodiments, the computer comprises a database for storage of binding affinity profiles. Such stored profiles can be accessed and used to compare binding affinities or to identify a loss or gain of function.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

Once a laboratory technician or laboratory professional or group of laboratory technicians or laboratory professionals determines whether a mutant has a loss or gain of function, the same or a different laboratory technician or laboratory professional (or group) can analyze a plurality of test to compare binding affinities or to identify a loss or gain of function. The analysis may also be done completely using non-human machines, such as computers executing the analysis and comparison algorithms, e.g., needed to compare the albumin levels of the subject and the reduction thereof with the peptides of the invention whether in an in vitro system, or in vivo system.

In various embodiments, provided herein is a computer readable storage medium comprising: a storing data module containing data from a sample comprising mutant protein comprising SEQ ID NO:8, wherein one or more amino acids selected from Glu565, Asn111 or Asn109 have been mutated to any other amino acid or an amino acid analog; a detection module to detect binding affinity of the human FcRn with the mutant protein; a comparison module that compares the data stored on the storing data module with a reference data and/or control data, and to provide a comparison content, and an output module displaying the comparison content for the user, wherein a loss of function mutation is displayed when the binding activity of the mutant protein is decreased or abolished compared to the wild-type protein and a gain of function mutation is displayed when the binding activity of the mutant protein is increased compared to the wild type protein.

In various embodiments, the control data comprises data from wild-type binding affinities.

Embodiments of the invention can be described through functional modules, which are defined by computer executable instructions recorded on computer readable media and which cause a computer to perform method steps when executed. The modules are segregated by function, for the sake of clarity. However, it should be understood that the modules/systems need not correspond to discreet blocks of code and the described functions can be carried out by the execution of various code portions stored on various media and executed at various times. Furthermore, it should be appreciated that the modules may perform other functions, thus the modules are not limited to having any particular functions or set of functions.

The computer readable storage media can be any available tangible media that can be accessed by a computer. Computer readable storage media includes volatile and nonvolatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can accessed by a computer including and any suitable combination of the foregoing.

Computer-readable data embodied on one or more computer-readable media may define instructions, for example, as part of one or more programs that, as a result of being executed by a computer, instruct the computer to perform one or more of the functions described herein, and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable media on which such instructions are embodied may reside on one or more of the components of either of a system, or a computer readable storage medium described herein, may be distributed across one or more of such components.

The computer-readable media may be transportable such that the instructions stored thereon can be loaded onto any computer resource to implement the aspects of the present invention discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a computer to implement aspects of the present invention. The computer executable instructions may be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

The functional modules of certain embodiments of the invention; include for example, a measuring module, a storage module, a comparison module, and an output module. The functional modules can be executed on one, or multiple, computers, or by using one, or multiple, computer networks. The measuring module has computer executable instructions to provide e.g., expression information in computer readable form.

The measuring module can comprise any system for detecting the bindin affinities.

The information determined in the determination system can be read by the storage module. As used herein the "storage module" is intended to include any suitable computing or processing apparatus or other device configured or adapted for storing data or information. Examples of electronic apparatus suitable for use with the present invention include stand-alone computing apparatus, data telecommunications networks, including local area networks (LAN), wide area networks (WAN), Internet, Intranet, and Extranet, and local and distributed computer processing systems. Storage modules also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage module is adapted or configured for having recorded thereon expression level or protein level information. Such information may be provided in digital form that can be transmitted and read electronically, e.g., via the Internet, on diskette, via USB (universal serial bus) or via any other suitable mode of communication.

As used herein, "stored" refers to a process for encoding information on the storage module. Those skilled in the art can readily adopt any of the presently known methods for recording information on known media to generate manufactures comprising expression level information.

In one embodiment the reference data stored in the storage module to be read by the comparison module is e.g., wild-type binding data.

The "comparison module" can use a variety of available software programs and formats for the comparison operative to compare binding data determined in the measuring module to reference samples and/or stored reference data. In one embodiment, the comparison module is configured to use pattern recognition techniques to compare information from one or more entries to one or more reference data patterns. The comparison module may be configured using existing commercially-available or freely-available software for comparing patterns, and may be optimized for particular data comparisons that are conducted. The comparison module provides computer readable information related; for example, binding affinities and/or loss or gain of function The comparison module, or any other module of the invention, may include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets. An advantage of such Intranets is that they allow easy communication with public domain databases residing on the World Wide Web (e.g., the GenBank or Swiss Pro World Wide Web site). Thus, in a particular preferred embodiment of the present invention, users can directly access data (via Hypertext links for example) residing on Internet databases using a HTML interface provided by Web browsers and Web servers.

The comparison module provides a computer readable comparison result that can be processed in computer readable form by predefined criteria, or criteria defined by a user, to provide a content-based in part on the comparison result that may be stored and output as requested by a user using an output module.

The content based on the comparison result, may be a binding value compared to a reference showing a loss or gain of function.

In various embodiments of the invention, the content based on the comparison result is displayed on a computer monitor. In various embodiments of the invention, the content based on the comparison result is displayed through printable media. The display module can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In one embodiment, a World Wide Web browser is used for providing a user interface for display of the content based on the comparison result. It should be understood that other modules of the invention can be adapted to have a web browser interface. Through the Web browser, a user may construct requests for retrieving data from the comparison module. Thus, the user will typically point and click to user interface elements such as buttons, pull down menus, scroll bars and the like conventionally employed in graphical user interfaces.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* $3^{rd}$ ed., J. Wiley & Sons (New York, N.Y. 2001); March, *Advanced Organic Chemistry Reactions, Mechanisms and Structure* $5^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application. For references on how to prepare antibodies, see D. Lane, *Antibodies: A Laboratory Manual* (Cold Spring Harbor Press, Cold Spring Harbor N.Y., 1988); Kohler and Milstein, (1976) Eur. J. Immunol. 6: 511; Queen et al. U.S. Pat. No. 5,585,089; and Riechmann et al., Nature 332: 323 (1988).

One skilled in the art will recognize many methods and materials similar or equivalent to those described herein, which could be used in the practice of the present invention. Indeed, the present invention is in no way limited to the methods and materials described.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Figure 1A:
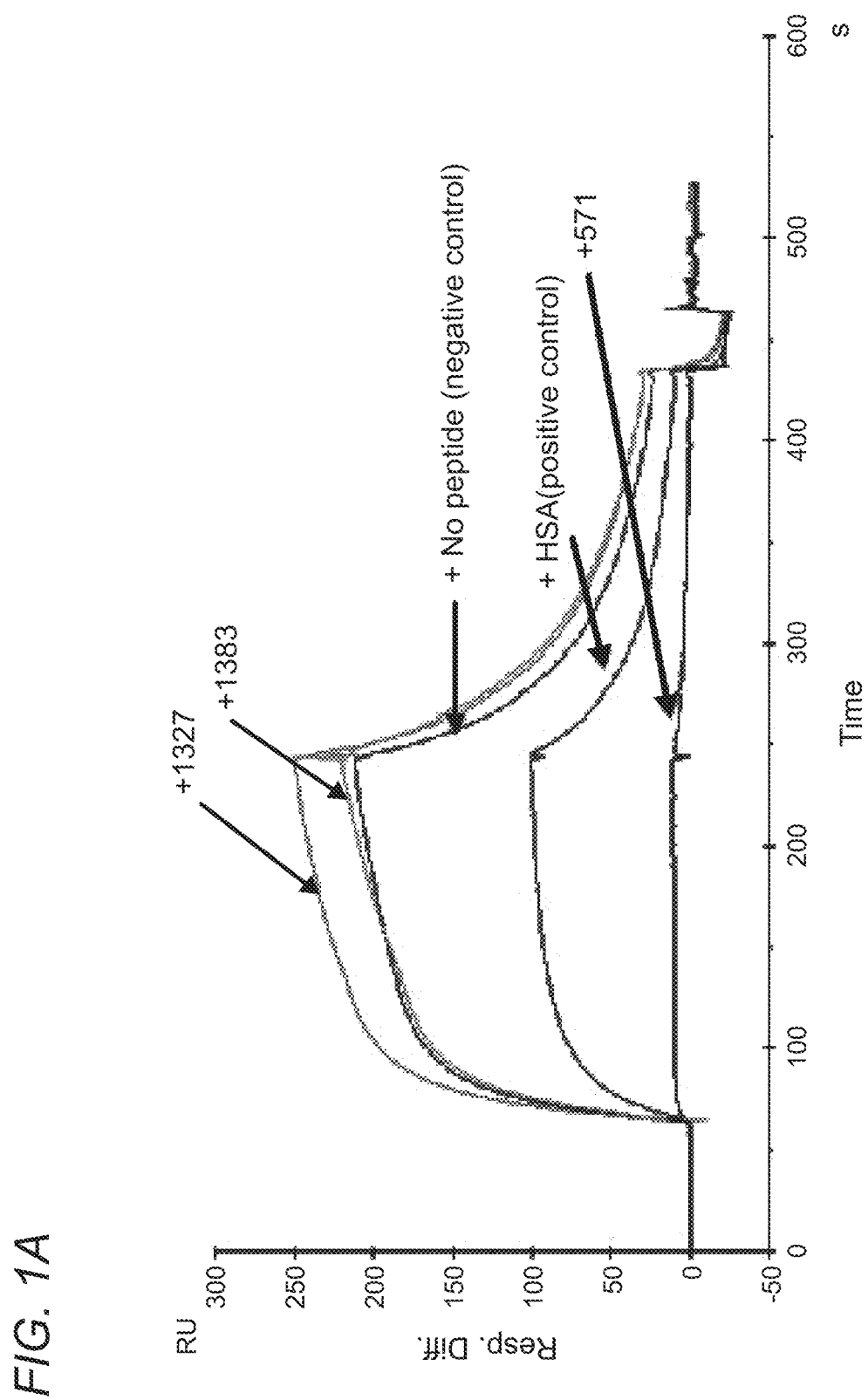
FIGS. 1A-1B depict SPR Data: SYN571 Peptide Blocks shFcRn binding to Immobilized Albumin. 100 uL samples containing 5 uM FcRn (5 uL 1 mg/mL stock) were prepared that contained no additive, HSA at 1.2 uM (8 uL of 1 mg/mL stock), SYN1327 at 14 uM (1 uL of 1.4 mM stock), SYN1383 at 14 uM (15 uL of 90 uM stock) and SYN571 at 14 uM (1 uL of 1.4 mM stock). SYN571 was able to completely block the binding of shFcRn to HSA. The positive control sample (+HSA) also demonstrated blocking. The lower concentration of HSA competitor explains the incomplete blocking. SYN 1327, a peptide that has been shown to block the binding of IgG to hFcRn (Mezo, PNAS, 2007) was not able to compete for HSA binding. The dimeric form of SYN1327 (SYN1436) resulted in a large increase in signal for shFcRn. SYN1383, which does not block IgG binding to FcRn is also not able to block the binding of shFcRn to HSA, indicating that it binds to a distinct epitope on FcRn
Figure 1B:
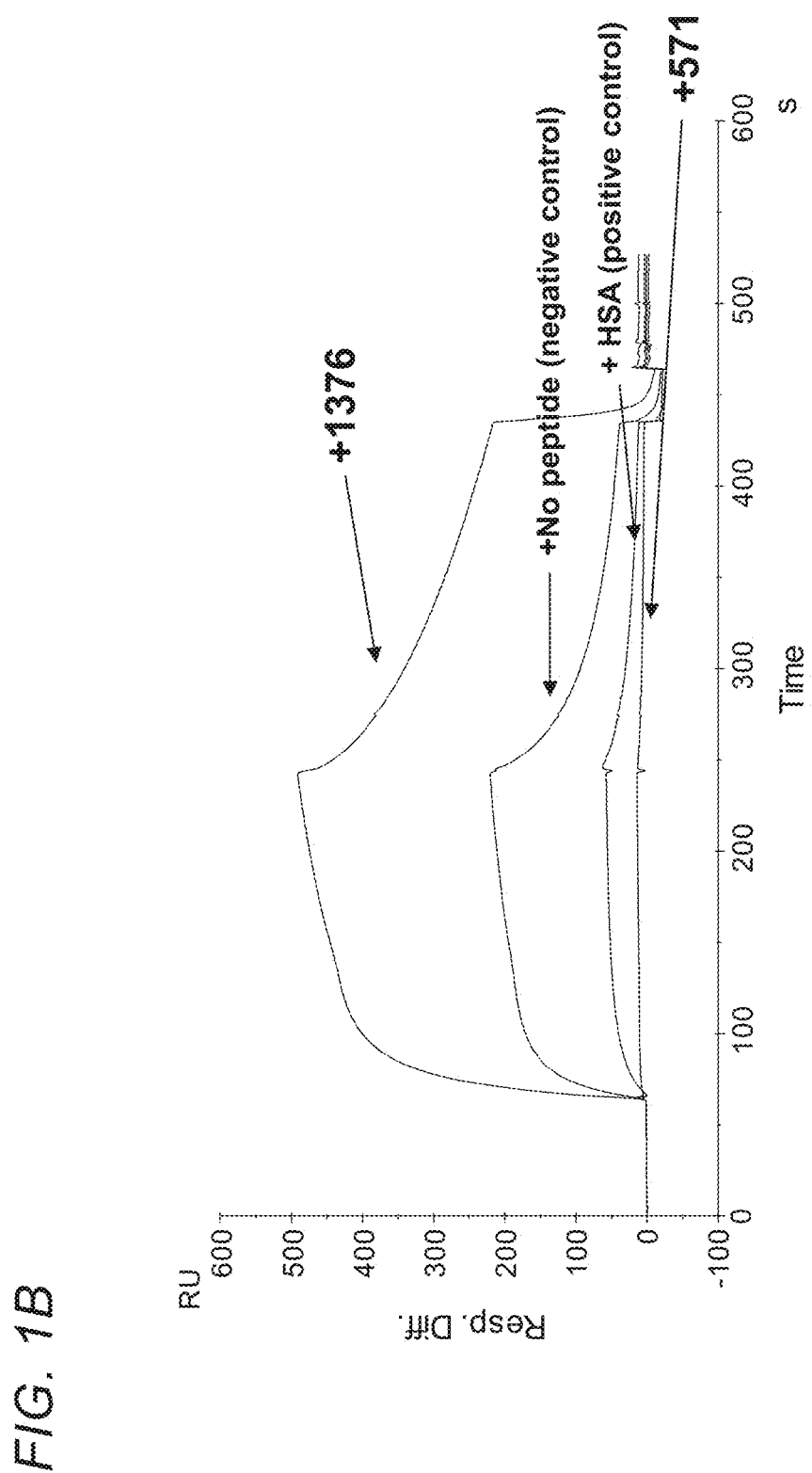
Figure 2A:
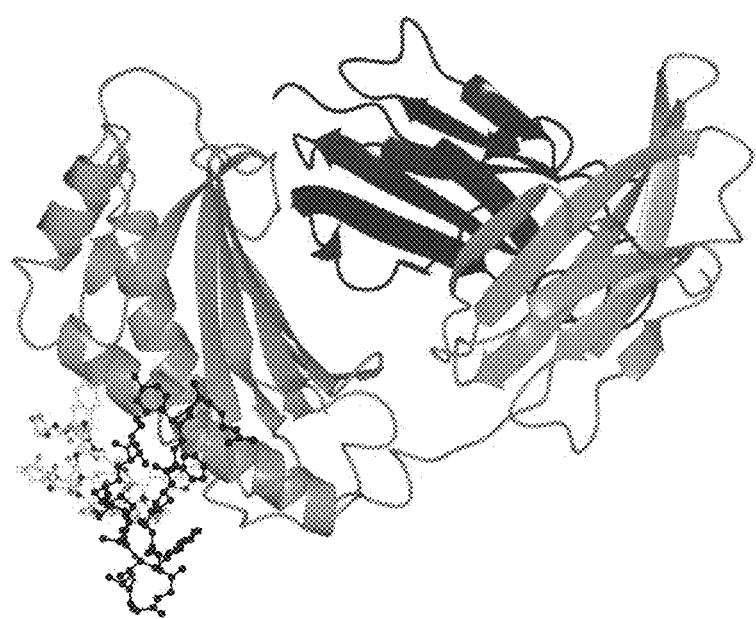
FIGS. 2A-2B depict X-ray Crystallography: SYN1753: shFcRn.
Figure 2B:
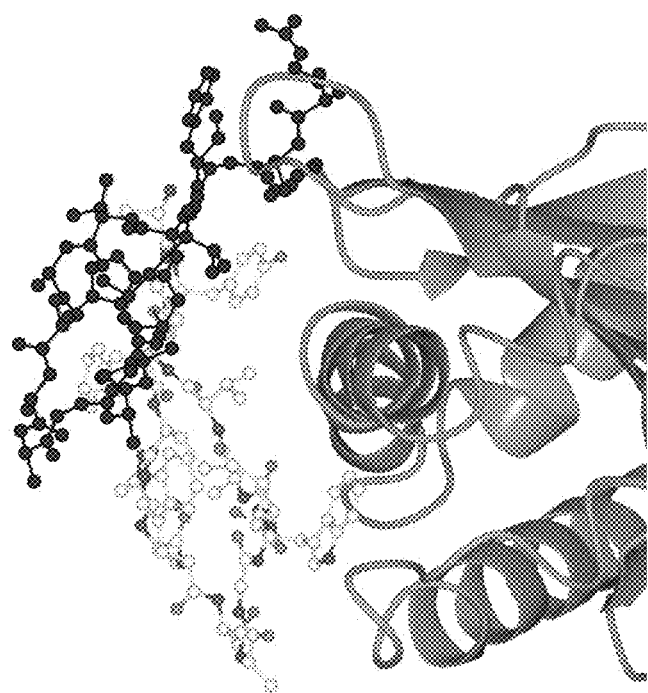

Using phage display screening, we identified peptides capable of specifically blocking the interaction between FcRn and albumin as assessed by surface plasmon resonance (SPR) analyses. In order to do so, a peptide identified in the screen (SYN514 (Ac-AGVMHCFWDEEFKCDQG-GTGGGK-CONH2) (SEQ ID NO: 4) which bound to a unique site (non-IgG, non-albumin competitive) on the FcRn alpha 3 domain as defined by X-ray crystallography was required and utilized in the screen for identifying specific albumin binding peptides. By this means, the peptide SYN571 uniquely bound to FcRn as defined by surface plasmon resonance as compared to peptides blocking the interaction of FcRn with IgG which did not block albumin and vice-versa (FIG. 1). Examination of the structure activity relationship identified a core sequence of the peptide binding to the novel epitope on FcRn and was called SYN1753 (Ac-RYFCTKWKHGWCEEVGT-CONH2 (disulfide), 17-MER (SEQ ID NO:1)) which had a binding affinity of approximately 500 nM at pH 6.0.

Example 2—Procedures Used in the Discovery of SYN-514 and SYN 571 Series of shFcRn-Binding Peptides Selection procedures were adapted from Syntonix lab notebook 164. Routine procedures and most buffers were adapted from Syntonix or Dyax Corp. protocols.

Example 3—Phage Display Selection to Identify SYN514, SYN515 and SYN531

Using phage display screening, the inventors identified peptides ("SYN514", "SYN515" and "SYN531", and their analogs) capable of binding to a non-IgG and non-albumin competitive site on a FCRN alpha 3 domain, which are useful for tracking neonatal Fc receptor FCRN without inhibiting IgG or albumin binding or function Buffers and routine procedures were as described for the discovery of SYN571, except as described below. Round 1 of the selection process was also as described, and is repeated below.

Exemplary Selection Procedure: Round 1: Approximately 100 random library equivalents were pooled according to their titers: 24 µl TN9-IV ($1.3 \times 10^{10}$ pfu/µl), 12.5 µl TN10-X ($1.6 \times 10^{10}$ pfu/µl), 225 µl TN11-I ($1.2 \times 10^9$ pfu/µl), and 48.27 µl TN12-I ($2.9 \times 10^9$ pfu/µl) were mixed with 190.2 µl PBS and 200 µl ice-cold 17% PEG (8000 Da molecular mass, Sigma)+3M NaCl, and incubated on ice for 30 minutes. The phage pool was spun to pellet phage, for 15 min at 12000 rpm in a bench-top microcentrifuge. The supernatant was decanted, and the phage pellet was resuspended in 200 µl buffer BW5. 600 µl streptavidin-coated MG-SA microparticles (Seradyn) were immobilized with a magnetic tube holder. The liquid was decanted, and the beads were washed (by resuspending the beads in buffer, then immobilizing the beads on a magnet and decanting the liquid) 1× with buffer EL, then 2× with buffer BW5. Beads were resuspended in 600 µl BW5 and divided into 6×100 µl aliquots. The library phage were added to 100 µl beads, to remove streptavidin-binding phage. After 10 min. incubation with end-over-end tumbling, the beads were removed. This depletion process was repeated four additional times. Biotinylated FcRn (10 µl of a 1 µM solution, for a 50 nM final concentration) was added to the depleted library pool, and incubated for 1 h at room temperature. MG-SA beads sufficient to bind 500 nM biotin (6.6 µl of the suspension described previously) were added to the library, and incubated at room temperature with tumbling for 30 min. After immobilizing the beads with a magnet, the free-floating phage were decanted and discarded, and the beads were washed 6 times with 1 ml buffer BW5 and one time with 1 ml BW5+50 µM biotin. Bead-bound phage were eluted with 100 µl EL for 30 min. at room temperature with tumbling, and then the beads were immobilized on a magnet and the phage decanted for amplification and additional panning.

Round 2:

Amplified phage output from Round 1 (23.7 µl at $3.92 \times 10^9$ pfu/µl) was diluted in 176.3 µl PBS and precipitated by the addition of 30 µl ice-cold 17% PEG+3M NaCl and 30 min incubation on ice. The phage were pelleted with a 15 min spin at 12000 rpm in a refrigerated microcentrifuge. The supernatant was decanted and discarded, and the phage pellet was resuspended in 200 µl buffer BW5. 400 µl streptavidin-coated MG-SA microparticles (Seradyn) were immobilized with a magnetic tube holder. The liquid was decanted, and the beads were washed (by resuspending the beads in buffer, then immobilizing the beads on a magnet and decanting the liquid) 1× with buffer EL, then 2× with buffer BW5. Beads were resuspended in 400 µl BW5 and divided into 4×100 µl aliquots. The library phage were added to 100 µl beads, to remove streptavidin-binding phage. After 10 min. incubation with end-over-end tumbling, the beads were removed. This depletion process was repeated two additional times (3 times total). Biotinylated FcRn (10 µl of a 0.2 µM solution, for a 10 nM final concentration) was added to the depleted library pool, and incubated for 30 min at room temperature. Two microliters of the resuspended MG-SA beads were diluted in 8 BW5, and then 6.6 µl of the diluted beads (sufficient to bind 100 nM biotin) were added to the library and incubated at room temperature with tumbling for 30 min. After immobilizing the beads with a magnet, the free-floating phage were decanted and discarded, and the beads were washed 10 times with 1 ml buffer BW5 and one time with BW5+50 µM biotin. Bead-bound phage were eluted with 100 µl EL for 30 min. at room temperature with tumbling, and then the beads were immobilized on a magnet and the phage decanted for amplification and additional panning.

Round 3:

Amplified phage output from Round 2 (5 µl at $2 \times 10^{10}$ pfu/µl) was diluted in 195 PBS and precipitated by the addition of 30 µl ice-cold 17% PEG+3M NaCl and a 30 min incubation on ice. The phage were pelleted with a 15 min spin at 12000 rpm in a refrigerated microcentrifuge. The supernatant was decanted and discarded, and the phage pellet was resuspended in 200 µl buffer BW5. 400 µl streptavidin-coated MG-SA microparticles (Seradyn) were immobilized with a magnetic tube holder. The liquid was decanted, and the beads were washed (by resuspending the beads in buffer, then immobilizing the beads on a magnet and decanting the liquid) 1× with buffer EL, then 2× with buffer BW5. Beads were resuspended in 400 µl BW5 and divided into 4×100 µl aliquots. The library phage were added to 100 µl beads, to remove streptavidin-binding phage. After 10 min. incubation with end-over-end tumbling, the beads were removed. This depletion process was repeated two additional times (3 times total). Biotinylated FcRn (10 µl of a 40 nM solution, for a 2 nM final concentration) was added to the depleted library pool, and incubated for 10 min at room temperature. Two microliters of the resuspended MG-SA beads were diluted in 8 µl BW5, and then 6.6 µl of the diluted beads (sufficient to bind 100 nM biotin) were added to the library and incubated at room temperature with tumbling for 15 min. After immobilizing the beads with a magnet, the free-floating phage were decanted and discarded, and the beads were washed 10 times with 1 ml buffer BW5 and one time with BW5+50 µM biotin. Bead-bound phage were eluted with 100 µl EL for 30 min. at room temperature with tumbling, and then the beads were immobilized on a magnet and the phage decanted. The eluted phage pool was then amplified, and the amplified output was screened for FcRn binders using the phage ELISA. Positive phage were amplified for sequencing via PCR, using the protocol above.

One of the phage hits was identified as SYN514 (Ac-AGVMHCFWDEEFKCDQGGTGGGK-CONH2 (disulfide) (SEQ ID NO: 4), which was used in the identification of the SYN571 peptide sequence. Another peptide identified with strong homology to SYN514 was SYN531 (Ac-AGVMK CWWDEEMLCRAFGTGGGK)-CONH2 (SEQ ID NO: 6). Subsequent structure activity relationship analysis of SYN531 revealed the optimized binding sequence SYN1536: Ac-VMKCWWDEEFLCRAF-CONH2 (SEQ ID NO:84).

Example 4—Phage Display Selection to Identify SYN571

Exemplary buffers used—other equivalent buffers may be used:
BW5: 50 mM MES pH 5.5+150 mM NaCl+0.1% Tween 20 (Sigma).
BW6: 50 mM MES pH 6.0+150 mM NaCl+0.1% Tween 20.
BW6+900 µM SYN514: 2 mg/ml SYN514 in BW6.
IG: 133 mM human IgG (Calbiochem) dissolved in 0.5 ml $H_2O$ and dialyzed into buffer BW6.
EL: 50 mM phosphate pH 7.5+150 mM NaCl+0.1% Tween 20.
NZCYM broth: 10 g NZ amine-A, 5 g NaCl, 5 g Bacto yeast extract (Difco), 1 g casamino acids, and 1 g anhydrous $MgSO_4$ were dissolved in 800 ml distilled water. The solution was adjusted to pH 7.5 with 1M NaOH, and then adjusted to 1 liter total volume with distilled water before autoclaving for 20 min.
NZCYMT: NZCYM broth+12.5 µg/ml tetracycline
2×NZCYM broth: 10 g NZ amine-A, 5 g NaCl, 5 g Bacto yeast extract (Difco), 1 g casamino acids, and 1 g anhydrous $MgSO_4$ were dissolved in 400 ml distilled water. The solution was adjusted to pH 7.5 with 1M NaOH, and then adjusted to 500 ml total volume with distilled water before autoclaving for 20 min.
Min-A salts: 10.5 g $K_2HPO_4$, 4.5 g $KH_2PO_4$, 1.0 g $(NH4)_2SO_4$, and 0.5 g sodium citrate were dissolved in 1 liter of water and autoclaved.
LB Broth: 10 g Bacto tryptone, 5 g Bacto yeast extract, and 10 g NaCl were dissolved in 1 liter of water and autoclaved for 20 min.
LB Agar: 10 g Bacto tryptone, 5 g Bacto yeast extract, 10 g NaCl, and 14 g Bacto agar were dissolved in 1 liter of water and autoclaved for 20 min.
LB Soft Agar: 10 g Bacto tryptone, 5 g Bacto yeast extract, 10 g NaCl, and 9 g Bacto agar were dissolved in 1 liter of water and autoclaved for 20 minutes
Exemplary Selection Procedure (SYN571): Round 1:
Approximately 100 random library equivalents were pooled according to their titers: 24 µl TN9-IV ($1.3 \times 10^{10}$ pfu/µl), 12.5 µl TN10-X ($1.6 \times 10^{10}$ pfu/µl), 225 µl TN11-I ($1.2 \times 10^9$ pfu/µl), and 48.27 µl TN12-I ($2.9 \times 10^9$ pfu/µl) were mixed with 190.2 µl PBS and 200 µl ice-cold 17% PEG (8000 Da molecular mass, Sigma)+3M NaCl, and incubated on ice for 30 minutes. The phage pool was spun to pellet phage, for 15 min at 12000 rpm in a bench-top microcentrifuge. The supernatant was decanted, and the phage pellet was resuspended in 200 µl buffer BW5. 600 µl streptavidin-coated MG-SA microparticles (Seradyn) were immobilized with a magnetic tube holder. The liquid was decanted, and the beads were washed (by resuspending the beads in buffer, then immobilizing the beads on a magnet and decanting the liquid) 1× with buffer EL, then 2× with buffer BW5. Beads were resuspended in 600 µl BW5 and divided into 6×100 µl aliquots. The library phage were added to 100 µl beads, to remove streptavidin-binding phage. After 10 min. incubation with end-over-end tumbling, the beads were removed. This depletion process was repeated four additional times. Biotinylated FcRn (10 µl of a 1 µM solution, for a 50 nM final concentration) was added to the depleted library pool, and incubated for 1 h at room temperature. MG-SA beads sufficient to bind 500 nM biotin (6.6 µl of the suspension described previously) were added to the library, and incubated at room temperature with tumbling for 30 min. After immobilizing the beads with a magnet, the free-floating phage were decanted and discarded, and the beads were washed 6 times with buffer BW5 and one time with BW5+ 50 µM biotin. Bead-bound phage were eluted with 100 µl EL for 30 min. at room temperature with tumbling, and then the beads were immobilized on a magnet and the phage decanted for amplification and additional panning.

Round 2:
Twenty-three µl of the amplified phage output ($3.92 \times 10^9$ pfu/µl) were added to 177 µl buffer BW6. 400 µl streptavidin-coated MG-SA microbeads (Seradyn) were immobilized with a magnetic tube holder (Seradyn). The liquid was decanted, and the beads were washed (by resuspending the beads in BW6, then immobilizing the beads on a magnet and decanting the liquid) once with buffer EL, then twice with buffer BW6. Beads were resuspended in 400 µl BW6 and divided into 4×100 µl aliquots. The amplified phage were added to depleted against 100 µl beads 3 times, as described above. The depleted, amplified phage were mixed with 10 µl 0.2 µM FcRn-biotin in BW2+SYN-514 (AG-VMHCF-WDEEFRCEYV-GTGGGK-CONH$_2$) (SEQ ID NO: 116) and incubated for one hour at room temperature so the phage could bind the FcRn-biotin. 2 µl of the unused, washed beads were added to 8 µl buffer BW2, and 6.6 µl of these diluted beads were added to the depleted phage library to bind the FcRn-biotin and attached phage for 30 min at room temperature. The beads were immobilized with a magnet, unbound phage were decanted and discarded, and the beads were washed once 1 ml buffer BW2+SYN514, and then with 9 times with 1 ml BW2. Bound phage were eluted from beads overnight (16 h) with 300 µl buffer IG. The beads were again immobilized and eluted phage were removed from beads, which were then washed once with 100 µl IG and once with 100 µl BW, which were pooled with the eluted phage. The eluted phage pool was then amplified for further investigation.

Round 3:
One µl of the amplified phage output ($1 \times 10^{10}$ pfu/µl) was added to 199 buffer BW6. Four hundred microliters streptavidin-coated MG-SA microbeads (Seradyn) were immobilized with a magnetic tube holder (Seradyn). The liquid was decanted, and the beads were washed (by resuspending the beads in BW6, then immobilizing the beads on a magnet and decanting the liquid) once with buffer EL, then twice with buffer BW6. Beads were resuspended in 400 BW6 and divided into 4×100 µl aliquots. The amplified phage were added to depleted against 100 beads 3 times, as described above. The depleted, amplified phage were mixed with 2 µl 0.2 FcRn-biotin in BW2+peptide SYN-514 (AG-VMHCF-WDEEFRCEYV-GTGGGK-CONH$_2$) (SEQ ID NO: 116) and incubated for 20 min at room temperature so the phage could bind the FcRn-biotin. 2 µl of the unused, washed beads were added to 8 µl buffer BW2, and 6.6 µl of these diluted beads were added to the depleted phage library to bind the FcRn-biotin and attached phage for 33 min at room temperature. The beads were immobilized with a magnet, unbound phage were decanted and discarded, and the beads were washed 10 times with 1 ml BW2. Bound phage were eluted from beads overnight (16 h) with 300 µl A buffer IG.

The beads were again immobilized and eluted phage were removed from beads, which were then washed once with 100 µl IG and once with 100 µl BW, which were pooled with the eluted phage. The eluted phage pool was then amplified, and the amplified output was screened for FcRn binders using the phage ELISA. Positive phage were amplified for sequencing via PCR, using the protocol below.

One of the phage hits was identified as SYN571 (Ac-AGRYFCTKWKHGWCEEVGTGGGK-CONH2 (SEQ ID NO: 3) (disulfide). Subsequent structure activity relationship analysis revealed the minimum binding sequence to be SYN1753: Ac-RYFCTKWKHGWCEEVGT-CONH2 (SEQ ID NO: 1).

Routine Procedures

Phage ELISA: A 2-ml overnight culture of XL1 blue MRF' E. coli was grown from a single colony picked from a streaked plate. The overnight culture was diluted 1:100 into 50 ml NZCYMT and grown to an A600 of 0.5. Agar plugs were picked with sterile Pasteur pipettes from single, isolated colonies on the amplification plate end eluted with 100 ml/well TE for 2 h at 37° C. or overnight at 4° C. in a 96-well round-bottom tissue culture plate (Greiner). Ten microliters phage plug eluate were added to 30 µl XL1 blue MRF' cells and 130 µl NZCYM broth containing 50 µg/ml ampicillin in a 96-well plate, which was incubated overnight at 37° C. A streptavidin-coated, BSA-blocked microtiter plate (Pierce) was rinsed with 200 µl/well buffer A, and then incubated overnight with 1 mg/ml FcRn-biotin in buffer A. The liquid was decanted from the plate, which was then rinsed twice with buffer C. Seventy microliters buffer B and 30 µl overnight phage growth per well were added to the ELISA plate, which was then incubated for 1 h at room temperature. The plate was washed five times with 200 µl buffer C. One hundred microliters buffer C with 1:10000-diluted horseradish peroxidase-conjugated anti-M13 antibody (Amersham Pharmacia) were added to each well of the plate and incubated for 1 h at room temperature. The plate was washed 9 times with 200 ml/well buffer C, and the ELISA was developed with 100 µl/well one-step TMB (KPL). The reaction was stopped when well developed (5-15 min) with 50 µl/well 2M sulfuric acid and read at 450 nm with a Spectra Max Plus plate reader (Molecular Devices).

Phage Amplification.

A 2-ml overnight culture of XL1 blue MRF' E. coli was grown from a single colony picked from a streaked plate. The overnight culture was diluted 1:100 into 50 ml NZCYMT and grown to an A600 of 0.5. The cells were spun at 3500 rpm for 15 min at 4° C. in a Sorvall RT7 centrifuge, and then resuspended in 1/20 volume Min A salts. The eluate from a round of phage display selection (in 500 µl) was added to 500 ml Min A salts and 1 ml of the concentrated bacterial culture for 15 min at 37° C. The phage-infected cells were then added to 2 ml 2×NZCYM broth and then spread on a large NUNC plate containing NZCYM agar with 50 mg/ml ampicillin, until all liquid was absorbed into the agar. The plates were incubated overnight (16 h) at 37° C. The colonies were Twenty milliliters PBS were added to the growth plate, which was gently scraped with a spreader to remove the colonies. PBS with cells and phage were collected in a conical tube. The plate was scraped two additional times, with 10 ml PBS each time, to collect residual phage. All collected phage and cells were pooled and treated to remove cells and concentrate phage. The cells were centrifuged twice at 5000 rpm to pellet the cells, and the clarified supernatant containing phage was decanted each time to a new tube. The phage were precipitated from the PBS by the addition of 0.15 volume 17% PEG+3M NaCl and overnight incubation at 4° C. The phage pellet was resuspended in 5 ml PBS, clarified by centrifugation to remove remaining cell debris, and then pelleted again with 0.15 volume 17% PEG+3M NaCl. This phage pellet was then resuspended in a minimal volume of PBS and tittered in preparation for additional investigation.

Phage Titration.

Phage were diluted in NZCYM broth to achieve dilutions of up to 10'. Typically, this was achieved in increments of $10^{-2}$ (2 µl phage into 198 µl broth). A 2-ml overnight culture of XL1 blue MRF' E. coli was grown from a single colony picked from a streaked plate. The overnight culture was diluted 1:100 into NZCYMT and grown to an A600 of 0.5. Fifty microliters diluted phage were added to 450 µl bacterial culture and incubated for 10 min at room temperature to allow infection to occur. Infected cells were added to 3.5 ml LB soft agar at 55° C. and incubated overnight at 37° C. Titers were calculated as follows from plates with 30-300 plaques: titer in pfu/ml=# plaques/50 µl× dilution used.

PCR Amplification.

Five microliters TE containing phage were added to Taq DNA Polymerase buffer, 200 mM each dNTP, 500 nM each primer, and 1.25 units Taq DNA Polymerase enzyme (from PCR Core System II kit, Promega). Exemplary primers used were 3PCRUP (5'-CGGCGCAACTATCGGTAT-CAAGCTG-3') (SEQ ID NO: 117) and 3PCRDN (5'-CAT-GTACCGTAACACTGAGTTTCGTC-3') (SEQ ID NO: 118). Other primers performing a similar function can be produced and used. The exemplary PCR cycle used was as follows: 94° C. for 5 min, 30 cycles of (94° C. for 15 s, 55° C. for 30 seconds, 72° C. for 1 min), and 72° C. for 7 min. The resulting product was purified using the QiaQuick PCR Prep kit (Qiagen) according to the manufacturer's instructions. Purified product was quantified by spectrophotometry at 260 nm and sequenced with the exemplary primer 3SEQ-80 (5'-GATAACCGATACAATTAAGGCTCC-3') (SEQ ID NO: 119), other sequencing primers can be easily designed and used.

Example 5—Screening FcRn Binding Peptides for Inhibition of HSA Binding to FcRn Using Surface Plasmon Resonance In this experiment, a Biacore sensor chip is coated with human serum albumin (HSA) and then the binding of shFcRn is monitored in the presence or absence of co-injected peptides known to bind to shFcRn. A reduction in the signal of bound shFcRn indicates that the peptide has bound to FcRn in a manner that interferes with its ability to bind to HSA.

SYN1327 is a monomeric peptide that binds to shFcRn with a KD 25 nM and competes for binding of IgG (Fc domain) to FcRn.

SYN1383 is a monomeric peptide that binds to shFcRn with a KD of 32 nM. This peptide has not been shown to be competitive with IgG or any other proteins for FcRn.

SYN571 is a monomeric peptide that binds to shFcRn with a KD of ~500 nM.

SYN1376 is a dimeric form of SYN1327 that has been shown to bind to shFcRn with considerably higher affinity than the monomeric peptide (KD<1 nM).

Human serum albumin (HSA, Albuminar) was immobilized on a Biacore CM5 sensor chip using standard amine coupling conditions. Briefly, the chip surface was activated with EDC/NHS then a 17 ug/mL solution of HSA in 10 mM acetate buffer (pH 5) was injected over the surface resulting in 2500 response units (RU) of protein bound to the chip.

Unreacted sites were then capped by injecting a solution of ethanolamine over the chip surface. A reference flow cell was activated with EDC/NHS and then blocked with ethanolamine.

100 uL samples of 5 uM soluble human FcRn with 14 uM of each FcRn binding peptide were prepared in pH 6 buffer (50 mM phosphate buffer, 100 mM NaCl and 0.01% surfactant P20). Additionally, samples were prepared that had no inhibitor (negative control) or HSA at 1.2 uM (positive control). Samples were injected over the chip for 3 minutes at 20 uL/min followed by a 2.5 minute dissociation phase. The chip was then treated with HBS-P (pH 7.4) for 30 sec at 30 uL/min to remove the bound FcRn and regenerate the HSA chip surface at 30 uL/min with HBS-P. Sensograms were generated by subtracting the reference flow cell data from the HSA flow cell data and compared using BiaEvaluation software to determine the effects of the peptides on FcRn binding.

Results (FIGS. 1A and 1B) show that SYN571 was able to completely block the binding of shFcRn to HSA. The positive control sample (+HSA) also demonstrated blocking. The lower concentration of HSA competitor explains the incomplete blocking. SYN 1327, a peptide that has been shown to block the binding of IgG to hFcRn (Mezo, PNAS, 2007) was not able to compete for HSA binding. This is consistent with the finding that HSA and IgG do not share a common binding epitope on FcRn (Chaudhury, Biochemistry, 2006). Interestingly, the signal for shFcRn binding is slightly increased, which may either signify that binding of SYN1327 modestly increases the affinity of shFcRn for HSA or the increase in signal is due to the increased mass of the peptide:FcRn complex. The dimeric form of SYN1327 (SYN1436) resulted in a large increase in signal for shFcRn. This is likely due to SYN1436 binding to two FcRn molecules at the same time, resulting in a 2 fold increase in the amount of shFcRn bound to the HSA. SYN1383, which does not block IgG binding to FcRn is also not able to block the binding of shFcRn to HSA, indicating that it binds to a distinct epitope on FcRn.

Example 6—Exemplary Peptide Synthesis

Peptides were synthesized by standard Fmoc/tBu protocols on Rink amide resin using commercially available amino acids. Peptides were cleaved from the resin using 95% TFA and 5% triisopropylsilane for 3 hours, and precipitated with ice-cold ether. Disulfides were formed by using 10 equivalents of iodine in acetic acid/water (4:1) for 1 hour at room temperature. In the case of SYN3258, crude peptide was dissolved in 20% DMSO/water in 10 mM sodium acetate pH 5 buffer and mixed for 18 hours at room temperature. Peptides were purified using RP-HPLC (C18) using gradients of acetonitrile in water+0.1% trifluoroacetic acid. Peptide identity and purity was confirmed with analytical RP-HPLC coupled with electrospray MS. In the case of dimer SYN3258, proper disulfide connectivity was confirmed by digestion of the peptide with the endoproteinase Lys-C. SYN3258 (50 ug, 0.5 ug/uL) was treated with Lys-C(5 uL of 0.5 ug/uL), and incubated at 37° C. for 2 hours, followed by analysis by RP-HPLC-MS. A single major peak was observed after digestion, corresponding to a mass of SYN3258+32 Da (MW=4487 Da). The data suggests that the disulfide connectivity was between the expected cysteines, within each peptide monomer.

Example 7—X-Ray Crystallization of SYN1753 with FCRN

SYN1753 was co-crystallized with soluble human FcRn and demonstrated that the peptide formed a dimer in complex with a single FcRn molecule and defined albumin binding epitopes in a pocket on FcRn that centered around several previously identified contact residues on FcRn for albumin; namely Phe157, His161 and His166. The N and C termini of the two bound peptides were in close proximity in the X-ray crystal structure suggesting that a covalent peptide dimer may represent a more optimized peptide to sufficiently block the albumin binding pocket (FIG. 3). Generation of a dimeric peptide was accomplished by fusing two SYN1753 peptides to create SYN3258 (Ac-[SYN1753]-GGG-[SYN1753]-CONH2, a 37 mer (SEQ ID NO:2)) that exhibited a higher affinity for FcRn by SPR (3.6 nM at pH 6.0) as compared to the monomeric peptide SYN1753 (~500 nM at pH 6.0).

Materials and Methods X-Ray.

Protein was prepared. Briefly, the protein was expressed in CHOK1SV cells (Lonza Biologics, Berkshire, UK) and deglycosylated with PNGaseF (NEB Cat. P0705L). Protein was concentrated to 6 mg/ml and incubated with SYN1753 (1 mM) for 1 hour. Crystals were obtained by the hanging drop vapor diffusion by mixing 1 μl of protein:peptide complex and 1 μl of well solution containing 1.6 M ammonium sulfate, 20% glycerol and 0.8 M sodium acetate at room temperature. Crystals were optimized through multiple rounds of seeding.

Data were collected at the Advanced Photon Source (APS, Chicago, Ill.) beam line 22BM and processed with HKL2000 to a resolution of 3.2 A. The structure was solved by molecular replacement using PHASER from the CCP4 program suite in space group I222. The apo structure of FcRn (PDB entry: 1EXU) was used as a search model. Four hFcRn/B2m were placed within the crystal asymmetric unit. Cycles of model refitting using MIFit and refinement using the REFMACS program from CCP4 were carried out. Final data processing and refinement statistics are summarized in Table 4.

TABLE 4

Final data processing and refinement statistics of the shFcRn:SYN1753 complex.

| Data collection | deg-shFcRn:SYN-1753 |
| --- | --- |
| Space group | I222 |
| Unit cell (Å) | 104.9, 176.2, 245.5 |
| Resolution (Å) | 50-3.2 (3.3-3.2)* |
| Wavelength (Å) | 1.0 |
| Observations | 212,585 |
| Unique reflections | 37,736 |
| Completeness (%) | 99.9 (100.0) |
| I/σ(I) | 16.6 (2.7) |
| $R_{merge}$ | 0.111 (0.718) |
| Refinement | |
| Resolution (Å) | 50-3.2 |
| Reflections | 37,733 |
| $R_{work}$ | 0.252 |
| $R_{free}$ | 0.339 |
| No. of protein copies | 4 |
| No. of peptide copies | 7 |
| Rmsd bond lengths (Å) | 0.018 |
| Rmsd bond angles (°) | 1.965 |

*Numbers in parentheses represent data for the last shell of data

Despite the low resolution of the map, continuous density could be traced for 16 of the 17 amino acids in the peptide sequence (aa 1-16). Density features corresponding to large side chains and the disulfide bridge registered the peptide sequence in the electron density. The peptide density is consistent across all protein sites in the crystal. Three of the four molecules in the asymmetric unit clearly showed two peptides bound to a single hFcRn molecule. The fourth showed a single peptide bound, possible because the site is partially occluded by crystal contacts. A final electron density map of the bound peptide pair is shown in FIG. 13C.

Description of Structure of FcRn:SYN1753.

The final crystal structure consisted of four hFcRn/B2m molecules and seven copies of SYN1753. The four hFcRn/B2m molecules are nearly identical with an average root mean square deviation (rmsd) of 0.8 A over an average of 362 aligned Ca atoms. One of the molecules is not well defined in the electron density. Three pairs of peptide SYN1753 are bound at a common site on three of the hFcRn/β2m molecules whereas a single SYN1753 copy is bound at a distinct site on a single hFcRn/β2m molecule. Because the single SYN1753 copy is located at a crystal contact, our analysis focuses on the remaining three complexes.

Figure 13A:
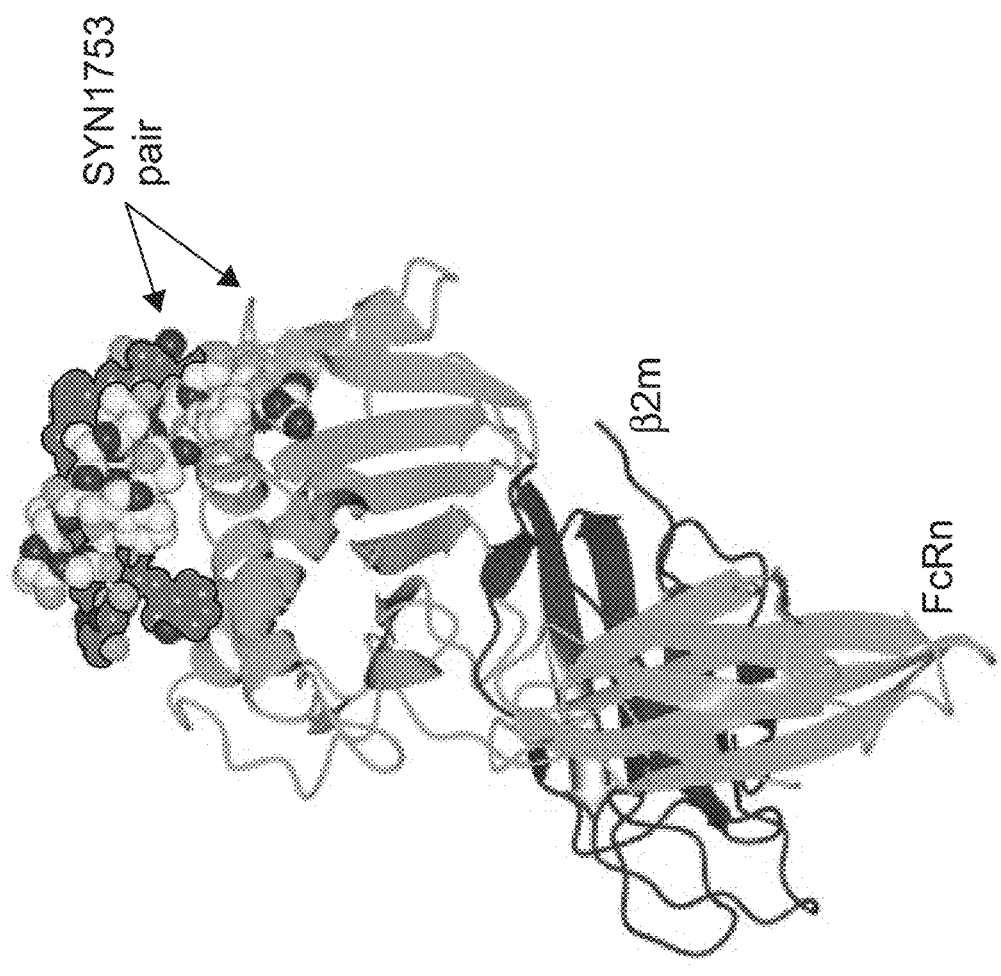
FIGS. 13A-13E depict crystal structure of an albumin blocking peptide (SYN1753) with FcRn and comparison of the binding mode between FcRn and HSA and FcRn with SYN1753.

Pairs of SYN1753 lay on the hFcRn/B2m surface primarily around the side chain of Phe 157 making additional van der Waals contacts with Leu 156 and His 161 (FIG. 13A,B). Each peptide is stabilized by an intramolecular disulfide bridge between SYN-Cys 4 and SYN-Cys 12 and a series of putative hydrogen bonds with the caveat that the peptide planar atomic groups are not adequately defined at this resolution. Similarly, the paired peptides have the potential to form hydrogen bonds and a single copy of the peptide forms putative parallel beta-sheet contacts alongside amino acids 262-266 of the protein.

Figure 13B:
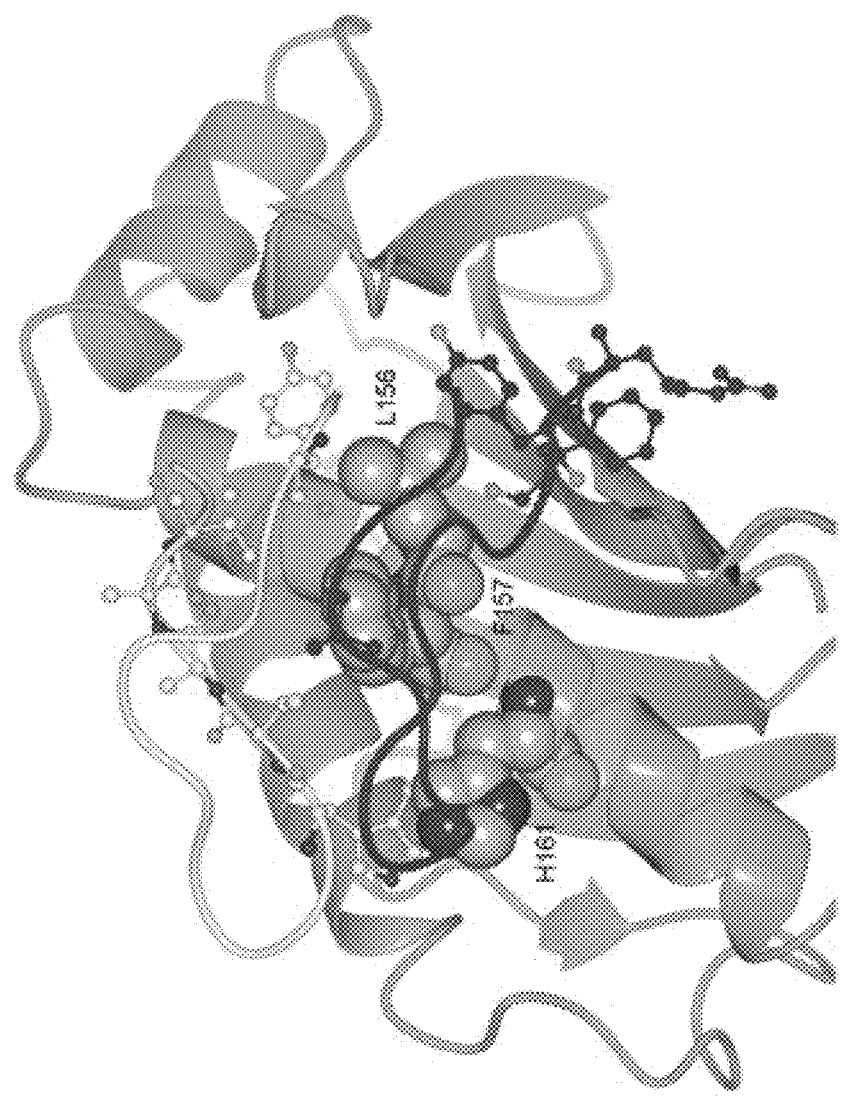
Figure 13C:
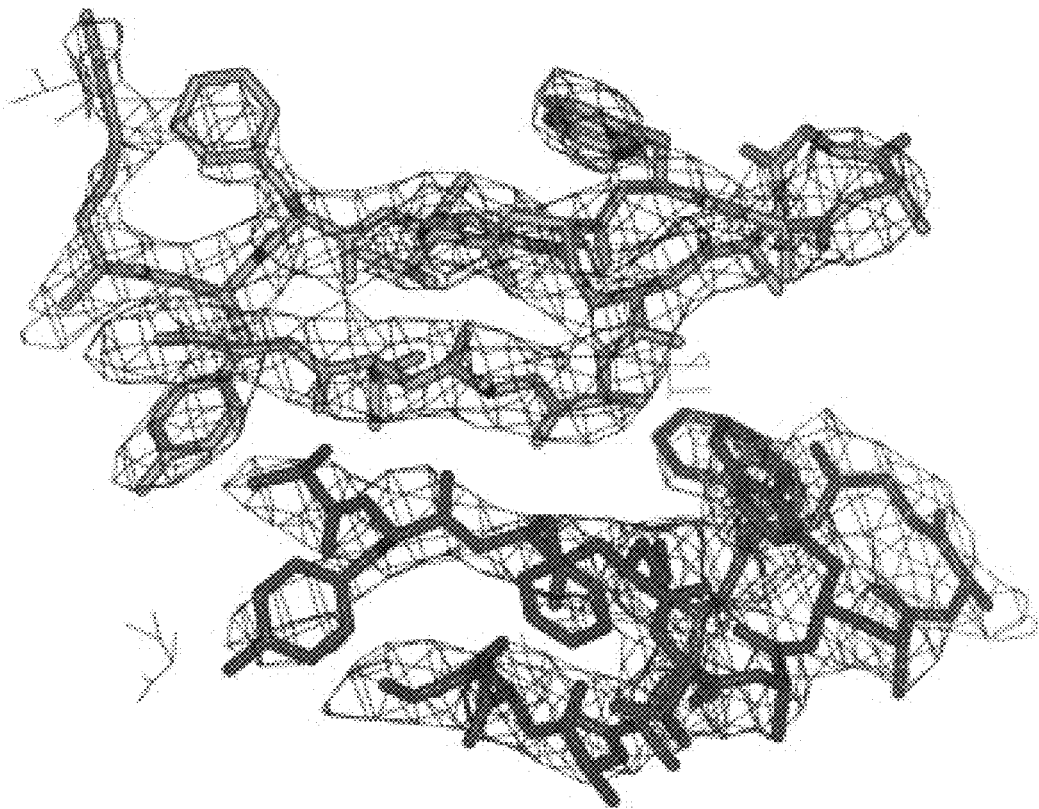
Figure 13D:
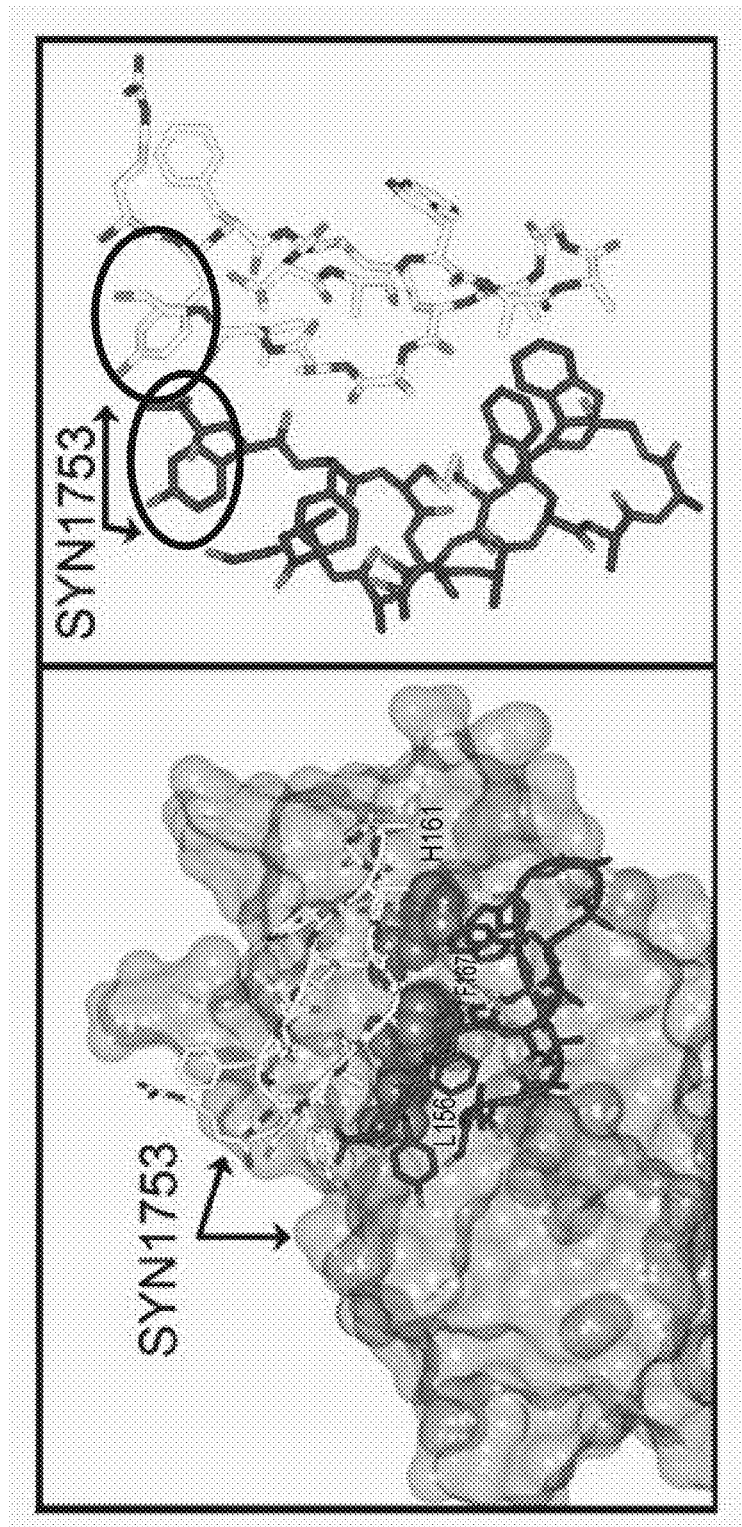

The N- and C-termini of the two bound peptides were in close proximity in the X-ray crystal structure suggesting that a covalent peptide dimer may represent a more optimized peptide to better block the albumin binding pocket (FIG. 13D). A fused peptide was therefore generated by connecting two SYN1753 peptides by a flexible glycine linker to create SYN3258 (Ac-[SYN1753]-GGG-[SYN1753]-CONH2), a 37-mer that exhibited a higher affinity for FcRn by SPR (3.6 nM at pH 6.0) as compared to the monomeric peptide SYN1753 (~500 nM at pH 6.0).

Structural Comparison Between the Peptide Binding Mode and the Complex Structure of hFcRn:HAS.

Figure 13E:
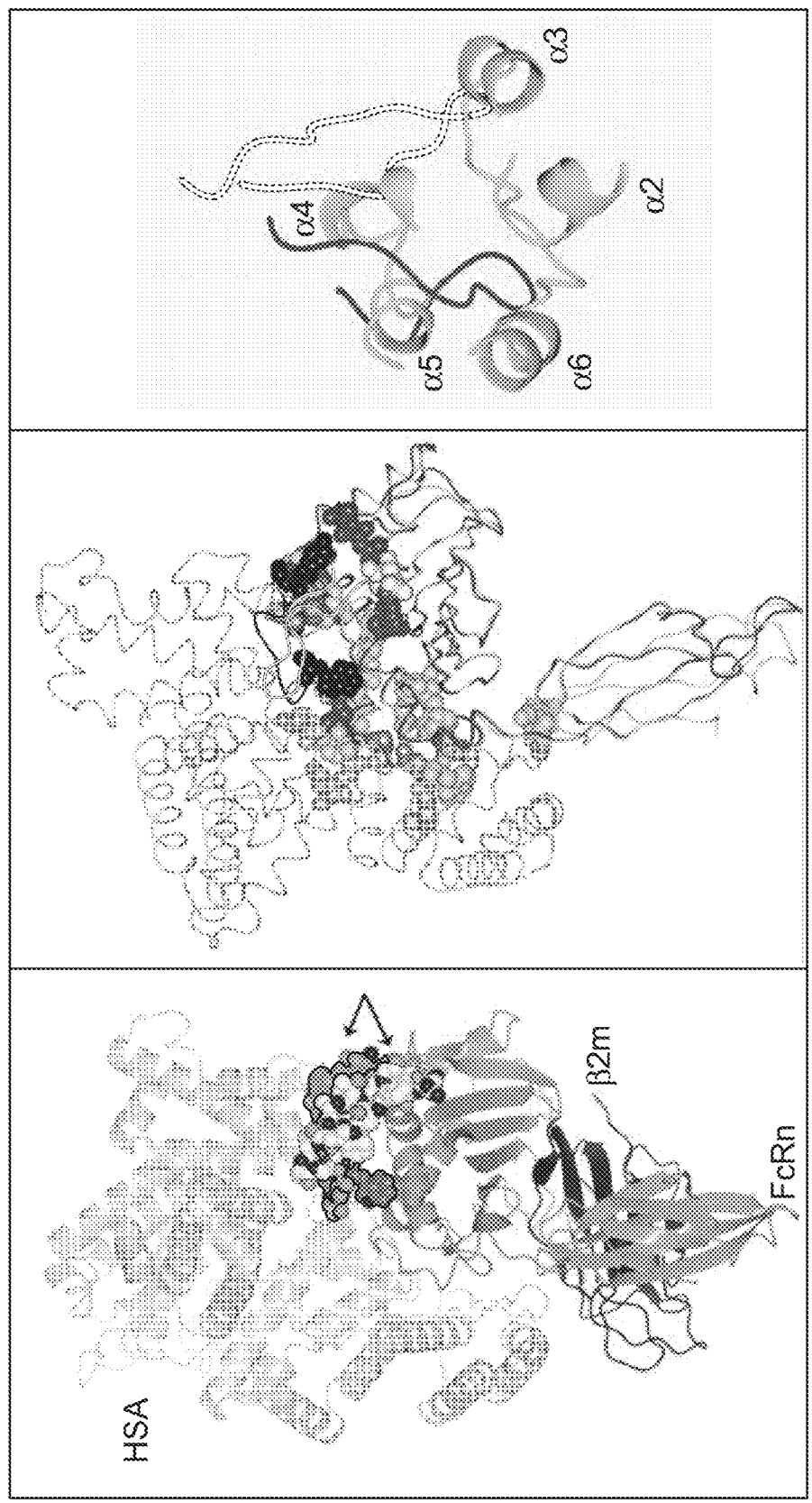

A recent publication provided insights on the interactions between hFcRn and HSA at the structural level (PDB ID: 4K71). In this reported structure complex, domains DI and DIII of a HSA variant make contacts to hFcRn, with domain DIII having an extensive network of interactions (76%) with the end of the α1α2 platform and the hinge in hFcRn, and β2m, in comparison to DI (24%), which has contacts solely with the region surrounding the second structural helix of hFcRn. Comparison of the referred interactions with the ones made between hFcRn and the pair of peptides SYN1753 shows that these bind hFcRn at the same binding site as domain DI of HSA in the complex structure with hFcRn. One peptide overlaps partly with the loop connecting helix 4 and helix 5 in HSA corresponding to the region between residues 78 and 93 of HSA and with half its length starting from its N-terminus located along helix 5 of HSA whereas the second SYN1753 peptide overlaps partly with the loop connecting helices 2 and 3 in HSA corresponding to the region between residues 30 and 36 in HSA as well as the loop connecting helix 4 and helix 5 in HSA (FIG. 13E).

The recently published model of hFcRn and HSA confirms the importance of the previously identified critical residues in HSA for the interaction with hFcRn (namely Lys500, His464, His510, His535, Glu531 in HSA) and revealed a newly found striking feature consisting of the insertion of two absolutely conserved hFcRn tryptophans into deep hydrophobic pockets in the domain DIII of HSA. The model of hFcRn:HSA reveals critical residues in hFcRn for the interaction with HSA and include, in addition to Glu54, Asp101, Phe157, His161, His166 and Glu168 as previously identified residues, Ser58, Trp59, Lys63, Asn149, Lys150, Leu152, Thr153 and Glu165 which bind DI, and Arg42, Glu44, Glu46, Pro47, Gly49, Ala50, Val52 and Trp53 which bind DIII. Interestingly, the pair SYN1753 makes critical binding contacts with many of the newly identified residues that bind DI, as described previously (FIG. 13E)

Example 8—Bioassay for Peptides that Block FCRN-Dependent Albumin Transcytosis

Figure 9:
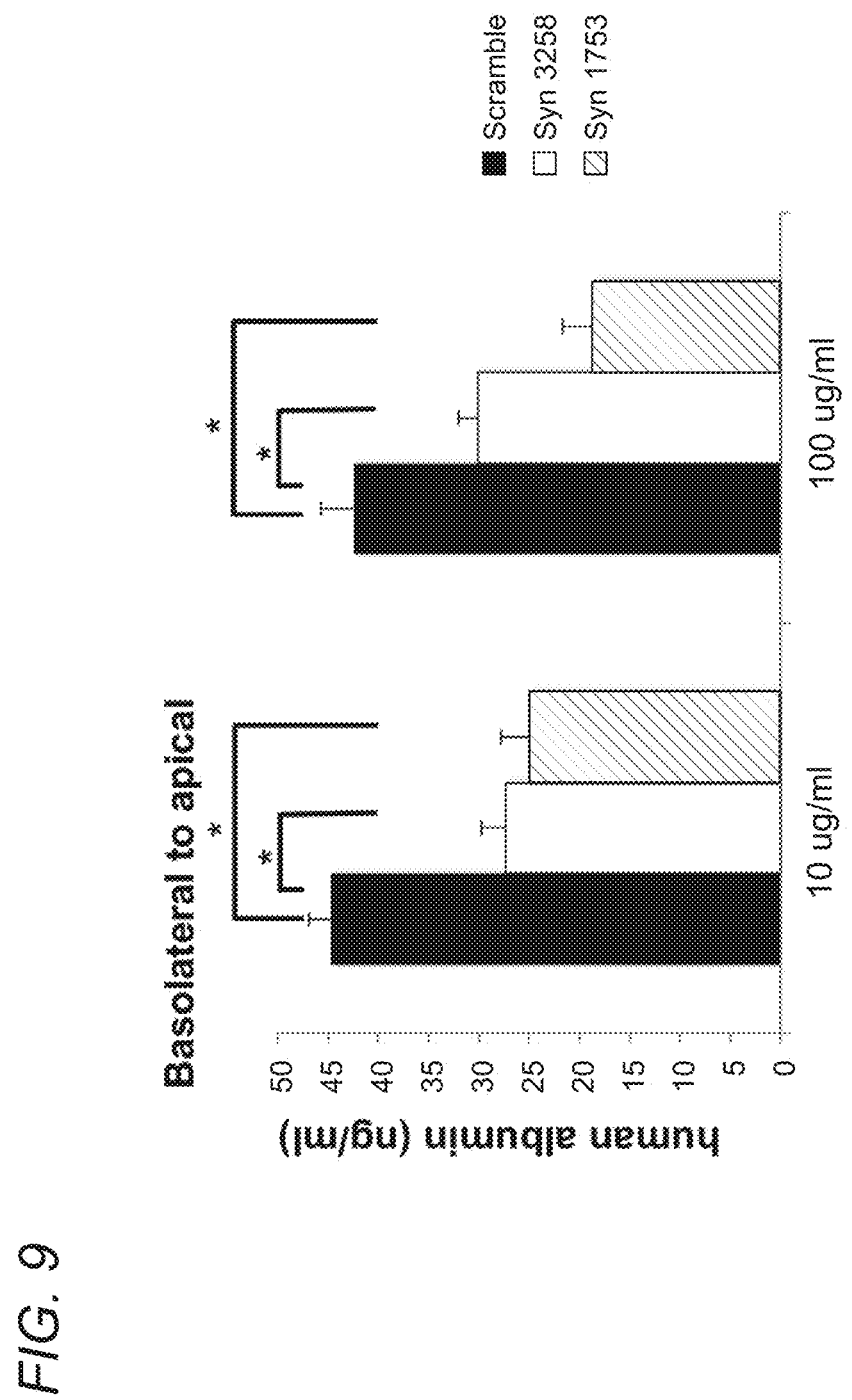
FIG. 9 shows that Syn1753 and Syn3258 specifically block FcRn mediated transcytosis of human albumin. The 15 amino acid peptide inhibitor SYN1753 and the dimeric peptide inhibitor Syn3258 are both capable of significantly reducing human FcRn-mediated transcytosis of human albumin across polarized epithelia compared to a scrambled peptide, as shown in MDCK cells expressing human FcRn and human β2microglobulin. *: p≤0.05

In a bioassay of FcRn dependent albumin transcytosis using madin darby canine kidney cells transfected with human FcRn and beta-2-microglobulin, both SYN1753 and SYN3258, but not a scrambled peptide, were capable of blocking transcytosis of human albumin. (FIG. 9).

Example 9

Alanine-scanning of the SYN1753 peptide revealed that the following residues are particularly important for binding: Tyr2, Cys4, Trp7, Gly10, Trp11, Cys12, and Val15.

Example 10

Figure 10A:
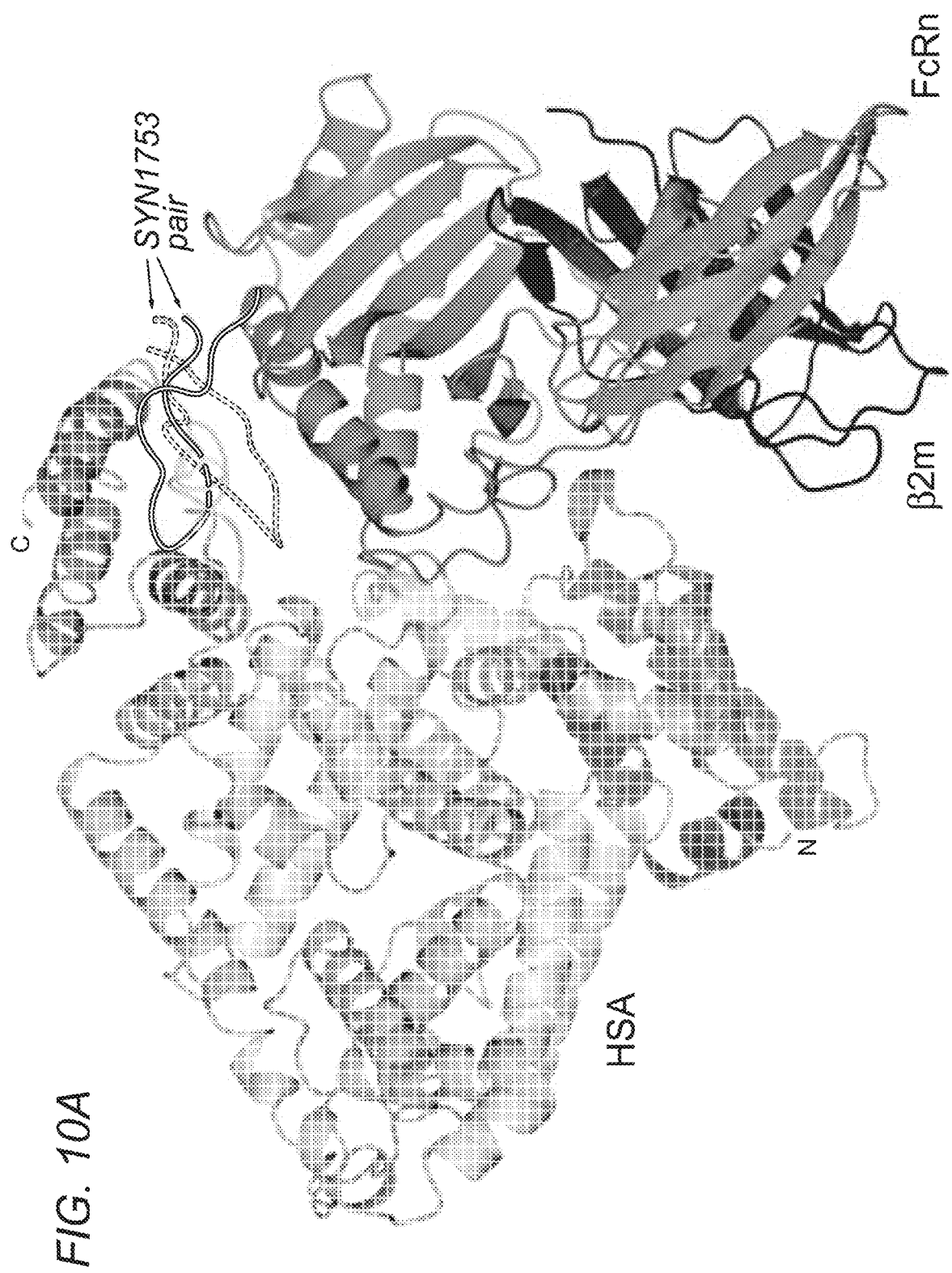
FIGS. 10A-10B depict best solution model for the interaction between hFcRn and HSA.
Figure 10B:
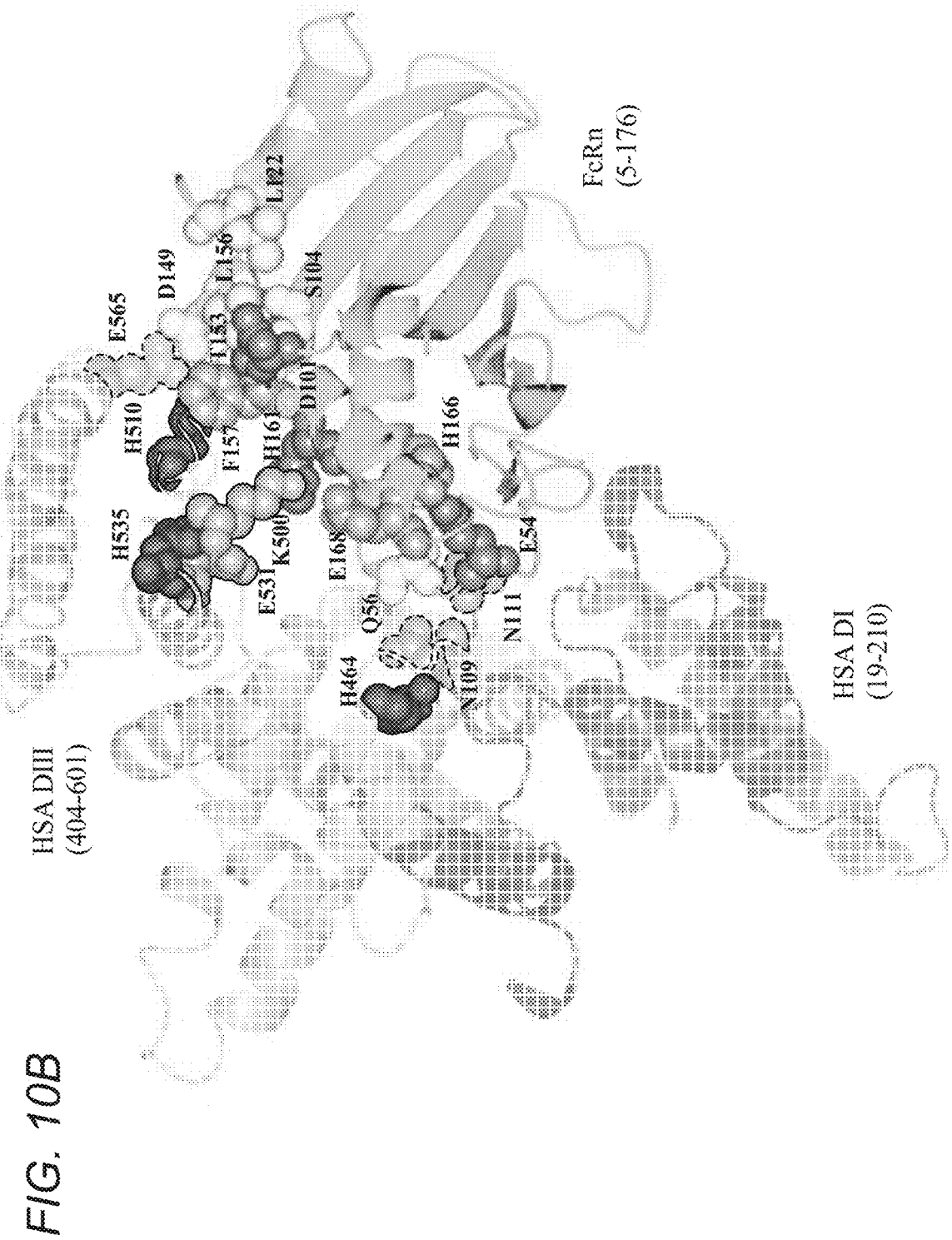

A structural model of the complex model between the human neonatal Fc receptor (hFcRn) and human serum albumin (HSA) was enabled and generated using the program ZDOCK (Pierce B G, Hourai Y, Weng Z. (2011) *Accelerating Protein Docking in ZDOCK Using an Advanced 3D Convolution Library*. PLoS One 6(9): e24657) based upon the docking interactions between SYN1753 and hFcRn (FIG. 10A), and using the structural model hFcRn:SYN1753 and a previously published HSA structural model (PDB ID 1BM0) for the search. The program was run with selected residues from both structures in agreement with knowledge regarding binding and the relevant residues for peptide binding. For generation of the docking solutions, residues Leu122, Thr153 and His161 in hFcRn and residues His464, His510 and His535 in HSA were selected as relevant contacts in the protein-protein binding interface. The best solution reveals that the pair of peptides SYN1753 binds hFcRn at the same binding site as domain DIII of HSA. One of the peptides SYN1753 from the bound pair overlaps partly with the recognition loop in the region between residues 508 and 517 in HAS, whereas the other overlaps partly with the recognition loop between residues 502 and 509 in HSA. Regarding critical residues in HSA for the interaction with hFcRn, in addition to Lys500, His464, His510, His535, Glu531 which were previously identified by Andersen and colleagues (Nature Communications 2011), our model predicts that Glu565, Asn111 and Asn109 in HSA are also relevant for FcRn binding (FIG. 10B). This model predicts that critical residues in hFcRn for the interaction with HSA include, in addition to Glu54, Asp101, Phe157, His161, His166 and Glu168 (as identified by Andersen and colleagues, Nature Communications 2011), Thr153, Asn149, Leu122, Leu156, Gln56 and Ser104 as identified by here.

Human Albumin Amino Acid Sequence (SEQ ID NO:8):
DAHKSE VAHRFKDLGE ENFKALVLIA FAQYLQQCPF EDHVKLVNEV TEFAKTCVAD ESAENCDKSL HTLF-GDKLCT VATLRETYGE MADCCAKQEP ERNEC-FLQHK DDNPNLPRLV RPEVDVMCTA FHDNEETFLK KYLYEIARRH PYFYAPELLF FAKRYKAAFT ECCQAADKAA CLLPKLDELR DEGKASSAKQ RLKCASLQKF GERAFKAWAV ARLSQRFPKA EFAEVSKLVT DLTKVHTECC HGDLLECADD RADLAKYICE NQDSISSKLK ECCEKPLLEK SHCIAEVEND EMPADLPSLA ADFVESKDVC KNYAEAKDVF LGMFLYEYAR RHPDYSVVLL LRLAKTYETT LEKCCAAADP HECYAKVFDE FKPLVEEPQN LIKQNCELFE QLGEYKFQNA LLVRYTKKVP QVSTPTLVEV SRNLGKVGSK CCKHPEAKRM PCAEDYLSVV LNQLCVLHEK TPVSDRVTKC CTESLVNRRP CFSALEVDET YVPKEFNAET FTFHADICTL SEKERQIKKQ TALVELVKHK PKATKEQLKA VMDDFAAFVE KCCKADDKET CFAEEGKKLV AASQAALGL.

Example 11—Material and Methods

Vectors and cells: MDCK II cells expressing rat or human 132m and FcRn as described previously (20, 40). Human albumin gene was cloned from HepG2 cells, sequence confirmed, and inserted into pBUD4.1 vector (Invitrogen). This was transfected into MDCK II cells expressing either human β2m only or both hβ2m and hFcRn. Stable clones were selected by zeocin resistance and ring cloning. The medium of the cells were DMEM (Cellgro) with 10% FBS.

Proteins and Reagents:

Human albumin (Abserotec) and rat albumin (Innovative Research), human IgG (Lampire), rat IgG (Lampire) were used for in vitro transport and in vivo experiments. The albumin and IgG levels were measured using ELISA (Bethyl Lab). Acetaminophen level was determined using Acetaminophen LiquiColor Test (Stanbio). ALT levels were measured using ALT/SGPT Liqui-UV test (Stanbio). HBSS (Sigma) was adjusted to pH 6 or pH 7.4 using HCl or NaOH. FITC-dextran-70 (Sigma) was diluted in PBS. Peptide inhibitors, SYN1753 and SYN3258 (Biogen Idec), were diluted in distilled $H_2O$. The scrambled peptide used in transcytosis experiments was a 15 amino acid molecule generated by random rearrangement of SYN1753 sequence. The control peptide used in in vivo experiments contained the dimeric structure of SYN3258 in which three amino acids in each monomer were mutated in the following way: W7A, W11A, V15A.

For SPR analysis, recombinant human albumin (Sigma) expressed by *Pichia pastoris* and rat albumin (Sigma) were used. Soluble human FcRn was expressed and purified by Biogen-Idec as previously described (29). The Fc fragment of IgG1, designated as CysFc, was used as a surface plasmon resonance control (SPR) control and was expressed in CHO cells and purified by protein A affinity chromatography (Biogen-Idec).

Animals:

All animal experiments were approved by the IACUC committee of Harvard Medical School and housed in approved SPF facilities. Wild-type BALB/C and C57BL/6 mice (Charles River Lab) were used. FcRn deficient mice and mice that express hFcRn and hβ2m transgenes in the absence of endogenous FcRn were previously generated.

Transcytosis, Recycling, and Secretion Assays:

Albumin transcytosis assays were performed as previously described for IgG. In brief, MDCK II cells expressing $h\beta_2m$ and hFcRn were grown to confluence on transwells (Costar) and allowed to polarize over 4 days. 12 hours before the transcytosis experiment, the medium was changed to serum-free media without antibiotics. On the day of experiment, the transwells were incubated with HBSS pH 7.4 for 20 minutes before placing on a new 12 well plate (Costar) where the input chamber contains HBSS pH 6.0 and the exit chamber contains HBSS pH 7.4 and pH adjusted albumin was added to the input chamber afterwards. For blocking albumin transcytosis with the peptide inhibitors SYN1753 and SYN3258, transwells were pre-incubated for 20 min with the respective peptides in HBSS pH 6.0 prior to the addition of albumin in the continued presence of the peptides. After incubating for 2 hours in 37° C. and 5% $CO_2$, the medium at the opposite chamber were harvested and the albumin concentration was measured using ELISA method. For the recycling assay, the transwells were washed with HBSS pH 7.4 for 5 minutes before placing on a new 12-well plate with HBSS pH 6.0 at both chambers. After equilibration at 37° C. and 5% $CO_2$, pH adjusted albumin human albumin was added and allowed to incubate for one hour. The transwells were then washed at HBSS pH 6.0 before placing in a new 12-well plate with HBSS pH 7.4 at both chambers. After one hour incubation, medium from the input chamber was removed and the albumin concentration was measured by ELISA. For the human albumin secretion assay the medium was changed to serum- and antibiotic-free media on the day of the experiment. 50 μL of the medium from both chambers were removed periodically over 24 hours, and the human albumin concentration was measured using ELISA with volume reduction adjustment.

HPLC Analysis:

Bile pooled from four $Fcgrt^{-/-}$ mice were isolated and combined. Albumin was separated from the bile with anti-mouse albumin antibody conjugated to Protein G Sepharose (GE). After 20 hours, the sepharose conjugates were washed with PBS twice, resuspended in 8 U/mL Pronase E, and incubated at 50° C. for 15 hours. After protease digestion, the supernatant was removed, diluted 1:4 in 20% TCA, and incubated on ice for 10 minutes to precipitate undigested protein. The samples were then spun for 10 minutes at 14,000 g at 4° C. Supernatant was reserved. HPLC Analysis of APAP was performed as described previously using UV detection in place of electrochemical detection (41). The analysis was performed at room temperature on a Beckman System Gold HPLC system with Solvent Module 125 and Programmable Detector Module 166. The mobile phase was 50 mM Sodium Acetate and 7% Methanol at pH 4.8. The flow rate was 1 ml/min through a reversed-phase TSK-GEL-ODS-80Tm column (4.6 mm×25 cm; TOSOHASS, Montgomeryville, Pa.). Run time was 30 minutes. An absorbance spectrum of 20004 APAP was run on a Beckman DU-640 spectrophotometer and a detection wavelength of 250 nm was selected. 204 of 20004 APAP in 10 mM Sodium Acetate was run to identify the retention time, and the sample volume was also 204.

In vivo acetaminophen toxicity experiments: Acetaminophen (Sigma-Aldrich) was diluted in PBS at a concentration of 33.3 mg/ml. The acetaminophen dose of 600 to 700 mg per kg body weight administered i.p. was found to be lethal, as titrated in dose-findings experiments. In blocking experiments using antibody administration, ADM31 or isotype control were administered 14 h prior to the injection of APAP. For blocking the interaction between FcRn and albumin via peptide, a cyclic control peptide for SYN3258 was designed in which three key residues per monomer that were identified by alanine screening to be critical for binding between FcRn and albumin were mutated to alanines (W7A, W11A, VISA). SYN3258 or the control peptide were then continuously administered at a dose of 40 mg/kg body weight per day via i.p. osmotic pumps (Alzet, Cupertino, Cat. No 1003D) over a 72 hour period. Prior to the surgical implantation of the pumps, mice were anaesthetized with Buprenex (0.1 mg/kg body weight) s.c. and Ketamine HCl (100 mg/kg)/Xylazine (10 mg/kg) i.p. Hair on the incision site was clipped and the implantation area was disinfected by 5% iodine in 70% isopropanol. Antibiotics (100 µg/ml of gentamycin) were sprayed on the area of incision to prevent infection, and skin was sutured using polypropylene suture. Total duration of the surgical procedure was around 5 minutes per mouse. 18-20 hours after pump implantation, a lethal dose of acetaminophen was administered i.p.

SPR Analyses:

SPR analyses were conducted using a Biacore 3000 or T100 instrument. Research-grade CM5 sensor chips and all coupling reagents for immobilization were purchased from Biacore. All proteins were cross-linked to the dextran surface of a CM5 sensor chip by standard amine coupling chemistry as recommended by Biacore. For immobilization, soluble human FcRn (10 µg/mL) was diluted in 10 mM sodium acetate, pH 4.5. Soluble human FcRn was covalently coupled to a final density around 500 Resonance Units (RU), using HBS-P running buffer (10 mM HEPES, pH 7.4, 150 mM NaCl and 0.05% surfactant P20). Binding experiments were performed at pH 6.0 or 7.4 using 50 mM phosphate, 100 mM sodium chloride and 0.01% surfactant P20. A typical experiment for determining the affinity of rat or human albumin towards soluble human FcRn was as follows: albumin was injected in 12 concentrations ranging from 50 nM-100 µM in duplicate simultaneously over all flow cells under 25 or 50 µL/min flow rate for 5 min. Bound albumin protein was then allowed to dissociate from the chip for 5 minutes with running buffer. Any remaining albumin was removed from the chip with a 60 second injection (2 cycles) of pH 8.0 Tris-HCl regeneration buffer (1 M Tris pH 8.0) at 25 µL/min flow rate. The binding responses recorded near the end of the association phase were plotted as a function of concentration. Equilibrium dissociation constants (KD), were derived from sensorgrams using the 1:1 binding model of BIAevaluation software 4.1.

Phage Display:

Peptide phage libraries, obtained from Dyax Corp, were screened against biotinylated soluble human FcRn bound to streptavidin beads, using 3 rounds of sequential pH 6.0 binding and pH 7.5 elution/amplification protocols. Using this method, a series of peptides were identified, including SYN514 (Ac-AGVMHCFWDEEFKC DQGGTGGGK-CONH2) (SEQ ID NO: 4), and its truncated and SAR-optimized analog SYN1383 (Ac-VMHCFWDEEFRCEYV-CONH2) (SEQ ID NO:55) which were determined using competition experiments and X-ray crystallography to bind to shFcRn at a unique site on the alpha 3 domain (non-IgG, non-albumin competitive). Peptide SYN514 was utilized during a 2$^{nd}$ peptide phage screen to occupy this site on FcRn prior to the addition of the phage libraries, and to identify albumin-competitive sequences. This strategy uncovered the albumin-competitive peptide, SYN571, and through structure-activity relationships, the shorter sequence SYN1753 (Ac-RYFCTKWKHGWCEEVGT-CONH2 (SEQ ID NO: 1) (disulfide) which bound to shFcRn with equivalent affinity as determined by SPR.

Results

Figure 11B:
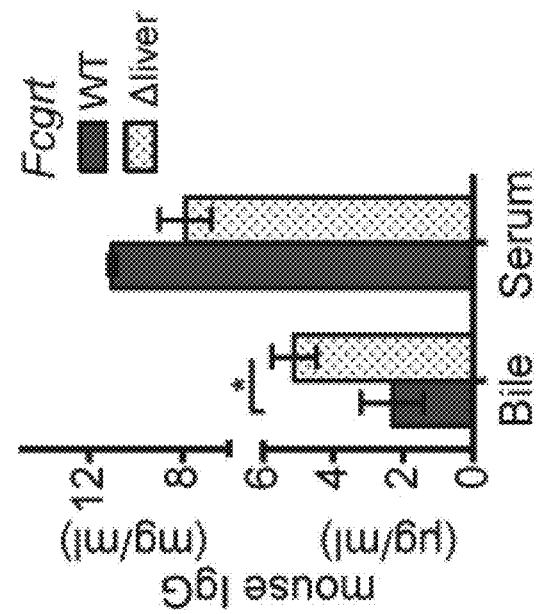
FIGS. 11A-11B shows that FcRn deficiency causes a protein losing biliopathy specific for albumin and IgG. Serum and bile levels of mouse albumin and IgG in WT and mice with hepatocyte-specific deletion of Fcgrt (Fcg$^{\Delta liver}$) (n=3-5 mice per group, *, P=0.0267, **, P=0.0082). Data were statistically analyzed by unpaired Student t-test.
Figure 11A:
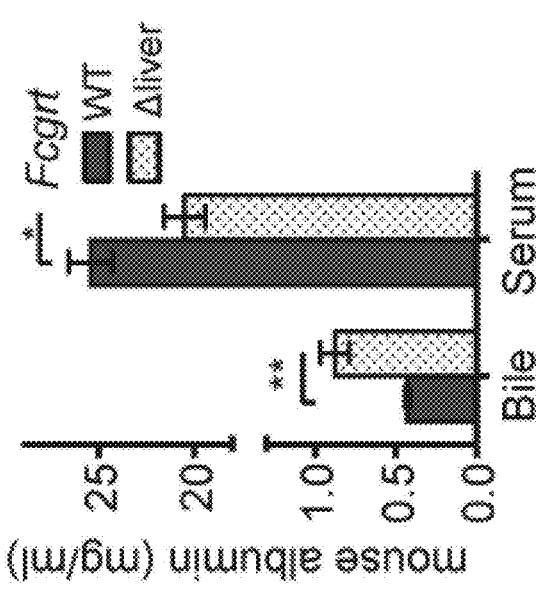

To first examine how FcRn accomplishes albumin homeostasis, we examined the endogenous levels of albumin and IgG in the bloodstream and bile of wild-type (WT) and FcRn-deficient (Fcgrt$^{-/-}$) mice. Decreased levels of serum albumin and IgG were detected in Fcgrt$^{-/-}$ mice compared to Fcgrt$^{+/+}$ (WT) and FcRn-heterozygous (Fcgrt$^{+/-}$) mice on both, BALB/c and C57BL/6 background (data not shown). Despite the presence of hypoalbuminemia and hypogammaglobulinemia in Fcgrt$^{-/-}$ mice, the levels of mouse albumin and IgG detected in the gallbladder-associated bile were significantly higher in mice that lacked FcRn expression relative to that observed in WT and heterozygous littermate controls (data not shown). Further, hepatocyte-specific deletion of Fcgrt by crossing previously described Fcgrt$^{fl/fl}$ mice with albumin-Cre expressing transgenic mice to generate Fcgrt$^{\Delta hepatocyte}$ mice caused a similar increase in bile-associated albumin and IgG (FIG. 11A,B). Interestingly, Fcgrt$^{\Delta hepatocyte}$ mice exhibited a significant decrease in serum albumin to levels nearly as low as that observed in Fcgrt$^{-/-}$ mice demonstrating the major role played by hepatocytes themselves in maintaining serum levels of albumin (FIG. 11A). To confirm these observations, we performed tracer studies wherein rat albumin and human IgG, which are both known to bind mouse FcRn, were administered intravenously (i.v.) via the tail vein. Serum levels of human IgG (data not shown) and rat albumin (data not shown) were significantly lower in Fcgrt$^{-/-}$ mice as compared to WT mice. Despite this, the levels of human IgG (data not shown) and rat albumin (data not shown) in the bile were significantly elevated in Fcgrt$^{-/-}$ mice compared to that detected in WT mice. To further extend these observations to human FcRn, we took advantage of previously described humanized mice that express human (h) FcRn and hβ2-microglobulin but lack mouse FcRn expression (hFCGRT$^{Tg}$/hB2m$^{Tg}$/mFcgrt$^{-/-}$ mice) (1, 7). Consistent with the ability of hFcRn to bind mouse albumin but not mouse IgG and the major contribution of serum albumin to the quantity of total serum proteins, reconstitution of hFcRn and hβ2-microglobulin expression in Fcgrt$^{-/-}$ mice (hFCGRT$^{Tg}$/hB2m$^{Tg}$/mFcgrt$^{-/-}$) resulted in normalization of total protein levels to that observed in WT mice in contrast to Fcgrt$^{-/-}$ which exhibited significantly reduced total protein levels (data not shown). Total protein levels in the bile, however, exhibited a trend to be increased in Fcgrt$^{-/-}$ mice relative to that observed in WT and hFCGRT$^{Tg}$/hB2m$^{Tg}$/mFcgrt$^{-/-}$ mice (data not shown). More directly, and consistent with the cross-species binding of hFcRn to mouse albumin, hFCGRT$^{Tg}$/hB2m$^{Tg}$/mFcgrt$^{-/-}$ and WT mice exhibited similar levels of endogenous albumin in both bile and serum (data not shown) compared to that observed in Fcgrt$^{-/-}$ mice. These studies indicate that hFcRn expression can reverse the albumin loss into the bile that is observed in Fcgrt$^{-/-}$ mice. Finally, the observed increases in bile protein and albumin in particular were not due to nonspecific increases in protein permeability in the livers of FcRn-deficient mice as no differences in the levels of FITC-dextran with a molecular weight (MW) of 70-kDa, the approximate MW of albumin (66-kDa), were observed in the bile or serum of Fcgrt$^{-/-}$ mice in comparison to that observed in WT mice at 24 hours after i.v. tail vein injection (FIG. 1J). Together, these studies indicate that Fcgrt$^{-/-}$ mice exhibit a protein losing biliopathy that is highly specific for albumin and IgG.

We next sought to understand the mechanisms by which FcRn functioned to maintain albumin in the circulation and prevent its loss into the bile at its site of synthesis within hepatocytes of the liver. We first examined the distribution of FcRn in hepatocytes under steady-state conditions in vivo in hFCGRT$^{Tg}$/hB2m$^{Tg}$/mFcgrt$^{-/-}$ relative to Fcgrt$^{-/-}$ mice. We observed that the majority of hFcRn was distributed intracellularly in a vesicular pattern within hepatocytes similar to that described in other polarized epithelial cell types, with signals also detected on both the sinusoidal (basal) and canalicular (apical) membranes in hepatocytes of hFCGRT$^{Tg}$/hB2m$^{Tg}$/mFcgrt$^{-/-}$ (data not shown), but not in isotype control stained livers (data not shown) or mFcgrt$^{-/-}$- mice (data not shown). Together, these data demonstrate that FcRn is expressed in juxtaposition to both the bile and bloodstream on the canalicular and sinusoidal surfaces, respectively, in hepatocytes in vivo.

Since FcRn in hepatocytes was localized on polarized membranes adjacent to bile and blood and that such a distribution has been previously linked to the bidirectional transcytosis of IgG in other cell types, we sought to determine whether FcRn was also able to traffic albumin in a similar manner. In the absence of well-validated polarized cell lines that model hepatocytes, we examined the transcytosis of human or rat albumin in madin darby canine kidney II (MDCK II) cells transfected with either hFcRn and hβ2m or rat (r) FcRn and rβ2m, as well as their respective vector controls (MDCK II cells transfected with either hβ2m or rβ2m alone), and which we have previously used to model the transcytosis of IgG. Bidirectional transport of human (data not shown) and rat (data not shown) albumin by the hFcRn transfected, but not vector control cells, was observed, consistent with the cross-species binding of hFcRn to rodent albumin, and confirmed by the ability of rat FcRn to also perform the bidirectional transcytosis of albumin (data not shown). Together, these studies demonstrate that rodent and human FcRn mediate the bidirectional transcytosis of albumin in a polarized epithelial model system suggesting FcRn is involved in both the apically-directed secretion as well as retrieval of apically disposed albumin.

To understand the steady-state and potential physiologic consequences of FcRn expression on the disposition of albumin given its ability to transcytose albumin in a bidirectional manner similar to previous observations with IgG transcytosis, we examined the effects of FcRn on the net accumulation of newly synthesized albumin. To do so, MDCK II cells expressing hβ2m with or without expression of hFcRn were stably transfected with human albumin and the rate of newly synthesized albumin monitored in the apical or basal secretions over time. MDCK II cells expressing hβ2m and human albumin secreted significantly higher concentrations of human albumin into the apical chamber over all time-points analyzed relative to that observed into the basolateral, or physiologic, chamber (data not shown). Interestingly, when MDCK II cells were forced to also express hFcRn together with hβ2m and human albumin, the predominant direction of vectoral secretion was reversed and observed primarily in the physiologic direction towards the basal chamber (data not shown). Further, we were able to identify evidence for specific and dose-dependent basolateral recycling of human albumin by MDCK II cells that was reliant on the presence of hFcRn as it was not observed in its absence (vector control) or in the presence of rat FcRn which does not bind human albumin (data not shown). Interestingly, we observed high levels of FcRn-independent recycling of albumin at the apical membrane of MDCK-II cells (data not shown). These studies demonstrate that FcRn determines the physiologic accumulation of newly synthesized albumin towards the basal space and away from the apical space or lumen associated with the biliary system. Furthermore, this process is consolidated by the FcRn-mediated recycling of albumin at the basolateral site. FcRn in the liver thus plays an important role in protecting albumin by maintaining this abundant macromolecule in the circulation at its site of synthesis and minimizing loss within the bile.

High serum concentrations of albumin are critical for the maintenance of oncotic pressure and albumin is an important carrier protein for maintaining and trafficking of normally occurring hydrophobic and cationic small molecules, hormones and various drugs like warfarin, phenobutazone, clofibrate, phenytoin and acetaminophen (para-acetylaminophenol, APAP). Due to the prolonged circulating half-life of albumin, such conjugates might be expected to possess persistent toxicity. One example is APAP which, when administered in excess, exhausts hepatocytes's glutathione levels and directly damages the liver. We therefore reasoned that disruption of FcRn interactions with albumin may be useful as a means to enhance the biliary excretion of toxic substances carried by albumin. We approached this by seeking to determine whether the increased biliary loss of albumin in the absence of FcRn expression may also allow for increased excretion of albumin-bound APAP conjugates. We therefore examined the toxicity of APAP in $Fcgrt^{-/-}$ mice. When APAP (600 mg/kg) was administered intraperitoneally (i.p.), $Fcgrt^{-/-}$ mice exhibited significantly greater survival than similarly treated WT mice (data not shown). This was associated with increased excretion of APAP into the bile of Fcgrt in comparison to WT, mice (data not shown) which was observed to bind to albumin (data not shown). At the same time, we observed decreased levels of APAP in the serum of $Fcgrt^{-/-}$ mice (data not shown) relative to WT controls.

As these studies demonstrate that FcRn-deficiency is associated with protection from the toxic consequences of APAP through its increased secretion, we next sought to determine if pharmacologic interventions directed at specific blockade of albumin-FcRn, but not IgG-FcRn, interactions would have a similar beneficial effect. We therefore turned our attention to $hFCGRT^{Tg}/hB2m^{Tg}/mFcgrt^{-/-}$ mice and observed that, as for WT mice, they experienced significantly greater lethality in response to APAP exposure compared to $Fcgrt^{-/-}$ mice, which were largely protected, indicating the usefulness of the humanized mouse model for these studies (data not shown). To examine the feasibility of pharmacologic blockade, we utilized the mouse anti-human FcRn monoclonal antibody ADM31 which specifically blocks albumin-FcRn interactions as confirmed in FIG. 12A, demonstrating ADM31-mediated blockade of albumin transcytosis in transfected MDCK cells. As shown in FIG. 12B, ADM31 treatment protected $hFCGRT^{Tg}/hB2m^{Tg}/mFcgrt^{-/-}$ mice from APAP exposure and reversed the toxicity to levels observed in and equivalent to that associated with $Fcgrt^{-/-}$ mice. These data demonstrate that FcRn-deficiency is associated with decreased susceptibility to APAP toxicity in association with decreased serum persistence and increased biliary excretion of albumin-bound APAP and that this protection can be achieved pharmacologically by specific blockade of albumin-FcRn interactions.

To confirm and extend these therapeutic findings, we used a previously described phage display approach useful in identifying peptides capable of disrupting IgG interactions with FcRn in order to identify a peptide (SYN571, Ac-AGRYFCTKWKHGWCEEVGTGGGK-CONH2) (SEQ ID NO: 3) which bound to shFcRn and was shown to inhibit shFcRn:albumin interactions, but not those of IgG: shFcRn (Table 3).

TABLE 3

Sequence and affinities of FcRn binding peptides.

| Peptide | Sequence | SEQ ID NO: | Competition for albumin or IgG binding to FcRn | Kd, pH 6.0 (Biacore μM) | Kd, pH 7.4 (Biacore μM) |
|---|---|---|---|---|---|
| SYN571 | Ac-AGRYFCTKWKHGWCEEVGTGGGK-CONH2 | 3 | Albumin | 0.50 | 13.1 |
| SYN1753 | Ac-RYFCTKWKHGWCEEVGT-CONH2 | 1 | Albumin | 0.50 | n/a |
| SYN3258 | Ac-RYFCTKWKHGWCEEVGT-GGG-RYFCTKWKHGWCEEVGT-CONH2 | 2 | Albumin | 0.0036 | n/a |
| SYN1327 | Ac-RF-Pen-TGHFG-Sar-NMeLeu-YPC-CONH2 | 123 | IgG | 0.031 | 0.170 |
| SYN1383 | Ac-VMHCFWDEEFRCEYV-CONH2 | 55 | none | 0.032 | 1.1 | n/a = not available; Pen = L-penicillamine; Sar = sarcosine; NMeLeu = L-N-methylleucine By examination of the structure activity relationship, SYN1753 (Ac-RYFCTKWKHGWCEEVGT-CONH2) (SEQ ID NO: 1) was identified as the core sequence of SYN571. To better understand the interactions of SYN1753 with human FcRn, SYN1753 was co-crystallized with soluble human FcRn and the x-ray crystal structure of the complex determined as summarized in Table 4 and FIG. 13A. We found that SYN1753 dimerizes in complex with a single hFcRn molecule at an exposed hydrophobic site (Phe157, His161 and His166) also implicated in albumin binding (FIG. 13B-D). This is also in agreement with the recently published complex structure of HSA:FcRn which shows that the first domain (DI) of HSA binds to hFcRn at the same site as the SYN1753 peptide dimer (FIG. 13E, crystallography description). In the hFcRn SYN1753 dimer complex, the N- and C-termini of the two peptides are in close proximity to each other, suggesting that covalently linking the peptides may improve binding to hFcRn (FIG. 13C,D). We therefore generated a dimeric peptide by fusing two SYN1753 peptides to create SYN3258 (Ac-[SYN1753]-GGG-[SYN1753]-CONH2), a 37-mer that exhibited a higher affinity for FcRn by SPR (3.6 nM at pH 6.0) as compared to the monomeric peptide SYN1753 (~500 nM at pH 6.0). The biologic activity of SYN3258 was confirmed by its ability to inhibit FcRn-directed transcytosis of albumin relative to that observed with a scrambled control peptide (FIG. 12C). Further, when continuously administered at a dose of 40 mg/kg body weight per day via an i.p. pump, SYN3258, but not a control peptide, conferred protection from liver injury associated with acetaminophen-induced toxicity (FIG. 12D) in addition to its ability to improve the survival rate in this model (FIG. 12E). Together, these studies with ADM31 and SYN3258 demonstrate that therapeutic blockade of FcRn-albumin interactions can protect the liver from toxin-induced injury.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be evident to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

It is also noted that peptides, compositions, methods and systems comprising the indicated features are generally contemplated. However, peptides, compositions, methods and systems consisting essentially of the indicated features are also contemplated. In some embodiments, peptides, compositions, methods and systems consisting of the indicated steps are contemplated. The term "comprising" is used in its open-ended meaning indicating that additional features can be included. The term "consisting essentially of" is used to indicate that the essential features are indicated, but that features that do not provide a meaningful or substantial change to the claimed invention, such as purification or buffer changing steps performed between the indicated steps, non-functional groups, superfluous amino acids or non-functional linkers and the like can still be included. The term "consisting of" is intended as a closed term, to indicate that the claim only includes the indicated features.

What is claimed is:

1. A nucleic acid encoding a polypeptide that specifically blocks the interaction between neonatal Fc receptor (FcRn) and albumin, said polypeptide comprising at least one subunit comprising an amino acid sequence at least 90% identical to the amino acid sequence RYFCTKWKHGW-CEEVGT (SEQ ID NO:1), wherein the subunit is up to 20 amino acids in length.

2. The nucleic acid encoding a polypeptide of claim 1, wherein the polypeptide comprises two to four peptide subunits.

3. A vector comprising the nucleic acid according to claim 1.

4. A vector comprising the nucleic acid according to claim 2.

5. A cell comprising the vector according to claim 3.

6. A cell comprising the vector according to claim 4.

7. A cell comprising the nucleic acid according to claim 1.

8. A cell comprising the nucleic acid according to claim 2.

9. An isolated polypeptide capable of binding to a non-IgG and non-albumin competitive site on a FcRn alpha 3 domain comprising the amino acid sequence selected from SEQ ID NO:3, SEQ ID NO:4, SEQ ID NO:5, and SEQ ID NO:6.

10. A composition comprising the isolated polypeptide of claim 9.

11. A nucleic acid encoding an isolated polypeptide of claim 9.

12. A vector comprising the nucleic acid of claim 11.

13. A cell comprising the nucleic acid according to claim 11.

14. A cell comprising the vector according to claim 12.

* * * * *